(12) United States Patent
Baker et al.

(10) Patent No.: US 9,630,896 B2
(45) Date of Patent: Apr. 25, 2017

(54) 2,5-DIALKYL-4-H/HALO/ETHER-PHENOL COMPOUNDS

(71) Applicant: Tansna Therapeutics Inc, Coralville, IA (US)

(72) Inventors: Max Baker, Coralville, IA (US); Rajesh Kumar Mishra, Coralville, IA (US); John J. Talley, St. Louis, MO (US); Eduardo J. Martinez, Bryn Mawr, PA (US)

(73) Assignee: TANSNA THERAPEUTICS, INC., St. Louis, MO (US)

( * ) Notice: Subject to any disclaimer, the term of this patent is extended or adjusted under 35 U.S.C. 154(b) by 75 days.

(21) Appl. No.: 14/551,306

(22) Filed: Nov. 24, 2014

(65) Prior Publication Data

US 2015/0148430 A1    May 28, 2015

Related U.S. Application Data

(60) Provisional application No. 61/907,899, filed on Nov. 22, 2013, provisional application No. 61/907,921, filed on Nov. 22, 2013, provisional application No. 61/907,928, filed on Nov. 22, 2013, provisional application No. 61/907,932, filed on Nov. 22, 2013.

(51) Int. Cl.
| | |
|---|---|
| *A61K 31/05* | (2006.01) |
| *A61K 31/255* | (2006.01) |
| *A61K 31/4365* | (2006.01) |
| *C07C 39/06* | (2006.01) |
| *C07C 39/17* | (2006.01) |
| *C07C 43/23* | (2006.01) |
| *C07C 39/24* | (2006.01) |
| *A61K 31/661* | (2006.01) |
| *A61K 31/7004* | (2006.01) |

(52) U.S. Cl.
CPC .............. *C07C 39/06* (2013.01); *A61K 31/05* (2013.01); *A61K 31/255* (2013.01); *A61K 31/4365* (2013.01); *A61K 31/661* (2013.01); *A61K 31/7004* (2013.01); *C07C 39/17* (2013.01); *C07C 39/24* (2013.01); *C07C 43/23* (2013.01); *C07C 2101/02* (2013.01); *C07C 2101/08* (2013.01)

(58) Field of Classification Search
CPC .. A61K 31/661; A61K 31/05; A61K 31/4365; A61K 31/25; A61K 31/7004
USPC ........................................................ 514/718
See application file for complete search history.

(56) References Cited

U.S. PATENT DOCUMENTS

| | | | |
|---|---|---|---|
| 4,539,355 A | 9/1985 | Takahashi et al. | |
| 4,973,736 A | 11/1990 | Becker et al. | |
| 6,358,995 B1 | 3/2002 | Tagami et al. | |
| 8,044,052 B2 | 10/2011 | Fay et al. | |
| 8,524,761 B2 | 9/2013 | Li et al. | |
| 2005/0148777 A1 | 7/2005 | Carter et al. | |
| 2006/0100460 A1 | 5/2006 | Inoue et al. | |
| 2007/0072873 A1 | 3/2007 | Dehmlow et al. | |
| 2007/0129578 A1 | 6/2007 | Widmaier et al. | |
| 2007/0141113 A1 | 6/2007 | Bezwada | |
| 2008/0312339 A1 | 12/2008 | Baker et al. | |
| 2009/0023701 A1 | 1/2009 | Aungst et al. | |
| 2009/0143413 A1 | 6/2009 | Adams et al. | |
| 2009/0281336 A1 | 11/2009 | Saha et al. | |
| 2010/0016335 A1 | 1/2010 | Iwasawa et al. | |
| 2010/0041555 A1 | 2/2010 | Tsukamoto et al. | |
| 2010/0074976 A1 | 3/2010 | Fowler et al. | |
| 2010/0075994 A1 | 3/2010 | Cao et al. | |
| 2010/0093735 A1 | 4/2010 | Boman et al. | |
| 2011/0152318 A1 | 6/2011 | Woo et al. | |
| 2013/0030012 A1 | 1/2013 | Long et al. | |
| 2013/0109667 A1 | 5/2013 | Markworth et al. | |
| 2013/0184299 A1 | 7/2013 | Ebel et al. | |
| 2016/0060197 A1 | 3/2016 | Qin et al. | |

FOREIGN PATENT DOCUMENTS

| | | |
|---|---|---|
| WO | WO-98/13369 A1 | 4/1998 |
| WO | WO-98/42328 A1 | 10/1998 |
| WO | WO-00/53562 A1 | 9/2000 |
| WO | WO-02/055014 A2 | 7/2002 |

(Continued)

OTHER PUBLICATIONS

Ermili, A., et al. (1977) "Chemical and pharmacologic study on pyran derivatives. IX. Synthesis of 2-dialkylaminochromones", *Farmaco Sci.*, 32(10):713-724 (English Abstract Only).
Reiner, G.N., et al. (2013) "Effects of propofol and other GABAergic phenols on membrane molecular organization", *Colloids and Surfaces B: Biointerfaces*, 101:61-67.
International Search Report and Written Opinion dated Apr. 24, 2015 issued in PCT Patent Application No. PCT/US2014/066844.
Pubchem. 2,5-bis(trifluoromethyl)phenol. Sep. 10, 2005, pp. 1-13 [online], [retrieved on Jan. 13, 2015]. Retrieved from the Internet <URL: http://pubchem.ncbi.nlm.nih.gov/coumpound/23345332#section=3D-Conformer>; p. 3, formula.

(Continued)

*Primary Examiner* — Jennifer M Kim
(74) *Attorney, Agent, or Firm* — Harness, Dickey & Pierce PLC

(57) ABSTRACT

The present disclosure provides phenolic compounds useful in the treatment of neurological conditions such as convulsions and tremors, having the structure of Formula (I):

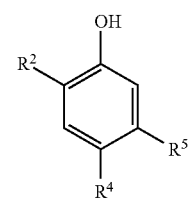

wherein $R^2$, $R^4$, & $R^5$, are as defined in the detailed description; pharmaceutical compositions comprising at least one of the compounds; and methods for treating neurological conditions.

8 Claims, No Drawings

(56) References Cited

FOREIGN PATENT DOCUMENTS

| WO | WO-03/077894 A1 | 9/2003 |
| --- | --- | --- |
| WO | WO-2005/013914 A2 | 2/2005 |
| WO | WO-2005/090307 A1 | 9/2005 |
| WO | WO-2005/121087 A1 | 12/2005 |
| WO | WO-2006/112685 A1 | 10/2006 |
| WO | WO-2010/112485 A1 | 10/2010 |
| WO | WO-2011/140425 A1 | 11/2011 |

OTHER PUBLICATIONS

Pubchem. AGN-PC-03CGVZ. Dec. 5, 2007, pp. 1-10 [online], [retrieved on Jan. 13, 2015]. Retrieved from the Internet <URL: https://pubchem.ncbi.nlm.nih.gov/compound/21531491#section=Top>; p. 3, formula.
Pubchem. AGN-PC-0O6EHK. Feb. 8, 2007, pp. 1-10 [online], [retrieved on Jan. 26, 2015]. Retrieved from the Internet <URL: http://pubchem.ncbi.nlm.nih.gov/compound/12858532#section=Depositor>; p. 3, formula.
Pubchem. CID 2764175. Jul. 19, 2005, pp. 1-10 [online], [retrieved on Jan. 26, 2015]. Retrieved from the Internet <URL: http://pubchem.ncbi.nlm.nih.gov/compound/2764175#section=Top>; p. 3, formula.
Pubchem. CID 58732632. Aug. 19, 2012, pp. 1-11 [online], [retrieved on Jan. 26, 2015]. Retrieved from the Internet <URL: http://pubchem.ncbi.nlm.gov/compound/58732632#section=Top>; p. 3, formula.
Pubchem.AGN-PC-04lOL3. Dec. 5, 2007, pp. 1-12 [online], [retrieved on Jan. 13, 2015]. Retrieved from the Internet <URL: http://pubchem.ncbi.nlm.nih.gov/compound/23345332#section=3D-Conformer>; p. 3, formula.
Pubchem.CID 21874. Mar. 26, 2005, pp. 1-14 [online], [retrieved on Jan. 28, 2015]. Retrieved from Internet <URL: http://pubchem.ncbi.nlm.nih.gov/compound/21874>; p. 3, formula.
Rathore, SS., et al. (2002), "Characterization of Incident Stroke Signs and Symptoms Findings from the Atherosclerosis Risk in Communities Study", *Stroke*, 33(11): 2718-2721.
Pubchem. CID 10364. Mar. 26, 2005, p. 3, Fig [online], [retrieved on Oct. 22, 2015]. Retrieved from the Internet <URL: https://pubchem.ncbi.nlm.nih.gov/compound/10364#section=Top.
Pubchem. CID 21446494. Dec. 5, 2007, p. 3, Fig [online], [retrieved on Oct. 22, 2015]. Retrieved from the Internet <URL: https://pubchem.ncbi.nlm.nih.gov/compound/21446494#section=Top.
Pubchem. CID 57426115. Aug. 8, 2012, p. 3, Fig [online], [retrieved on Oct. 22, 2015]. Retrieved from the Internet <URL: https://pubchem.ncbi.nlm.nih.gov/compound/57426115.
Pubchem. CID 68855429. Nov. 30, 2012, p. 3, Fig [online], [retrieved on Oct. 22, 2015]. Retrieved from the Internet <URL: https://pubchem.ncbi.nlm.nih.gov/compound/68855429.

2,5-DIALKYL-4-H/HALO/ETHER-PHENOL COMPOUNDS

RELATED APPLICATIONS

The present application claims the benefit of and priority to U.S. provisional application Nos. 61/907,899, 61/907,921, 61/907,928, and 61/907,932, all filed 22 Nov. 2013. Each of the aforementioned applications are hereby incorporated by reference in their entirety.

GOVERNMENT RIGHTS

This invention was made with government support under Grant Number 1R43NS076358-01 awarded by the National Institutes of Health. The government has certain rights in the invention.

FIELD OF THE INVENTION

This invention relates to compounds having beneficial effects in the central nervous system (CNS) of mammals. More specifically, this invention relates to compounds that prevent or halt ongoing seizures in mammals, and thus have antiepileptic/anticonvulsant activities that are useful for treating epileptics and other patients having seizures. In addition, the compounds described herein can have anti-inflammatory properties. The compounds disclosed exert anticonvulsant effects while having low side effects. In addition, this invention relates to compounds useful for treating other pathological conditions of the CNS including anxiety, bipolar disorder, chronic or neuropathic pain, migraine headache, depression, schizophrenia, spasticity, tinnitus, and head trauma.

BACKGROUND

Epilepsy is a complex CNS condition involving excessive neuronal discharges that result in the occurrence of seizures (Stefan H, Feuerstein T J, *Pharmacol Therapeut* 2007; 113:165-83).

Seizures may be localized (focal) or generalized within the brain. (Smith M, Wilcox K S, White H S, *Neurotherapeutics* 2007; 4:12-17)

Seizures may be expressed outwardly as convulsions or they may be non-convulsive (Kwan P, Brodie M J, *Expert Opinion on Emerging Drugs* 2007; 12:407-22). Focal (partial) seizures are the most common in humans.

Epilepsy occurs in approximately 0.5 to 1% of the human population (Smith M, Wilcox K S, White H S, *Neurotherapeutics* 2007; 4:12-17). Chronic, daily treatment with anti-epileptic drugs (AEDs) continues to be the standard of care for these patients.

These existing AEDs, however, have varying degrees of effectiveness in suppressing seizures in humans (Stefan H, Feuerstein T J, *Pharmacol Therapeut* 2007; 113:165-83).

In particular, it is estimated that 30% of all epilepsy patients are refractory to current AEDs (Malawska B, Kulig K, *Expert Opin Inv Drug* 2008; 17:361-69).

Epilepsy patients who are refractory, do not respond to the currently available AEDs (Hitiris N, Brodie M J, *Curr Opin Neurol* 2006; 19:175-80).

Refractory epilepsy is defined as failure of adequate trials of two tolerated and appropriately chosen and used AED (anti-epilepsy drug) schedules (whether as monotherapies or in combination) to achieve sustained seizure freedom (Kwan P, Arzimanoglou A, Berg A T, et al. (vol 51, pg 1069, 2010). *Epilepsia* 2010; 51:1922).

Although suboptimal, therapeutic strategies for refractory patients frequently include polytherapy and drug rotation performed on a trial-and-error fashion which usually has limited success (Pathan S A, Jain G K, Akhter S, Vohora D, Ahmad F J, Khar R K, *Drug Discovery Today* 2010; 15:717-32). The percentage of epilepsy patients that remain refractory to available drugs has not improved appreciably over the decades.

Treatment of seizures with anticonvulsant drugs also has drawbacks due to the significant occurrence of side-effects. Common side effects of AEDs include sedation, somnolence, depression and other neuropsychological deficits (Wuttke T V, Lerche H, *Expert Opinion on Investigational Drugs* 2006; 15:1167-77) that interfere with a patient's quality and functioning in daily life. Side effects also are a major limitation to escalating patient doses in attempts to suppress seizures.

As described above, there is a significant need for new anticonvulsant drugs that are more efficacious and have lesser side effects than the currently available compounds. As a group antiseizure compounds are known to interact with a diversity of molecular targets that suppress nerve excitability and likely do so by exerting multiple mechanisms of action. Known mechanisms include effects on voltage-gated ion channels, non-specific cation channels, ligand-gated ion channels, excitatory amino acid receptors, neurotransmitter transporters, and neurotransmitters.

The alkyl substituted phenol, propofol, has good anticonvulsant activity in human status epilepticus (Kinirons P, Doherty C P, *Eur J Emerg Med* 2008; 15:187-95) the most debilitating form of human seizures.

Unfortunately, propofol cannot be used for more widespread and chronic/daily use. (Marik P E, Varon J, *Chest* 2004; 126:582-91).

Although approved for anesthesia, it is only used in acute care settings due to sedation and respiratory depression side-effects (Langley M S, Heel R C, *Drugs* 1988; 35:334-72).

The mechanisms by which propofol inhibits human status epilepticus are unknown. It is believed that propofol's anesthetic/sedative effects result from it being an agonist and potentiator of the $GABA_A$ receptors (Bali M, Akabas M H, *Mol Pharmacol* 2004; 65:68-76)

The mode of action of propofol analogs is similarly elusive (Krasowski M D, Jenkins A, Flood P, Kung A Y, Hopfinger A J, Harrison N L, *Journal of Pharmacology and Experimental Therapeutics* 2001; 297:338-51).

$GABA_A$ receptor agonism/potentiation is also known to be a mechanism of some anticonvulsant compounds (Myhrer T, Nguyen N H T, Enger S, Aas P, *Arch Toxicol* 2006; 80:502-07).

$GABA_A$ receptor agonism/potentiation is presumed to be a component of propofol's anticonvulsant mechanism (Ragavendran J V, Sriram D, Kotapati S, Stables J, Yogeeswari P, *European Journal of Medicinal Chemistry* 2008; 43:2650-55).

$GABA_A$ receptor stimulation depresses nerve conduction by hyperpolarizing the neuronal membrane and suppressing impulse conduction. GABA receptors, which exist as multiple isoforms with different sensitivities to agonists (Atack J R, *Curr Top Med Chem* 2011; 11:1176-202).

GABA receptors are known to be present in nerves that excessively fire causing seizures. Other studies show that propofol can block sodium channels (Jones P J, Wang Y S, Smith M D, et al., *J Pharmacol Exp Ther* 2007; 320:828-36).

Propofol has also been reported to down-regulate glutamatergic synaptic transmission (Snyder G L, Galdi S, Hendrick J P, Hemmings H C, *Neuropharmacology* 2007; 53:619-30), other known anticonvulsant mechanisms. Unlike the barbiturate or benzodiazepine drug families, which have different members useful for anesthesia/sedation and anticonvulsant activity, propofol is the sole member of the alkyl phenolic class on the market.

Previously it has been shown that carvacrol, thymol, and other substituted phenols in essential oils have antibacterial and antifungal properties and cause. (Stefanakis et al. (2013) *Food Control* 34:539-46).

Certain substituted phenols show bacteriostatic and bacteriocidal effects toward *Eschericia coli, Staphylococcus aureus, Listeria monocytogenes,* and *Bacillus cereus* (Klein et al. (2013) *Current Microbiology* 67: 200-08).

DESCRIPTION OF THE RELATED ART

Compounds useful as voltage-gated sodium channel inhibitors are described by Hadidah-Ruah et al., in WO 2011/140425 published 10 Nov. 2008. The compounds described therein include 4-iodo-2,5-dimethyl-phenol used as an intermediate to make 4-isopropoxy-2,5-dimethylbenzoic acid. 4-isopropoxy-2,5-dimethylbenzoic acid is used as an intermediate in a multi-step process to make compounds useful as voltage-gated sodium channel inhibitors.

Amine containing compounds useful for mainly excitatory CNS effects are described in Ermili et al., *Edizione Scientifica,* 32(10):713-24 (1977). 4-chloro-2-isopropyl-5-methylphenol is used as an intermediate to make compounds which had mainly excitatory CNS effects. Two end product compounds, Ve (2-dimethylamino-6-methylchromone) and Vs (2-(dimethylamino)-4H-benzo[h]chromen-4-one), have weak anti-convulsant activity. 4-chloro-2-isopropyl-5-methylphenol is not used as an intermediate in the synthesis of these two compounds.

Phenol derivatives with known GABAnergic activity and structurally similar phenol derivatives were tested for lipophilic parameters because GABA receptors are present in cell membranes in Reiner et al., *Colloids and Surfaces, B: Biointerfaces,* 101:61-67 (2013). Reiner et al. considered 4-chloro-2-isopropyl-5-methylphenol to be structurally related to the compound thymol, which has known GABAnergic activity, so 4-chloro-2-isopropyl-5-methylphenol was tested for membrane interaction. All five phenol derivatives tested were shown to interact with membranes.

SUMMARY OF THE INVENTION

In a first embodiment (Embodiment 1), a method is provided for treating and/or improving a condition selected from the group consisting of Alzheimer's Disease, anxiety, bipolar disorder, convulsions, dementia, depression, epilepsy, fibromyalgia, Huntington's Chorea, mania, memory, migraine, multiple sclerosis, neuropathic pain, Parkinson's Disease, seizures, tinnitus, Tourette's Syndrome, and tremors, comprising administering a therapeutically effective amount of a compound or pharmaceutically acceptable salt of the compound, wherein the compound has the structure of Formula (I):

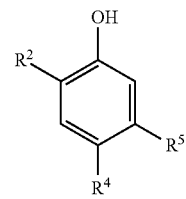

wherein:

$R^2$ is selected from the group consisting of alkyl, haloalkyl, and cycloalkyl;

$R^4$ is selected from the group consisting of H, halo, and alkoxy, wherein the alkoxy may be optionally substituted with one or more substituents independently selected from the group consisting of alkyl and halo, and wherein $R^4$ is not methyl; and $R^5$ is selected from the group consisting of alkyl, haloalkyl, and cycloalkyl.

Embodiment 2 is the method of Embodiment 1 wherein each of $R^2$ and $R^5$ has between one and five carbons.

Embodiment 3 is the method of Embodiment 1 wherein the condition is epilepsy, seizures, or convulsions.

Embodiment 4 is the method of Embodiment 1 wherein the condition is neuropathic pain or fibromyalgia.

Embodiment 5 is the method of Embodiment 1 wherein the condition is a psychological disorder.

Embodiment 6 is the method of Embodiment 5 wherein the psychological disorder is anxiety, mania, bipolar disorder, or depression.

Embodiment 7 is the method of Embodiment 1, wherein the condition is Alzheimer's Disease, Huntington's Disease, Multiple Sclerosis, Parkinson's disease, Tourette's Syndrome, tinnitus, and tremors.

Embodiment 8 is the method of Embodiment 1, wherein:

$R^2$ is selected from the group consisting of alkyl, haloalkyl, and cycloalkyl;

$R^4$ is halo.

Embodiment 9 is the method of Embodiment 8, wherein:

$R^4$ is selected from the group consisting of Br, Cl, and F.

Embodiment 10 is the method of Embodiment 9, wherein:

$R^2$ is alkyl; and $R^5$ is alkyl having two or more carbons.

Embodiment 11 is the method of Embodiment 10, wherein the compound is selected from a group consisting of: 4-chloro-5-tert-butyl-2-methyl-phenol; 4-chloro-2-isopropyl-5-methyl-phenol; 4-fluoro-2-isopropyl-5-methyl-phenol; 4-chloro-2,5-diisopropyl-phenol; 4-bromo-5-isopropyl-2-methyl-phenol; 4-bromo-2-isopropyl-5-methyl-phenol; and 4-bromo-2-tert-butyl-5-isopropyl-phenol.

Embodiment 12 is the method of Embodiment 1, wherein the compound has the structure of Formula (II):

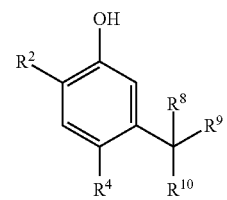

wherein:

R² is selected from the group consisting of alkyl, haloalkyl, and cycloalkyl;

R⁴ is selected from the group consisting of Br, Cl, and F; and

R⁸, R⁹ and R¹⁰ are each independently selected from the group consisting of H, alkyl, and haloalkyl.

Embodiment 13 is the method of Embodiment 1, wherein the compound has the structure of Formula (III):

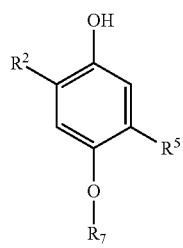

(III)

wherein:

R² is selected from the group consisting of alkyl, haloalkyl, and cycloalkyl;

R⁵ is selected from the group consisting of alkyl, haloalkyl, and cycloalkyl; and R⁷ is selected from the group consisting of alkyl and haloalkyl.

Embodiment 14 is the method of Embodiment 13, wherein:

R² is selected from the group consisting of alkyl, haloalkyl, and cycloalkyl;

R⁵ is selected from the group consisting of alkyl, haloalkyl, and cycloalkyl; and R⁷ is alkyl.

Embodiment 15 is the method of Embodiment 14, wherein the compound has the structure of Formula (IV):

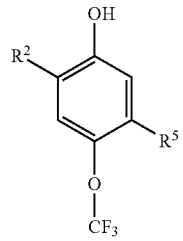

(IV)

wherein:

R² is selected from the group consisting of alkyl, haloalkyl, and cycloalkyl; and R⁵ is selected from the group consisting of alkyl, haloalkyl, and cycloalkyl.

Embodiment 16 is the method of Embodiment 15, wherein:

R² is selected from the group consisting of alkyl and cycloalkyl; and

R⁵ is selected from the group consisting of alkyl and cycloalkyl.

In yet another embodiment (Embodiment 17) a compound is provided, selected from the group consisting of: 4-bromo-5-ethyl-2-methyl-phenol; 4-fluoro-5-isopropyl-2-methyl-phenol; 4-bromo-5-tert-butyl-2-methyl-phenol; 4-bromo-5-cyclopropyl-2-methyl-phenol; 4-bromo-2-ethyl-5-isopropyl-phenol; 4-chloro-2-ethyl-5-isopropyl-phenol; 2-ethyl-4-fluoro-5-isopropyl phenol; 4-bromo-5-isopropyl-2-propyl-phenol, 5-isopropyl-2-propyl-phenol; and 4-bromo-2,5-isopropyl-phenol.

In yet another embodiment (Embodiment 18) a compound is provided, selected from the group consisting of: 4-bromo-2-methyl-5-(2,2,2-trifluoro-1-methyl-ethyl)-phenol; 4-bromo-5-(2-fluoro-1-methyl-ethyl)-2-methyl-phenol; 4-bromo-2-methyl-5-(2,2,2-trifluoro-1-trifluoromethyl-ethyl)-phenol; 4-bromo-2-trifluoromethyl-5-(2,2,2-trifluoro-1-methyl-ethyl)-phenol; 4-bromo-2-cyclopropyl-5-isopropyl-phenol; 4-bromo-2,5-dicyclopropyl-phenol; 5-isopropyl-2-methyl-4-trifluoromethoxy-phenol; 2-cyclopropyl-5-isopropyl-4-trifluoromethoxy-phenol; 5-cyclopropyl-2-methyl-4-trifluoromethoxy-phenol; 2,5-dicyclopropyl-4-trifluoromethoxy-phenol; 4-tert-butoxy-5-cyclopropyl-2-methyl-phenol; 4-tert-butoxy-2-cyclopropyl-5-methyl-phenol; 4-tert-butoxy-2,5-dicyclopropyl-phenol; 4-isopropoxy-5-isopropyl-2-methyl-phenol; 4-bromo-5-isopropyl-2-trifluoromethyl-phenol; 4-bromo-5-(2-fluoro-1-methyl-ethyl)-2-methyl-phenol; and 4-tert-butoxy-5-isopropyl-2-methyl-phenol.

In yet another embodiment (Embodiment 19) a compound or pharmaceutically acceptable salt of the compound is provided, wherein the compound has the structure of Formula (V):

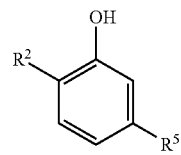

(V)

wherein:

R² is selected from the group consisting of haloalkyl and cycloalkyl.

R⁵ is selected from the group consisting of haloalkyl and cycloalkyl.

Embodiment 20 is the compound of Embodiment 19, wherein:

R² is selected from the group consisting of trifluoroalkyl and cycloalkyl

R⁵ is selected from the group consisting of trifluoroalkyl and cycloalkyl.

In yet another embodiment (Embodiment 21) a compound is provided, selected from the group consisting of: 5-(1,2-dimethyl-propyl)-2-methyl-phenol; 5-isobutyl-2-methyl-phenol; 5-cyclopentyl-2-methyl-phenol; 5-sec-butyl-2-ethyl-phenol; 5-butyl-2-propyl-phenol; 5-isopropyl-2-propyl-phenol; 5-sec-butyl-2-propyl-phenol; 5-tert-butyl-2-propyl-phenol; 2-butyl-5-isopropyl-phenol; 2-butyl-5-sec-butyl-phenol; 5-(tert-butyl)-2-butylphenol; 2-isopropyl-5-propyl-phenol; 5-sec-butyl-2-isopropyl-phenol; 2-sec-butyl-5-ethyl-phenol; 2-sec-butyl-5-propyl-phenol; 5-butyl-2-sec-butyl-phenol; 2-sec-butyl-5-isopropyl-phenol; 5-sec-butyl-2-tert-butyl-phenol; 2-methyl-5-(2,2,2-trifluoro-1-methyl-ethyl)-phenol; 5-(2-fluoro-1-methyl-ethyl)-2-methyl-phenol; 2-methyl-5-(2,2,2-trifluoro-1-trifluoromethyl-ethyl)-phenol; 2-trifluoromethyl-5-(2,2,2-trifluoro-1-methyl-ethyl)-phenol; 5-isopropyl-2-(1-methyl-butyl)-phenol; 2-isopropyl-5-isopropyl-phenol; 2-cyclopropyl-5-isopropyl-phenol; and 2,5-dicyclopropyl-phenol.

In yet another embodiment (Embodiment 22), a compound or pharmaceutically acceptable salt of the compound is provided, wherein the compound has the structure of Formula (I):

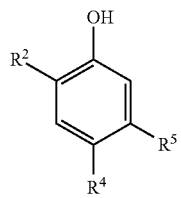

(I)

wherein:
$R^2$ is selected from the group consisting of methyl, cycloalkyl, and —$CF_3$;
$R^4$ is halo;
$R^5$ is selected from the group consisting of fluoroalkyl and a three, four, or five carbon cycloalkyl.

Embodiment 23 is the compound of Embodiment 22, wherein:
$R^4$ is selected from the group consisting of Br, Cl, and F.

In yet another embodiment (Embodiment 24) a compound or pharmaceutically acceptable salt of the compound is provided, wherein the compound has the structure of Formula (III):

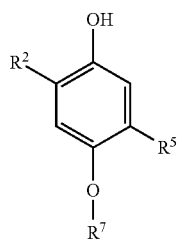

(III)

wherein,
$R^2$ and $R^5$ are each independently selected from the group consisting of alkyl and cycloalkyl; wherein at least one of $R^2$ and $R^5$ is cycloalkyl.
$R^7$ is selected from the group consisting of isopropyl, tert-butyl, and haloalkyl.

Embodiment 25 is the compound of Embodiment 24, wherein:
$R^7$ is selected from the group consisting of isopropyl and tert-butyl.

Embodiment 26 is the compound or pharmaceutically acceptable salt of the compound of Embodiment 22, wherein the compound has the structure of Formula (IV):

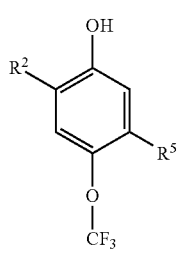

(IV)

wherein:
$R^2$ is selected from the group consisting of alkyl, and cycloalkyl; and
$R^5$ is selected from the group consisting of alkyl, and cycloalkyl.

DETAILED DESCRIPTION

The following description is merely exemplary in nature and is not intended to limit the present disclosure, application, or uses.

A. Definitions

The use of generic terms in the description of the compounds are herein defined for clarity. The terms "substituent", "radical", "group", "moiety" and "fragment" may be used interchangeably.

If a substituent is described as being "optionally substituted," the substituent may be either (1) not substituted or (2) substituted on a substitutable position. If a substitutable position is not substituted, the default substituent is H.

Singular forms "a" and "an" may include plural reference unless the context clearly dictates otherwise.

The number of carbon atoms in a substituent can be indicated by the prefix "$C_{A-B}$" where A is the minimum and B is the maximum number of carbon atoms in the substituent.

The terms "hydroxyl" and "hydroxy" may be used interchangeably.

The term "halo" refers to fluoro (—F), chloro (—Cl), bromo (—Br), or iodo (—I).

The term "alkyl" denotes a linear or branched acyclic alkyl radical containing from 1 to about 15 carbon atoms. In some embodiments, alkyl is a $C_{1-10}$alkyl, $C_{1-7}$alkyl, $C_{1-6}$alkyl or $C_{1-5}$alkyl radical. Examples of alkyl include, but are not limited to, methyl, ethyl, propyl, isopropyl, butyl, isobutyl, tert-butyl, sec-butyl, pentan-3-yl and the like.

The term "heteroatom" denotes an atom other than carbon or hydrogen, found in the context of an organic compound. Non-limiting exemplary heteroatoms include N, O, P, and S.

The term "heteroalkyl" denotes an alkyl that comprises one or more heteroatoms. A heteroatom in a heteroalkyl can be found in the middle and/or at the distal terminus of the alkyl chain.

The term "alkylcarbonyl" denotes an alkyl radical attached to carbonyl.

The term "hydroxyalkyl" embraces a radical wherein any one or more of an alkyl carbon is substituted with a hydroxyl radical as defined above, for example, monohydroxyalkyl, dihydroxyalkyl and trihydroxyalkyl. More specific examples of hydroxyalkyl include hydroxymethyl, hydroxyethyl and hydroxypropyl.

Hydroxyalkyl may be substituted with, for example, alkyl, hydroxyalkoxy, hydroxyalkoxyalkyl, amino, aminoalkyl, aryl, aralkyl, and heterocyclyl. Further non-limiting examples include hydroxyalkyl substituted with methyl, isobutyl, benzyl, isopropyl, benzyl and sec-butyl.

The term "hydroxyalkoxy" denotes a hydroxy radical attached to an alkoxy radical.

The term "hydroxyalkoxyalkyl" denotes a hydroxyalkoxy radical attached to an alkyl radical. Non-limiting examples include hydroxyethyl-O-ethyl and hydroxylmethyl-O-ethyl.

Hydroxyalkoxyalkyl may, for example, be substituted with alkyl, hydroxyalkyl, hydroxyalkoxy, amino, aminoalkyl, aryl, aralkyl, and heterocyclyl. Further non-limiting examples include hydroxyalkoxyalkyl substituted with methyl, isobutyl, benzyl, isopropyl and sec-butyl. More specific non-limiting examples of substituted hydroxyalkoxyalkyl include hydroxyethyl-O-ethyl substituted with methyl, isobutyl, benzyl, isopropyl and sec-butyl.

The term "haloalkyl" embraces an alkyl radical wherein any one or more of the alkyl carbon atoms is substituted with halo as defined above. For example, monohaloalkyl, dihaloalkyl and trihaloalkyl. A monohaloalkyl radical, for one example, may have either a bromo, chloro or a fluoro atom within the radical. A dihalo radical may have two of the same halo radicals or a combination of different halo radicals. A trihaloalkyl radical may have three of the same halo radicals or a combination of different halo radicals. Non-limiting examples of haloalkyl include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl, dichloropropyl, iodomethyl, diiodomethyl and triiodomethyl.

The term "alkoxy" is RO— where R is alkyl as defined above. Non-limiting examples of alkoxy radicals include methoxy, ethoxy and propoxy. The terms "alkyloxy" and "alkoxy" and "alkyl-O—" may be used interchangeably.

The term "phosphonooxyalkyl" is —RO—P(O)(OH)$_2$, where R is alkyl as defined above. The term "phosphonooxyalkyl" should also be understood to include salts. Non-limiting examples of phosphonooxyalkyl radicals include

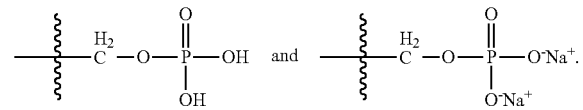

The term "alkoxyalkyl" refers to an alkyl moiety substituted with an alkoxy radical. Examples of alkoxyalkyl radicals include methoxymethyl, methoxyethyl, methoxypropyl and ethoxyethyl.

The term "alkoxycarbonyl" refers to an carbonyl radical substituted with alkoxy. Non-limiting examples include methoxycarbonyl and ethoxycarbonyl.

The term "alkoxycarbonylalkyl" refers to an alkoxycarbonyl radical substituted with alkyl.

The term "carbonyl" denotes a carbon radical having two of four covalent bonds shared with a single oxygen atom.

The term "alkylcarbonyl" denotes an alkyl radical attached to a carbonyl radical.

The term "carbonylalkyl" denotes a carbonyl radical attached to an alkyl radical.

The term "carbonylalkylcarbonyl" denotes a carbonylalkyl radical attached to a carbonyl radical.

The term "cyclic ring" embraces any aromatic or non-aromatic cyclized carbon radical (e.g., aryl and cycloalkyl respectively) which may contain one or more ring heteroatoms (e.g., heteroaryl and heterocyclyl). A cyclic ring may be unsaturated, partially unsaturated, or saturated.

The term "cycloalkyl" embraces any monocyclic, bicyclic or tricyclic cyclized carbon radical of 3 to about 15 carbon atoms that is fully or partially saturated. Cycloalkyl may be attached to an aryl, cycloalkyl or a heterocyclyl radical in a fused or pendant manner.

Cycloalkyl may be substituted with alkyl, alkoxy, carboxyalkyl, hydroxyalkyl, amino, acylamino, amido, alkylamino, nitrooxyalkyl, nitrooxy, carbonyl, acyl, aralkyl, aryl, heterocyclyl or cycloalkyl.

The term "aryl" refers to any monocyclic, bicyclic or tricyclic cyclized carbon radical, wherein at least one ring is aromatic. An aromatic radical may be attached to a non-aromatic cycloalkyl or heterocyclyl radical in a fused or pendant manner. Examples of aryl radicals include, but are not limited to, phenyl and naphthyl.

The term "aralkyl" embraces aryl attached to an alkyl radical and may be used interchangeably with arylalkyl. Examples of aralkyl include benzyl, diphenylmethyl, triphenylmethyl, phenylethyl and diphenylethyl. The terms "benzyl" and "phenylmethyl" may be used interchangeably.

The term "aralkoxy" embraces an arylalkyl radical attached through an oxygen atom to the parent molecular scaffold. The terms "arylalkoxy" and "aralkoxy" may be used interchangeably.

The term "aryloxy" is RO—, where R is aryl.

The term "aryloxyalkyl" embraces an aryloxy radical attached to an alkyl radical.

The term "pharmaceutically-acceptable" means suitable for use in pharmaceutical preparations, generally considered as safe for such use, officially approved by a regulatory agency of a national or state government for such use, or being listed in the U. S. Pharmacopoeia or other generally recognized pharmacopoeia for use in animals, and more particularly in humans.

The term "pharmaceutically-acceptable salt" refers to a salt which is suitable for use in pharmaceutical preparations. The term "therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

The term "solvate" denotes a molecular or ionic complex of molecules or ions of solvent with those of a compound of the present invention. The term "solvate" embraces the term "hydrate".

The term "hydrate" denotes a compound of the present invention containing water combined in the molecular form.

Some of the compounds described contain one or more stereocenters and are meant to include R, S and mixtures of R and S forms for each stereocenter present.

The term "AED" refers to "Anti-Epileptic Drug." AED can be used interchangeably with "ASD," which means "Anti-Seizure Drug."

B. Compounds

The present disclosure provides a compound having the structure of Formula (I). All compounds shown in the tables below should be understood optionally to include one or more deuterium or tritium hydridos wherever a hydrogen atom is indicated or implied:

Family 1a Species

| Example Number | Species Structure Species Name |
|---|---|
| Methyl series | |
| 1 | 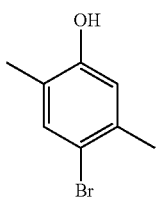<br>4-Bromo-2,5-dimethyl-phenol |

-continued

| Example Number | Species Structure Species Name |
|---|---|
| 2 | 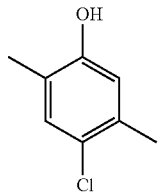<br>4-Chloro-2,5-dimethyl-phenol |
| 3 | 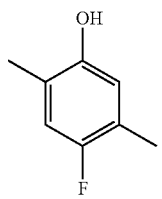<br>4-Fluoro-2,5-dimethyl-phenol |
| 4 | 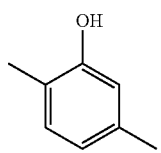<br>2,5-Dimethyl-phenol |
| 5 | 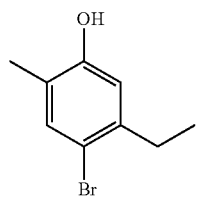<br>4-Bromo-5-ethyl-2-methyl-phenol |
| 6 | 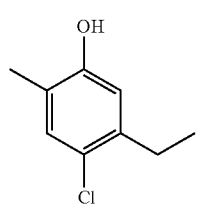<br>4-Chloro-5-ethyl-2-methyl-phenol |
| 7 | 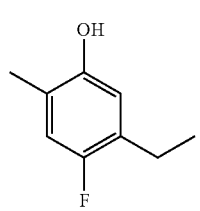<br>5-Ethyl-4-fluoro-2-methyl-phenol |

-continued

| Example Number | Species Structure Species Name |
|---|---|
| 8 | 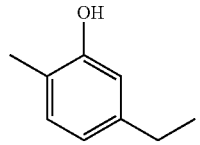<br>5-Ethyl-2-methyl-phenol |
| 9 | 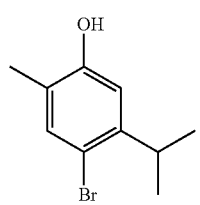<br>4-Bromo-5-isopropyl-2-methyl-phenol |
| 10 | 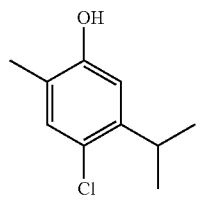<br>4-Chloro-5-isopropyl-2-methyl-phenol |
| 11 | 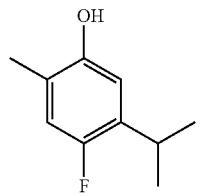<br>4-Fluoro-5-isopropyl-2-methyl-phenol |
| 12 | 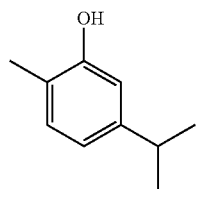<br>5-Isopropyl-2-methyl-phenol |
| 13 | 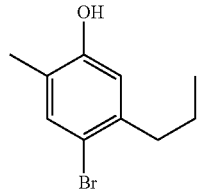<br>4-Bromo-2-methyl-5-propyl-phenol |

| Example Number | Species Structure Species Name |
|---|---|
| 14 | 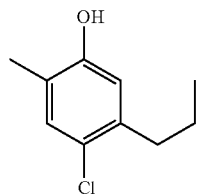<br>2-methyl, 4-chloro, 5-n-propyl phenol |
| 15 | 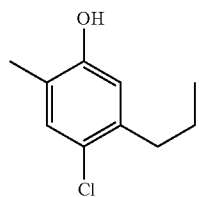<br>4-Chloro-2-methyl-5-propyl-phenol |
| 16 | 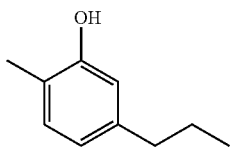<br>2-Methyl-5-propyl-phenol |
| 17 | 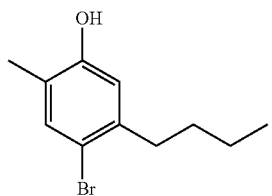<br>4-Bromo-5-butyl-2-methyl-phenol |
| 18 | 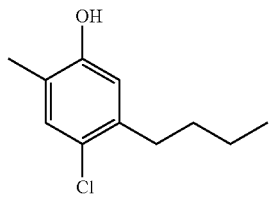<br>5-Butyl-4-chloro-2-methyl-phenol |
| 19 | 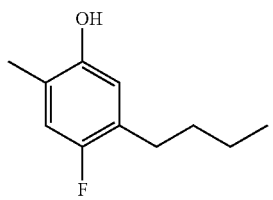<br>5-Butyl-4-fluoro-2-methyl-phenol |
| 20 | 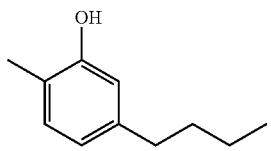<br>5-Butyl-2-methyl-phenol |
| 21 | 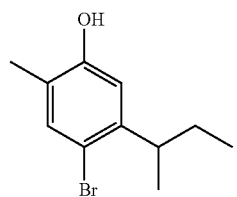<br>4-Bromo-5-sec-butyl-2-methyl-phenol |
| 22 | 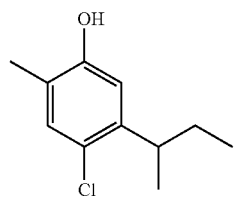<br>5-sec-Butyl-4-chloro-2-methyl-phenol |
| 23 | 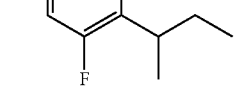<br>5-sec-Butyl-4-fluoro-2-methyl-phenol |
| 24 | 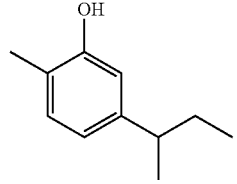<br>5-sec-Butyl-2-methyl-phenol |
| 25 | 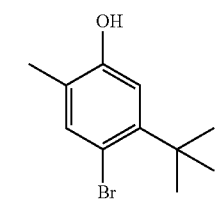<br>4-Bromo-5-tert-butyl-2-methyl-phenol |

| Example Number | Species Structure Species Name |
|---|---|
| 26 | 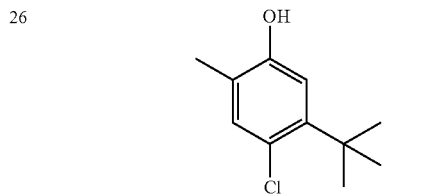
5-tert-Butyl-4-chloro-2-methyl-phenol |
| 26 | 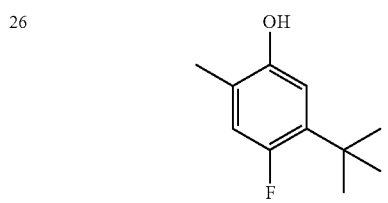
5-tert-Butyl-4-fluoro-2-methyl-phenol |
| 28 | 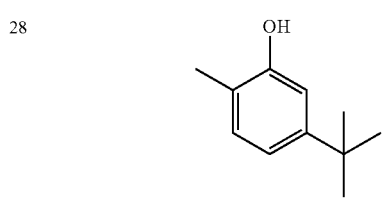
5-tert-Butyl-2-methyl-phenol |
| 29 | 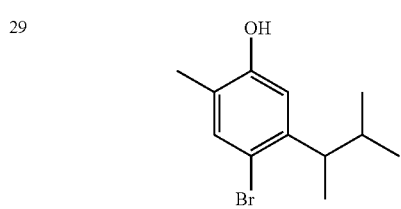
4-Bromo-5-(1,2-dimethyl-propyl)-2-methyl-phenol |
| 30 | 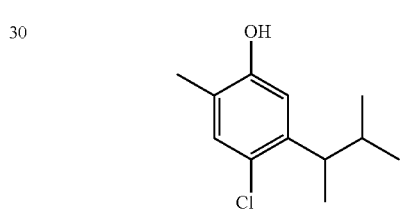
4-Chloro-5-(1,2-dimethyl-propyl)-2-methyl-phenol |
| 31 | 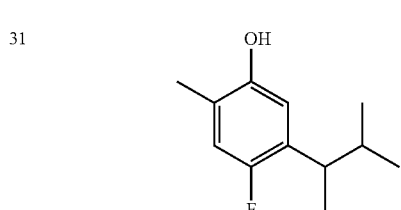
5-(1,2-Dimethyl-propyl)-4-fluoro-2-methyl-phenol |

| Example Number | Species Structure Species Name |
|---|---|
| 32 | 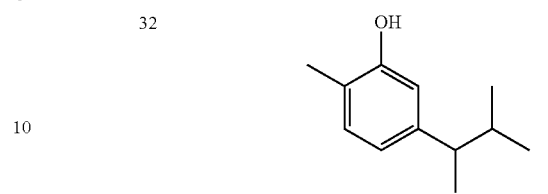
5-(1,2-Dimethyl-propyl)-2-methyl-phenol |
| 33 | 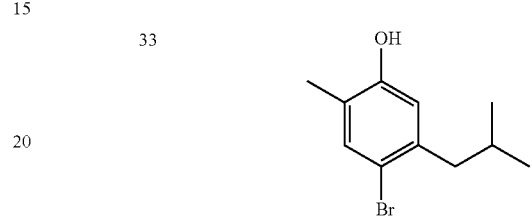
4-Bromo-5-isobutyl-2-methyl-phenol |
| 34 | 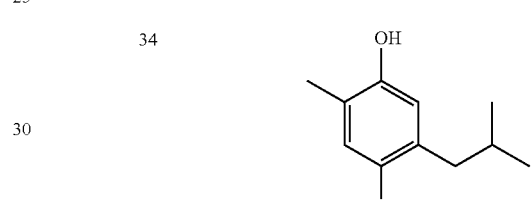
4-Chloro-5-isobutyl-2-methyl-phenol |
| 35 | 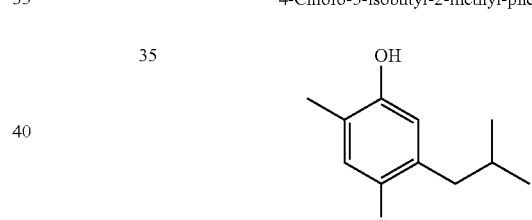
4-Fluoro-5-isobutyl-2-methyl-phenol |
| 40 | 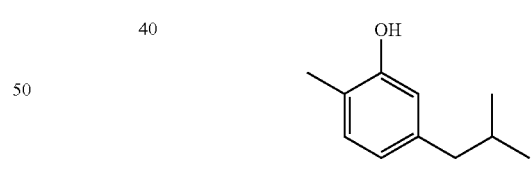
5-Isobutyl-2-methyl-phenol |
| 41 | 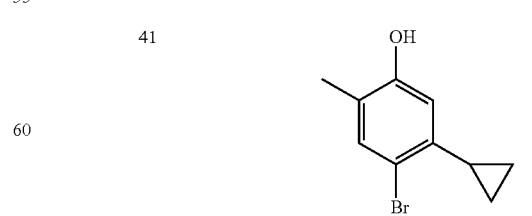
4-Bromo-5-cyclopropyl-2-methyl-phenol |

| Example Number | Species Structure Species Name |
|---|---|
| 42 | 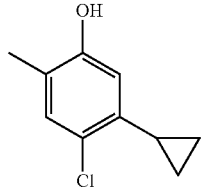
4-Chloro-5-cyclopropyl-2-methyl-phenol |
| 43 | 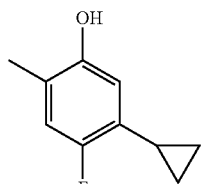
5-Cyclopropyl-4-fluoro-2-methyl-phenol |
| 44 | 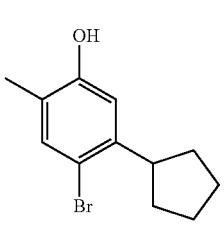
4-Bromo-5-cyclopentyl-2-methyl-phenol |
| 45 | 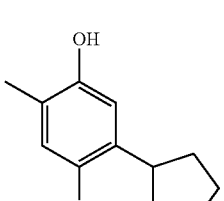
4-Chloro-5-cyclopentyl-2-methyl-phenol |
| 46 | 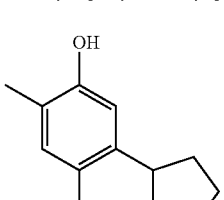
5-Cyclopentyl-4-fluoro-2-methyl-phenol |
| 47 | 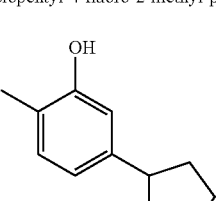
5-Cyclopentyl-2-methyl-phenol |

| Example Number | Species Structure Species Name |
|---|---|
| Ethyl Series | |
| 48 | 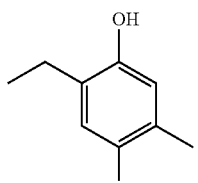
4-Bromo-2-ethyl-5-methyl-phenol |
| 49 | 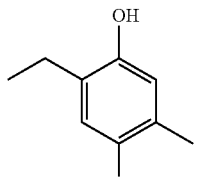
4-Chloro-2-ethyl-5-methyl-phenol |
| 50 | 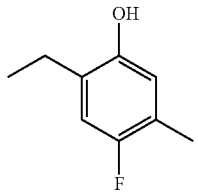
2-Ethyl-4-fluoro-5-methyl-phenol |
| 51 | 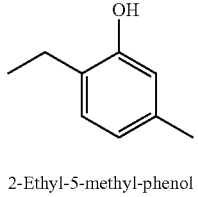
2-Ethyl-5-methyl-phenol |
| 52 | 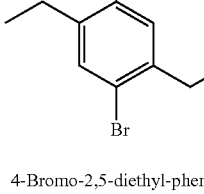
4-Bromo-2,5-diethyl-phenol |
| 53 | 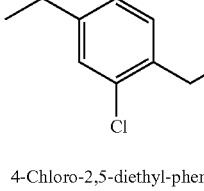
4-Chloro-2,5-diethyl-phenol |

| Example Number | Species Structure Species Name |
|---|---|
| 54 | 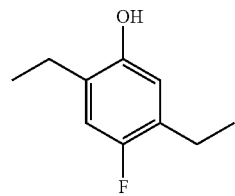
2,5-Diethyl-4-fluoro-phenol |
| 55 | 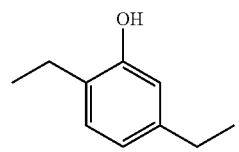
2,5-Diethyl-phenol |
| 56 | 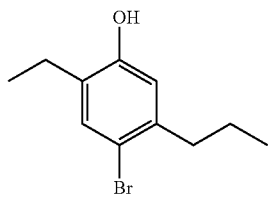
4-Bromo-2-ethyl-5-propyl-phenol |
| 57 | 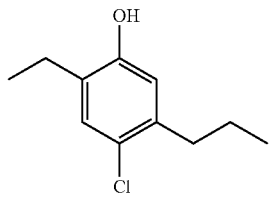
4-Chloro-2-ethyl-5-propyl-phenol |
| 58 | 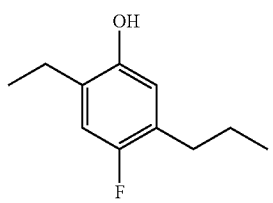
2-Ethyl-4-fluoro-5-propyl-phenol |
| 59 | 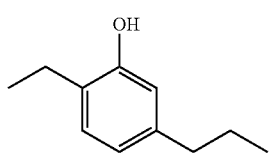
2-Ethyl-5-propyl-phenol |

| Example Number | Species Structure Species Name |
|---|---|
| 60 | 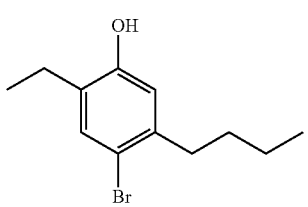
4-Bromo-5-butyl-2-ethyl-phenol |
| 61 | 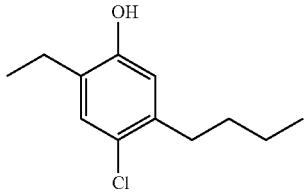
5-Butyl-4-chloro-2-ethyl-phenol |
| 62 | 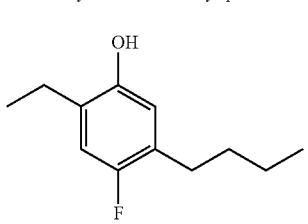
5-Butyl-2-ethyl-4-fluoro-phenol |
| 63 | 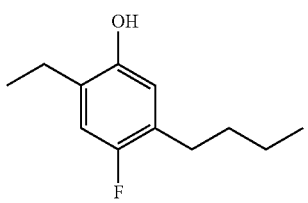
5-Butyl-2-ethyl-phenol |
| 64 | 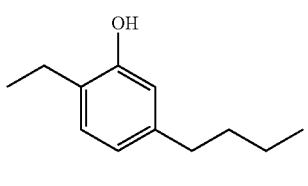
4-Bromo-2-ethyl-5-isopropyl-phenol |
| 65 | 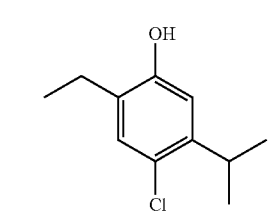
4-Chloro-2-ethyl-5-isopropyl-phenol |

-continued

| Example Number | Species Structure Species Name |
|---|---|
| 66 | 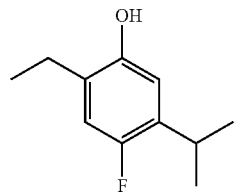 2-Ethyl-4-fluoro-5-isopropyl-phenol |
| 67 | 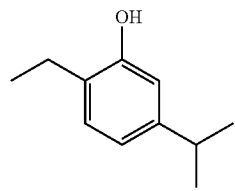 2-Ethyl-5-isopropyl-phenol |
| 68 | 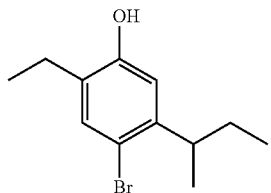 4-Bromo-5-sec-butyl-2-ethyl-phenol |
| 69 | 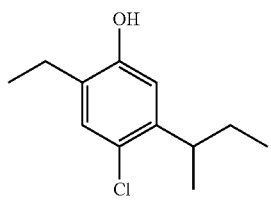 5-sec-Butyl-4-chloro-2-ethyl-phenol |
| 70 | 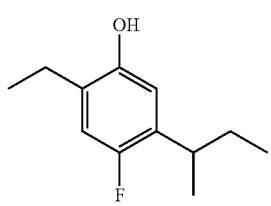 5-sec-Butyl-2-ethyl-4-fluoro-phenol |
| 71 | 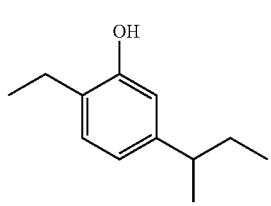 5-sec-Butyl-2-ethyl-phenol |

-continued

| Example Number | Species Structure Species Name |
|---|---|
| 72 | 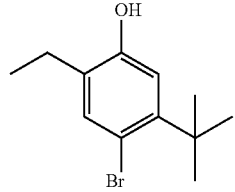 4-Bromo-5-tert-butyl-2-ethyl-phenol |
| 73 | 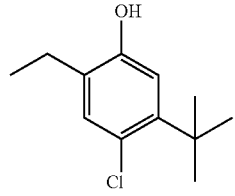 5-tert-Butyl-4-chloro-2-ethyl-phenol |
| 74 | 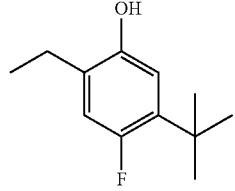 5-tert-Butyl-2-ethyl-4-fluoro-phenol |
| 75 | 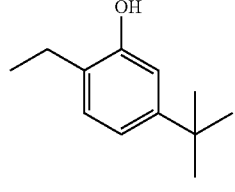 5-tert-Butyl-2-ethyl-phenol |
| Propyl series | |
| 76 | 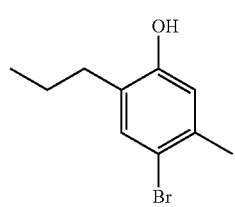 4-Bromo-5-methyl-2-propyl-phenol |
| 77 | 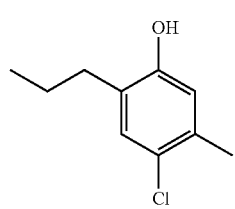 4-Chloro-5-methyl-2-propyl-phenol |

| Example Number | Species Structure Species Name |
|---|---|
| 78 | 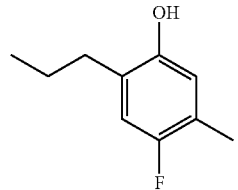<br>4-fluoro-5-methyl-2-propylphenol |
| 79 | 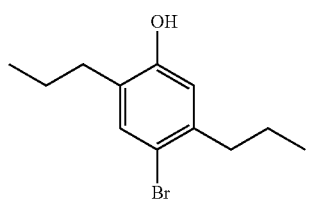<br>5-Methyl-2-propyl-phenol |
| 80 | 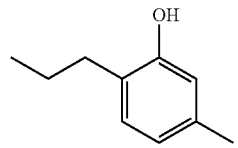<br>4-Bromo-5-ethyl-2-propyl-phenol |
| 81 | 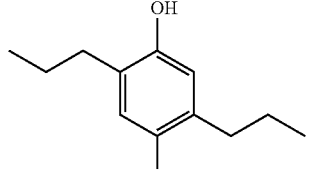<br>4-Chloro-5-ethyl-2-propyl-phenol |
| 82 | 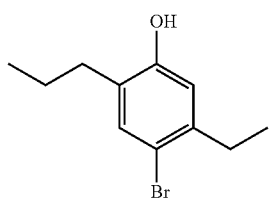<br>5-Ethyl-4-fluoro-2-propyl-phenol |
| 83 | 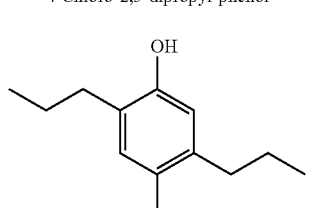<br>5-Ethyl-2-propyl-phenol |
| 84 | 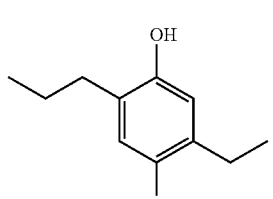<br>4-Bromo-2,5-dipropyl-phenol |
| 85 | 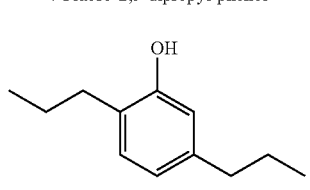<br>4-Chloro-2,5-dipropyl-phenol |
| 86 | 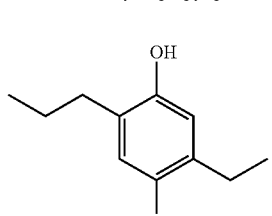<br>4-Fluoro-2,5-dipropyl-phenol |
| 87 | 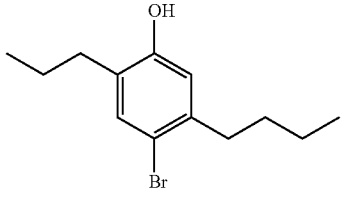<br>2,5-Dipropyl-phenol |
| 88 | 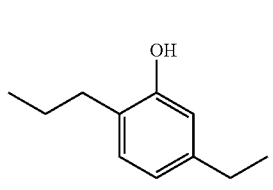<br>4-Bromo-5-butyl-2-propyl-phenol |
| 89 | 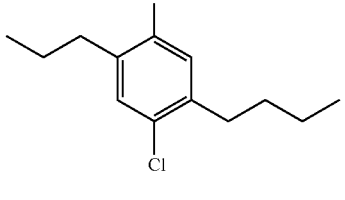<br>5-Butyl-4-chloro-2-propyl-phenol |

| Example Number | Species Structure Species Name |
|---|---|
| 90 | 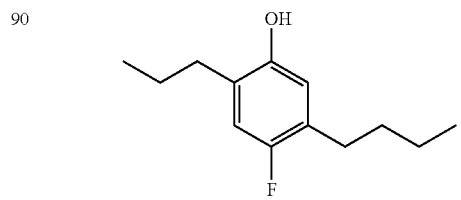<br>5-Butyl-4-fluoro-2-propyl-phenol |
| 91 | 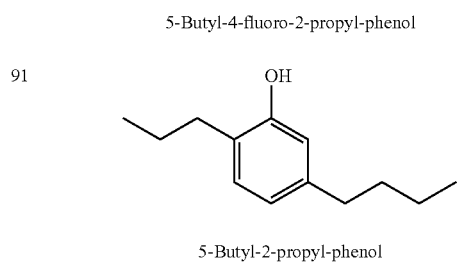<br>5-Butyl-2-propyl-phenol |
| 92 | 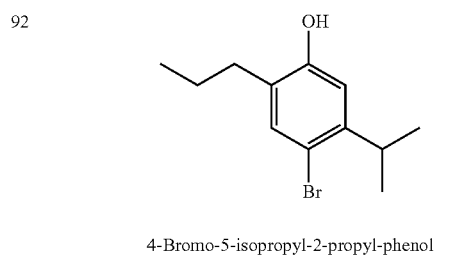<br>4-Bromo-5-isopropyl-2-propyl-phenol |
| 93 | 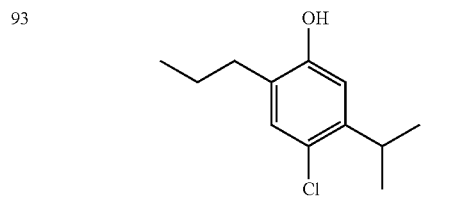<br>4-Chloro-5-isopropyl-2-propyl-phenol |
| 94 | 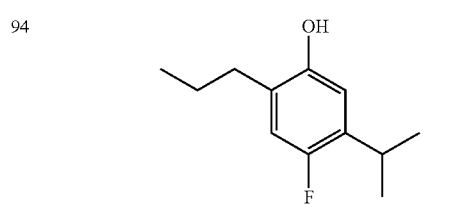<br>4-Fluoro-5-isopropyl-2-propyl-phenol |
| 95 | 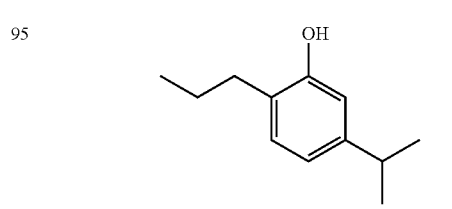<br>5-Isopropyl-2-propyl-phenol |

| Example Number | Species Structure Species Name |
|---|---|
| 96 | 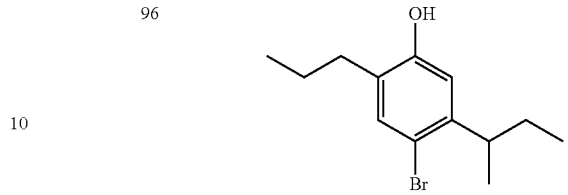<br>4-Bromo-5-sec-butyl-2-propyl-phenol |
| 97 | 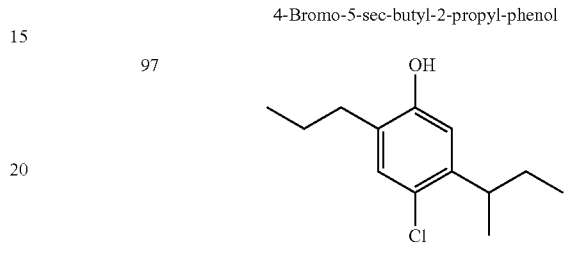<br>5-sec-Butyl-4-chloro-2-propyl-phenol |
| 98 | 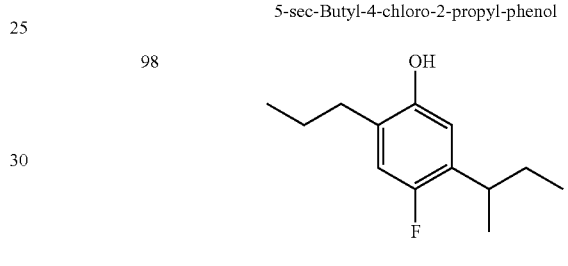<br>5-sec-Butyl-4-fluoro-2-propyl-phenol |
| 99 | 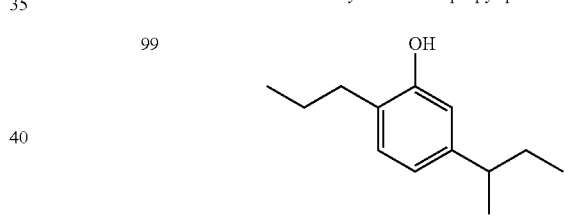<br>5-sec-Butyl-2-propyl-phenol |
| 100 | 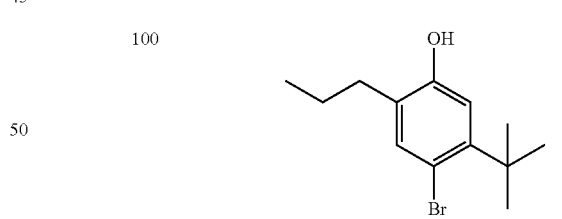<br>4-Bromo-5-tert-butyl-2-propyl-phenol |
| 101 | 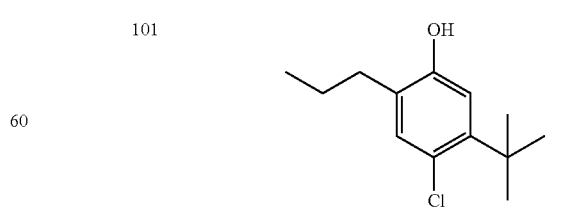<br>5-tert-Butyl-4-chloro-2-propyl-phenol |

| Example Number | Species Structure Species Name |
|---|---|
| 102 | 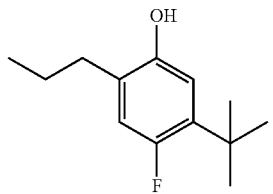 5-tert-Butyl-4-fluoro-2-propyl-phenol |
| 103 | 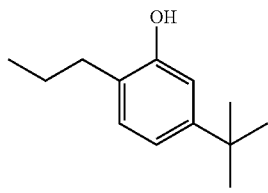 5-tert-Butyl-2-propyl-phenol | n-Butyl series

| Example Number | Species Structure Species Name |
|---|---|
| 104 | 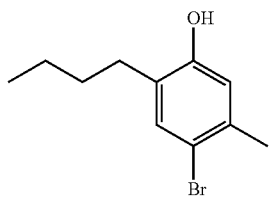 4-Bromo-2-butyl-5-methyl-phenol |
| 105 | 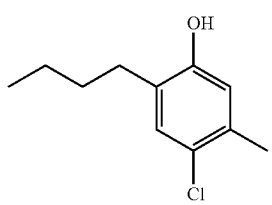 2-Butyl-4-chloro-5-methyl-phenol |
| 106 | 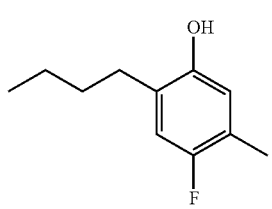 2-Butyl-4-fluoro-5-methyl-phenol |
| 107 | 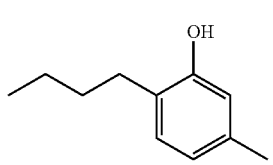 2-Butyl-5-methyl-phenol |

| Example Number | Species Structure Species Name |
|---|---|
| 108 | 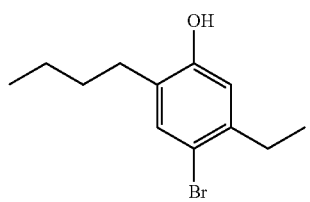 4-Bromo-2-butyl-5-ethyl-phenol |
| 109 | 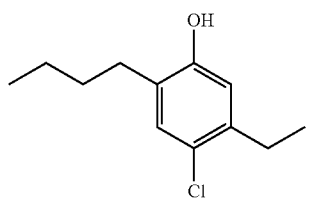 2-Butyl-4-chloro-5-ethyl-phenol |
| 110 | 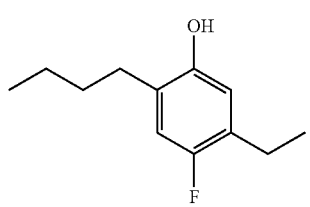 2-Butyl-5-ethyl-4-fluoro-phenol |
| 111 | 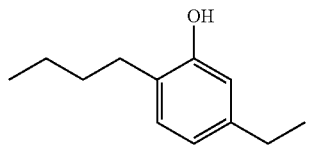 2-Butyl-5-ethyl-phenol |
| 112 | 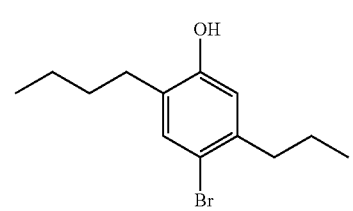 4-Bromo-2-butyl-5-propyl-phenol |
| 113 | 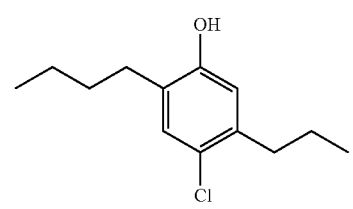 2-Butyl-4-chloro-5-propyl-phenol |

| Example Number | Species Structure Species Name |
|---|---|
| 114 | 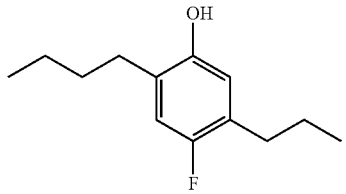<br>2-Butyl-4-fluoro-5-propyl-phenol |
| 115 | 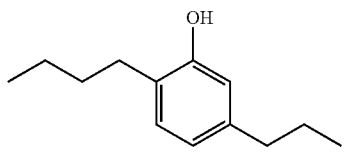<br>2-Butyl-5-propyl-phenol |
| 116 | 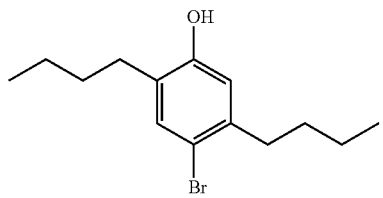 [SMILES: CCCCc1cc(Br)c(CCCC)cc1O]<br>4-Bromo-2,5-dibutyl-phenol |
| 117 | 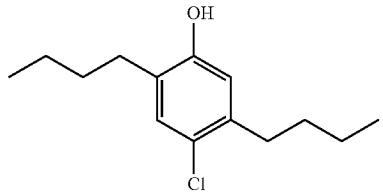<br>2,5-Dibutyl-4-chloro-phenol |
| 118 | 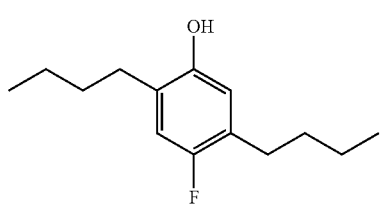 [SMILES: CCCCc1cc(Cl)c(CCCC)cc1O]<br>2,5-Dibutyl-4-fluoro-phenol |
| 119 | 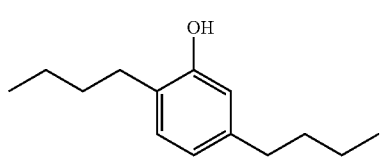<br>2,5-Dibutyl-phenol |
| 120 | 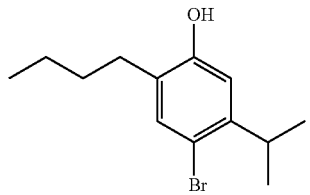<br>4-Bromo-2-butyl-5-isopropyl-phenol |
| 121 | 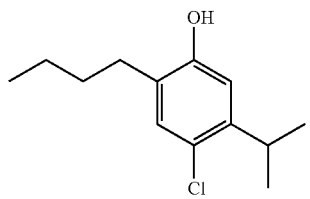<br>2-Butyl-4-chloro-5-isopropyl-phenol |
| 122 | 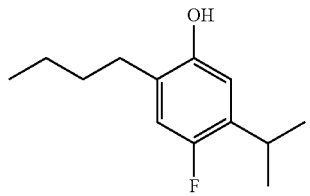<br>2-Butyl-4-fluoro-5-isopropyl-phenol |
| 123 | 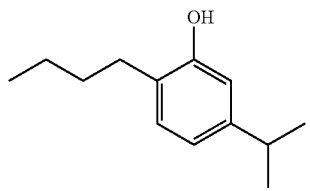<br>2-Butyl-5-isopropyl-phenol |
| 124 | 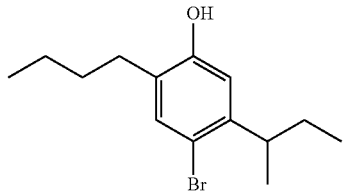<br>4-Bromo-2-butyl-5-sec-butyl-phenol |
| 125 | 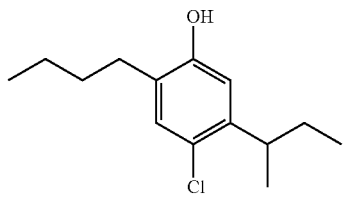 [SMILES: CCCCc1cc(Cl)c(C(C)CC)cc1O]<br>2-Butyl-5-sec-butyl-4-chloro-phenol |

| Example Number | Species Structure Species Name |
|---|---|
| 126 | 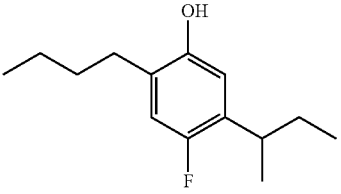 [SMILES: CCCCc1cc(F)c(C(C)CC)cc1O]<br>2-Butyl-5-sec-butyl-4-fluoro-phenol |
| 127 | 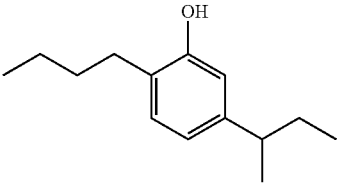<br>2-Butyl-5-sec-butyl-phenol |
| 128 | 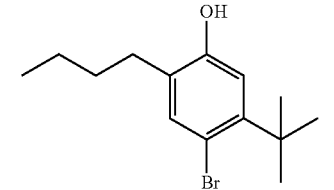 [SMILES: CCCCc1cc(Br)c(C(C)(C)C)cc1O]<br>4-Bromo-2-butyl-5-tert-butyl-phenol |
| 129 | 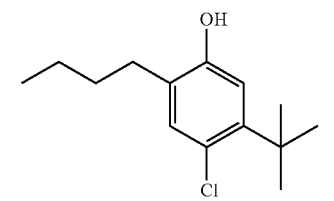<br>2-Butyl-5-tert-butyl-4-chloro-phenol |
| 130 | 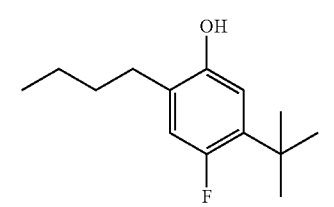 [SMILES: CCCCc1cc(F)c(C(C)(C)C)cc1O]<br>2-Butyl-5-tert-butyl-4-fluoro-phenol |
| 131 | 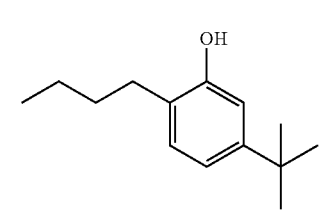 |

| Example Number | Species Structure Species Name |
|---|---|
| Isopropyl Series | |
| 132 | 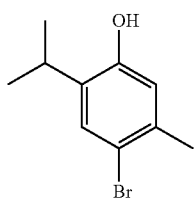<br>4-Bromo-2-isopropyl-5-methyl-phenol |
| 133 | 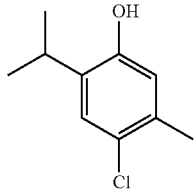<br>4-Chloro-2-isopropyl-5-methyl-phenol |
| 134 | 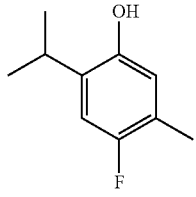<br>4-Fluoro-2-isopropyl-5-methyl-phenol |
| 135 | 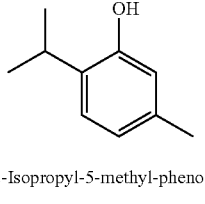<br>2-Isopropyl-5-methyl-phenol |
| 136 | 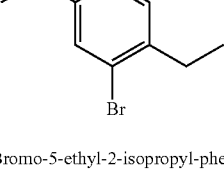<br>4-Bromo-5-ethyl-2-isopropyl-phenol |
| 137 | 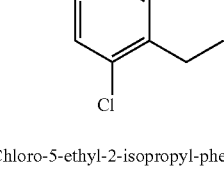<br>4-Chloro-5-ethyl-2-isopropyl-phenol |

| Example Number | Species Structure Species Name |
|---|---|
| 138 | 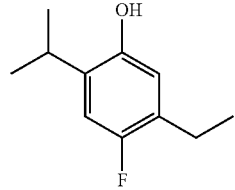 5-Ethyl-4-fluoro-2-isopropyl-phenol |
| 139 | 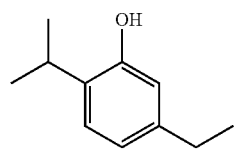 5-Ethyl-2-isopropyl-phenol |
| 140 | 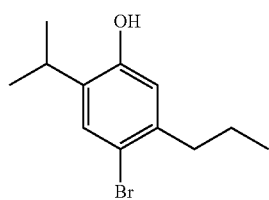 4-Bromo-2-isopropyl-5-propyl-phenol |
| 141 | 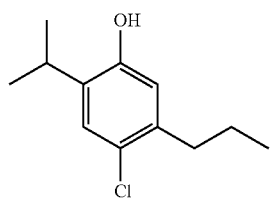 4-Chloro-2-isopropyl-5-propyl-phenol |
| 142 | 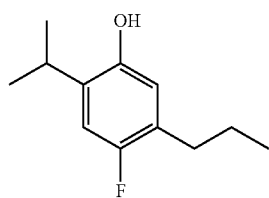 4-Fluoro-2-isopropyl-5-propyl-phenol |
| 143 | 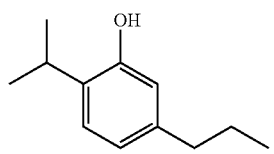 2-Isopropyl-5-propyl-phenol |
| 144 | 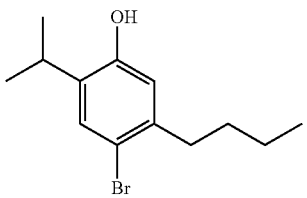 4-Bromo-5-butyl-2-isopropyl-phenol |
| 145 | 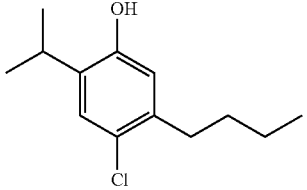 5-Butyl-4-chloro-2-isopropyl-phenol |
| 146 | 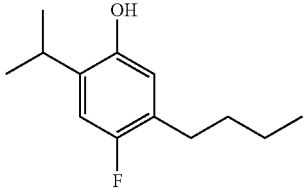 5-Butyl-4-fluoro-2-isopropyl-phenol |
| 147 | 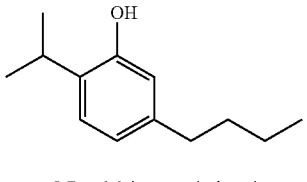 5-Butyl-2-isopropyl-phenol |
| 148 | 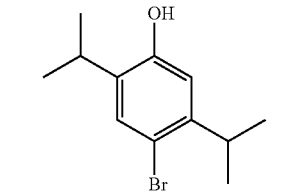 4-Bromo-2,5-diisopropyl-phenol |
| 149 | 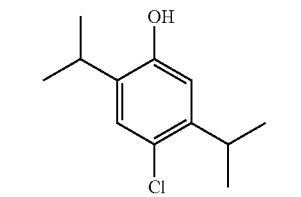 4-Chloro-2,5-diisopropyl-phenol |

| Example Number | Species Structure Species Name |
|---|---|
| 150 | 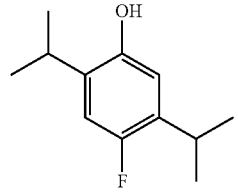<br>4-Fluoro-2,5-diisopropyl-phenol |
| 151 | 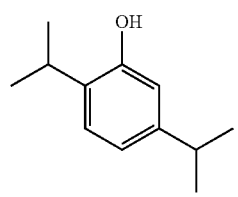<br>2,5-Diisopropyl-phenol |
| 152 | 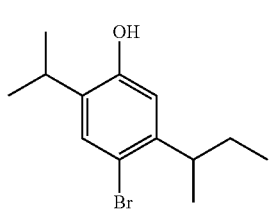<br>4-Bromo-5-sec-butyl-2-isopropyl-phenol |
| 153 | 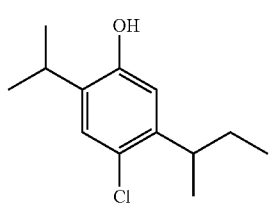<br>5-sec-Butyl-4-chloro-2-isopropyl-phenol |
| 154 | 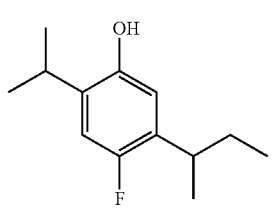<br>5-sec-Butyl-4-fluoro-2-isopropyl-phenol |
| 155 | 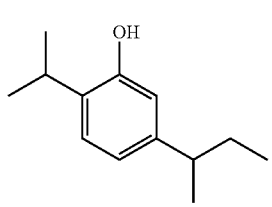<br>5-sec-Butyl-2-isopropyl-phenol |

| Example Number | Species Structure Species Name |
|---|---|
| 156 | 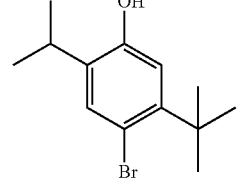<br>4-Bromo-5-tert-butyl-2-isopropyl-phenol |
| 157 | 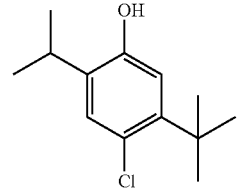<br>5-tert Butyl-4-chloro-2-isopropyl-phenol |
| 158 | 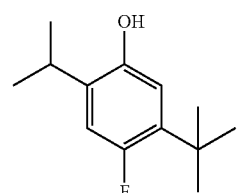<br>5-tert-Butyl-4-fluoro-2-isopropyl-phenol |
| 159 | 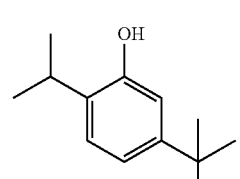<br>5-tert-Butyl-2-isopropyl-phenol |
| Sec-butyl Series | |
| 160 | 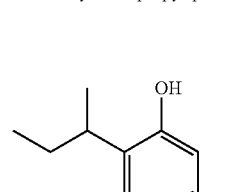<br>4-Bromo-2-sec-butyl-5-methyl-phenol |
| 161 | 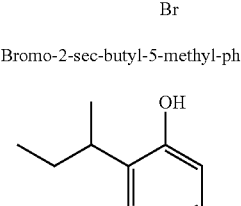<br>2-sec-Butyl-4-chloro-5-methyl-phenol |

| Example Number | Species Structure Species Name |
|---|---|
| 162 | 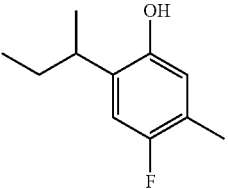<br>2-sec-Butyl-4-fluoro-5-methyl-phenol |
| 163 | 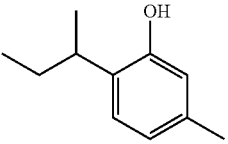<br>2-sec-Butyl-5-methyl-phenol |
| 164 | 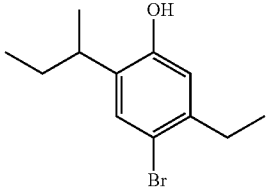<br>4-Bromo-2-sec-butyl-5-ethyl-phenol |
| 165 | 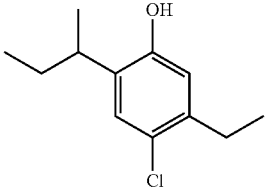<br>2-sec-Butyl-4-chloro-5-ethyl-phenol |
| 166 | 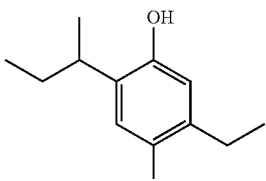<br>2-sec-Butyl-5-ethyl-4-fluoro-phenol |
| 167 | 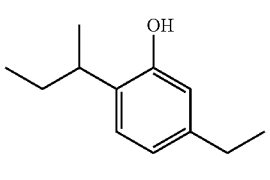<br>2-sec-Butyl-5-ethyl-phenol |
| 168 | 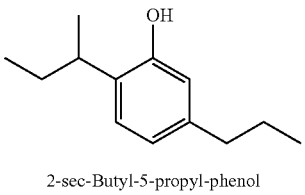<br>2-sec-Butyl-5-propyl-phenol |
| 169 | 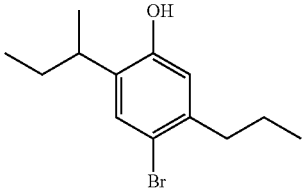<br>4-Bromo-2-sec-butyl-5-propyl-phenol |
| 170 | 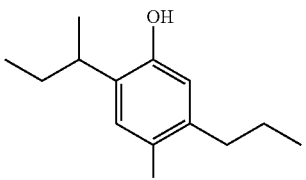<br>2-sec-Butyl-4-chloro-5-propyl-phenol |
| 171 | 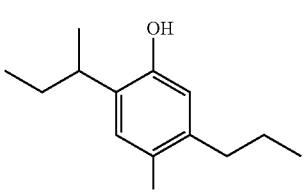<br>2-sec-Butyl-4-fluoro-5-propyl-phenol |
| 172 | 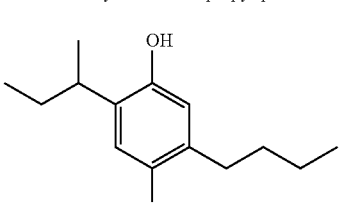<br>4-Bromo-5-butyl-2-sec-butyl-phenol |
| 173 | 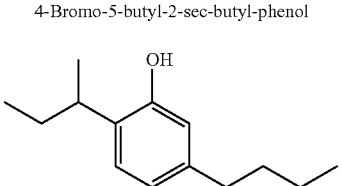<br>5-Butyl-2-sec-butyl-4-chloro-phenol |
| 174 | 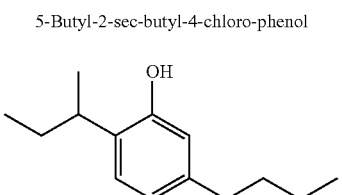<br>5-Butyl-2-sec-butyl-4-fluoro-phenol |

| Example Number | Species Structure Species Name |
|---|---|
| 175 | 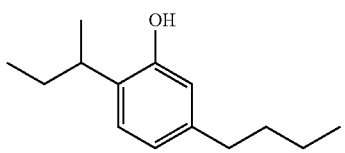<br>5-Butyl-2-sec-butyl-phenol |
| 176 | 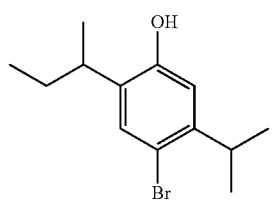<br>4-Bromo-2-sec-butyl-5-isopropyl-phenol |
| 177 | 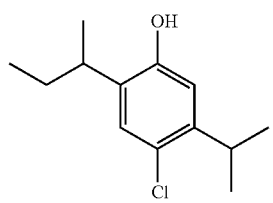<br>2-sec-Butyl-4-chloro-5-isopropyl-phenol |
| 178 | 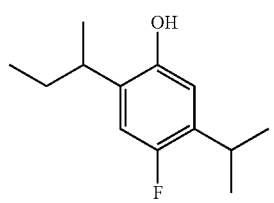<br>2-sec-Butyl-4-fluoro-5-isopropyl-phenol |
| 179 | 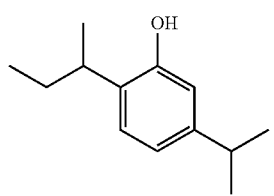<br>2-sec-Butyl-5-isopropyl-phenol |
| 180 | 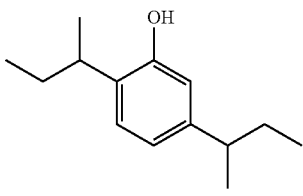<br>2,5-Di-sec-butyl-phenol |
| 181 | 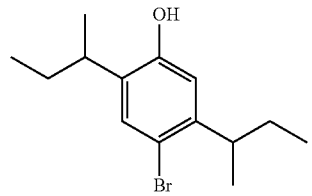 [SMILES: CCC(C)c1cc(Br)c(C(C)CC)cc1O]<br>4-Bromo-2,5-di-sec-butyl-phenol |
| 182 | 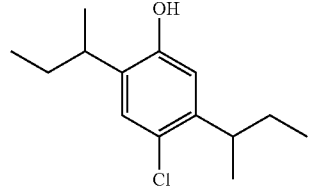<br>2,5-Di-sec-butyl-4-chloro-phenol |
| 183 | 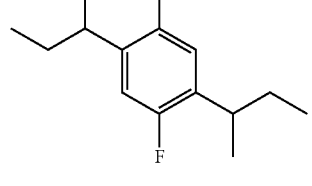<br>2,5-Di-sec-butyl-4-fluoro-phenol |
| 184 | 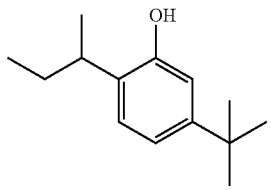<br>2-sec-Butyl-5-tert-butyl-phenol |
| 185 | 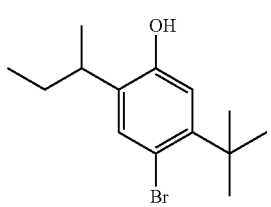 [SMILES: CCC(C)c1cc(Cl)c(C(C)(C)C)cc1O]<br>4-Bromo-2-sec-butyl-5-tert-butyl-phenol |
| 186 | 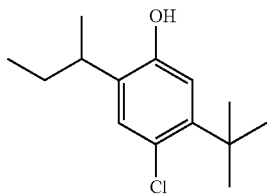<br>2-sec-Butyl-5-tert-butyl-4-chloro-phenol |

| Example Number | Species Structure Species Name |
|---|---|
| 187 | 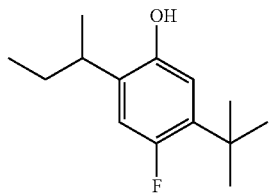 [SMILES: CCC(C)c1cc(F)c(C(C)(C)C)cc1O]<br>2-sec-Butyl-5-tert-butyl-4-fluoro-phenol |
| tert-butyl series | |
| 188 | 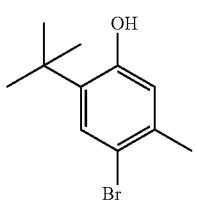<br>4-Bromo-2-tert-butyl-5-methyl-phenol |
| 189 | 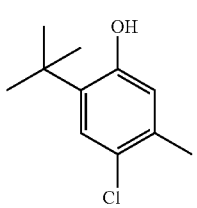<br>2-tert-Butyl-4-chloro-5-methyl-phenol |
| 190 | 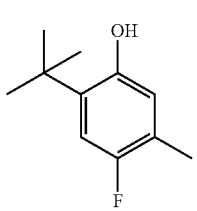<br>2-tert-Butyl-4-fluoro-5-methyl-phenol |
| 191 | 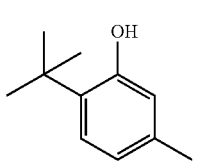<br>2-tert-Butyl-5-methyl-phenol |
| 192 | 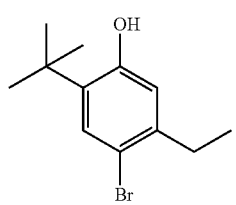<br>4-Bromo-2-tert-butyl-5-ethyl-phenol |
| 193 | 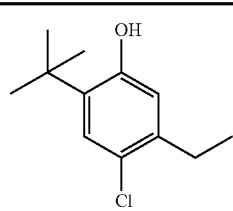<br>2-tert-Butyl-4-chloro-5-ethyl-phenol |
| 194 | 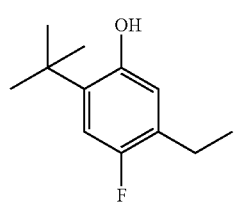<br>2-tert-Butyl-5-ethyl-4-fluoro-phenol |
| 195 | 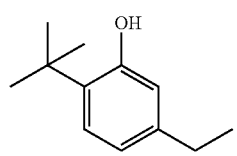<br>2-tert-Butyl-5-ethyl-phenol |
| 196 | 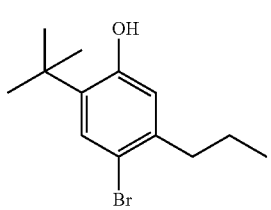<br>4-Bromo-2-tert-butyl-5-propyl-phenol |
| 197 | 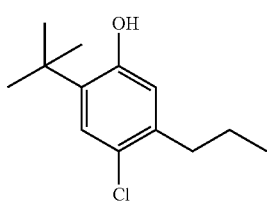<br>2-tert-Butyl-4-chloro-5-propyl-phenol |
| 198 | 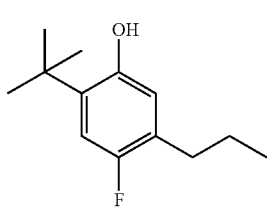<br>2-tert-Butyl-4-fluoro-5-propyl-phenol |

| Example Number | Species Structure Species Name |
|---|---|
| 199 | 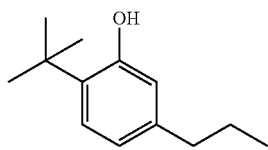<br>2-tert-Butyl-5-propyl-phenol |
| 200 | 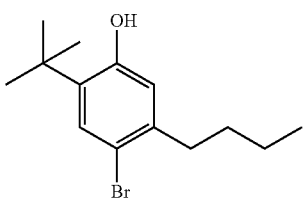<br>4-Bromo-5-butyl-2-tert-butyl-phenol |
| 201 | 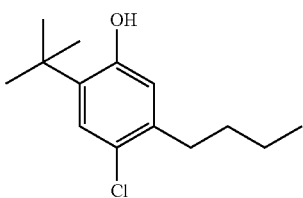 [SMILES: CCCCc1cc(O)c(C(C)(C)C)cc1Cl]<br>5-Butyl-2-tert-butyl-4-chloro-phenol |
| 202 | 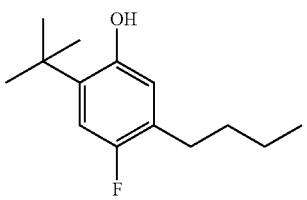 [SMILES: CCCCc1cc(O)c(C(C)(C)C)cc1F]<br>5-Butyl-2-tert-butyl-4-fluoro-phenol |
| 203 | 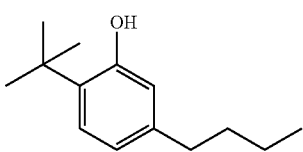<br>5-Butyl-2-tert-butyl-phenol |
| 204 | 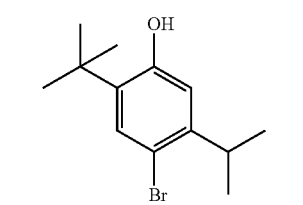<br>4-Bromo-2-tert-butyl-5-isopropyl-phenol |
| 205 | 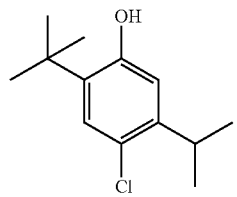<br>2-tert-Butyl-4-chloro-5-isopropyl-phenol |
| 206 | 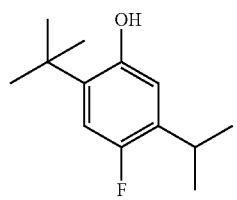<br>2-tert-Butyl-4-fluoro-5-isopropyl-phenol |
| 207 | 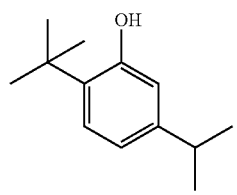<br>2-tert-Butyl-5-isopropyl-phenol |
| 208 | 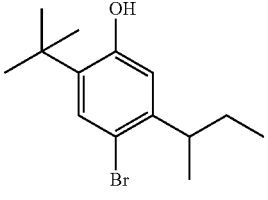 [SMILES: CCC(C)c1cc(O)c(C(C)(C)C)cc1Br]<br>4-Bromo-5-sec-butyl-2-tert-butyl-phenol |
| 209 | 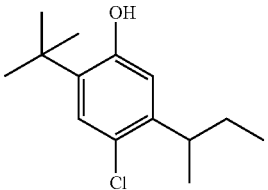<br>5-sec-Butyl-2-tert-butyl-4-chloro-phenol |
| 210 | 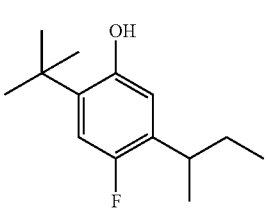 [SMILES: CCC(C)c1cc(O)c(C(C)(C)C)cc1F]<br>5-sec-Butyl-2-tert-butyl-4-fluoro-phenol |

-continued

| Example Number | Species Structure Species Name |
|---|---|
| 211 | 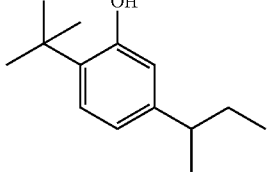<br>5-sec-Butyl-2-tert-butyl-phenol |
| 212 | 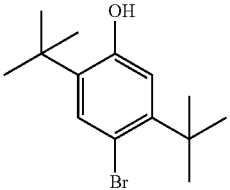 [SMILES: CC(C)(C)c1cc(Br)c(C(C)(C)C)cc1O]<br>4-Bromo-2,5-di-tert-butyl-phenol |
| 213 | 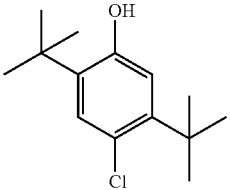 [SMILES: CC(C)(C)c1cc(Cl)c(C(C)(C)C)cc1O]<br>2,5-Di-tert-butyl-4-chloro-phenol |
| 214 | 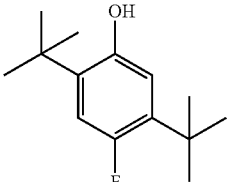<br>2,5-Di-tert-butyl-4-fluoro-phenol |
| 215 | 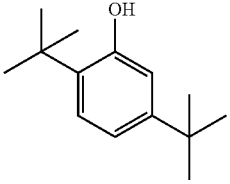<br>2,5-Di-tert-butyl-phenol |
| 5-trifluoro-isopropyl Series | |
| 216 | 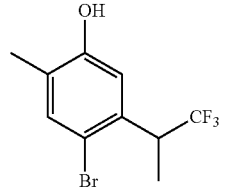<br>4-Bromo-2-methyl-5-(2,2,2-trifluoro-1-methyl-ethyl)-phenol |

-continued

| Example Number | Species Structure Species Name |
|---|---|
| 217 | 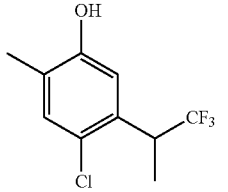<br>4-Chloro-2-methyl-5-(2,2,2-trifluoro-1-methyl-ethyl)-phenol |
| 218 | 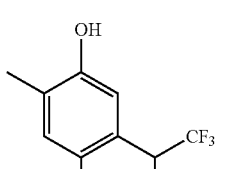<br>4-Fluoro-2-methyl-5-(2,2,2-trifluoro-1-methyl-ethyl)-phenol |
| 219 | 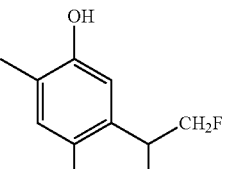<br>2-Methyl-5-(2,2,2-trifluoro-1-methyl-ethyl)-phenol |
| 5-Fluoro-isopropyl series | |
| 220 | 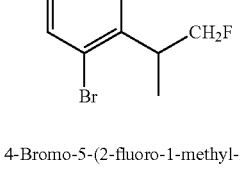<br>4-Bromo-5-(2-fluoro-1-methyl-ethyl)-2-methyl-phenol |
| 221 | 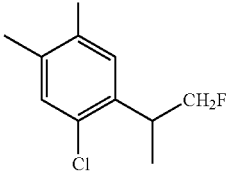<br>4-Chloro-5-(2-fluoro-1-methyl-ethyl)-2-methyl-phenol |

| Example Number | Species Structure Species Name |
|---|---|
| 222 | 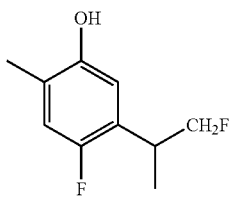<br>4-Fluoro-5-(2-fluoro-1-methyl-ethyl)-2-methyl-phenol |
| 223 | 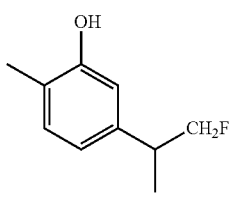<br>5-(2-Fluoro-1-methyl-ethyl)-2-methyl-phenol |
| 5-Hexafluoro-isopropyl series | |
| 224 | 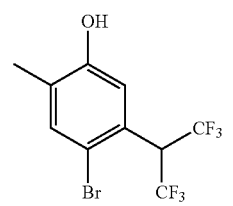<br>4-Bromo-2-methyl-5-(2,2,2-trifluoro-1-trifluoromethyl-ethyl)-phenol |
| 225 | 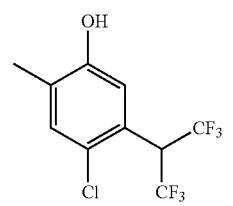 [SMILES: Cc1cc(F)c(C(C(F)(F)F)C(F)(F)F)cc1O]<br>4-Chloro-2-methyl-5-(2,2,2-trifluoro-1-trifluoromethyl-ethyl)-phenol |
| 226 | 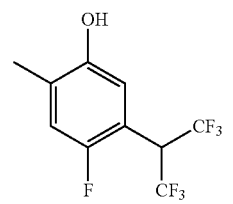<br>4-Fluoro-2-methyl-5-(2,2,2-trifluoro-1-trifluoromethyl-ethyl)-phenol |

| Example Number | Species Structure Species Name |
|---|---|
| 227 | 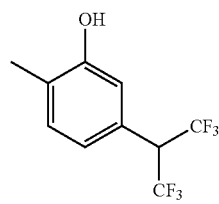 [SMILES: Cc1ccc(C(C(F)(F)F)C(F)(F)F)cc1O]<br>2-Methyl-5-(2,2,2-trifluoro-1-trifluoromethyl-ethyl)-phenol |
| 2-trifluoro Methyl, 5-trifluoro Isopropyl series | |
| 228 | 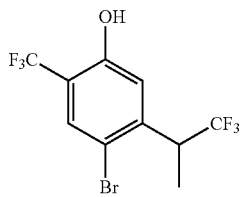 [SMILES: CC(c1cc(O)c(C(F)(F)F)cc1Br)C(F)(F)F]<br>4-Bromo-2-trifluoromethyl-5-(2,2,2-trifluoro-1-methyl-ethyl)-phenol |
| 229 | 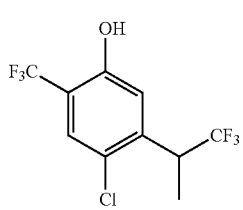 [SMILES: CC(c1cc(O)c(C(F)(F)F)cc1Cl)C(F)(F)F]<br>4-Chloro-2-trifluoromethyl-5-(2,2,2-trifluoro-1-methyl-ethyl)-phenol |
| 230 | 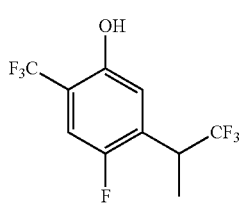 [SMILES: CC(c1cc(O)c(C(F)(F)F)cc1F)C(F)(F)F]<br>4-Fluoro-2-trifluoromethyl-5-(2,2,2-trifluoro-1-methyl-ethyl)-phenol |
| 231 | 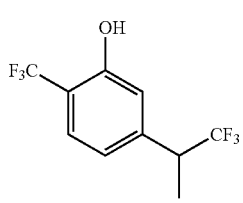<br>2-Trifluoromethyl-5-(2,2,2-trifluoro-1-methyl-ethyl)-phenol |

| Example Number | Species Structure Species Name |
|---|---|
| Sec-pentyl Series | |
| 232 | 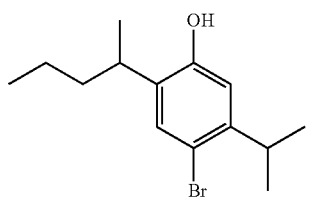 [SMILES: CCCC(C)c1cc(Br)c(C(C)C)cc1O]<br>4-Bromo-5-isopropyl-2-(1-methyl-butyl)-phenol |
| 233 | 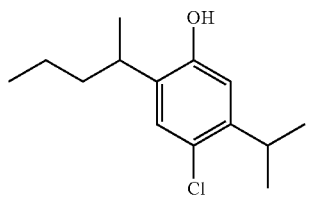 [SMILES: CCCC(C)c1cc(Cl)c(C(C)C)cc1O]<br>4-Chloro-5-isopropyl-2-(1-methyl-butyl)-phenol |
| 234 | 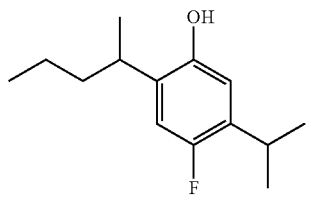 [SMILES: CCCC(C)c1cc(F)c(C(C)C)cc1O]<br>4-Fluoro-5-isopropyl-2-(1-methyl-butyl)-phenol |
| 235 | 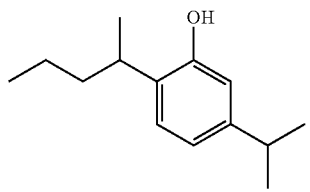<br>5-Isopropyl-2-(1-methyl-butyl)-phenol |
| Isobutyl series | |
| 236 | 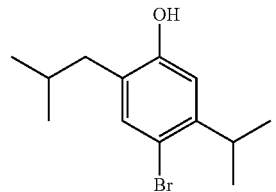<br>4-Bromo-2-isobutyl-5-isopropyl-phenol |
| 237 | 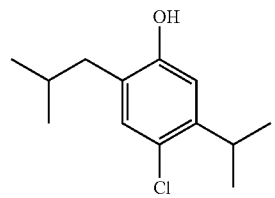<br>4-Chloro-2-isobutyl-5-isopropyl-phenol |

| Example Number | Species Structure Species Name |
|---|---|
| 238 | 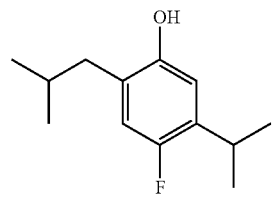<br>4-Fluoro-2-isobutyl-5-isopropyl-phenol |
| 239 | 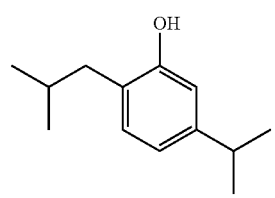<br>2-Isobutyl-5-isopropyl-phenol |
| Cyclopropyl Series | |
| 240 | 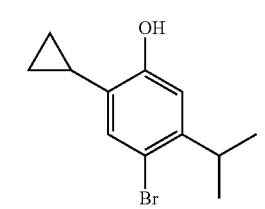<br>4-Bromo-2-cyclopropyl-5-isopropyl-phenol |
| 241 | 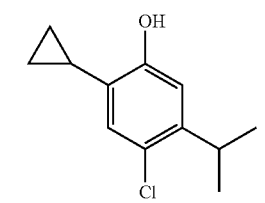<br>4-Chloro-2-cyclopropyl-5-isopropyl-phenol |
| 241 | 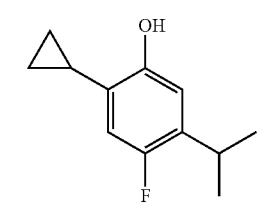<br>2-Cyclopropyl-4-fluoro-5-isopropyl-phenol |
| 242 | 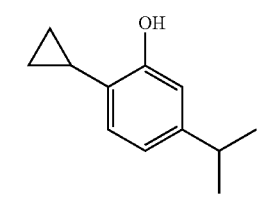<br>2-Cyclopropyl-5-isopropyl-phenol |

| Example Number | Species Structure Species Name |
|---|---|
| Cyclopentyl Series | |
| 243 | 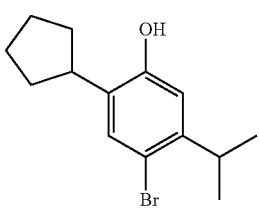 [SMILES: CC(C)c1cc(O)c(C2CCCC2)cc1Br] 4-Bromo-2-cyclopentyl-5-isopropyl-phenol |
| 244 | 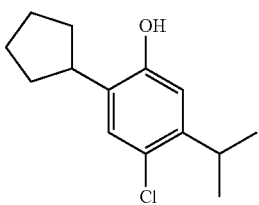 4-Chloro-2-cyclopentyl-5-isopropyl-phenol |
| 245 | 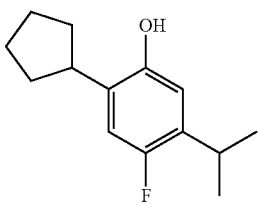 [SMILES: CC(C)c1cc(O)c(C2CCCC2)cc1F] 2-Cyclopentyl-4-fluoro-5-isopropyl-phenol |
| 246 | 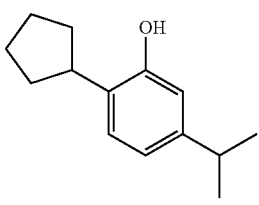 2-Cyclopentyl-5-isopropyl-phenol |
| 2,5-dicyclopropyl Series | |
| 247 | 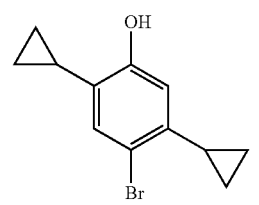 [SMILES: Oc1cc(C2CC2)c(Br)cc1C1CC1] 4-Bromo-2,5-dicyclopropyl-phenol |

| Example Number | Species Structure Species Name |
|---|---|
| 248 | 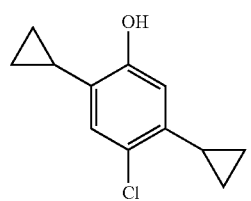 4-Chloro-2,5-dicyclopropyl-phenol |
| 249 | 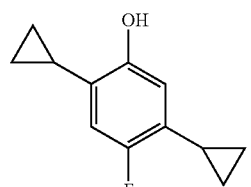 2,5-Dicyclopropyl-4-fluoro-phenol |
| 250 | 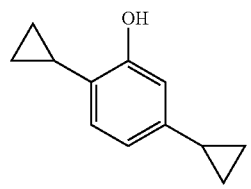 [SMILES: Oc1cc(C2CC2)ccc1C1CC1] 2,5-Dicyclopropyl-phenol |
| 251 | 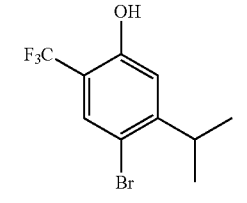 4-Bromo-5-isopropyl-2-trifluoromethyl-phenol |
| 252 | 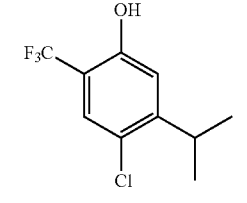 4-Chloro-5-isopropyl-2-trifluoromethyl-phenol |
| 253 | 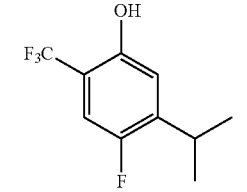 4-Fluoro-5-isopropyl-2-trifluoromethyl-phenol |

| Example Number | Species Structure Species Name |
|---|---|
| 254 | 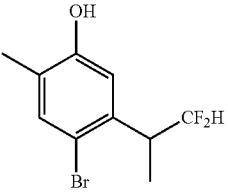<br>4-Bromo-5-(2,2-difluoro-1-methyl-ethyl)-2-methyl-phenol |
| 255 | 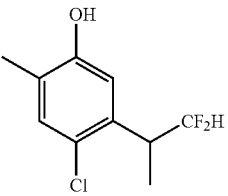<br>4-Chloro-5-(2,2-difluoro-1-methyl-ethyl)-2-methyl-phenol |
| 256 | 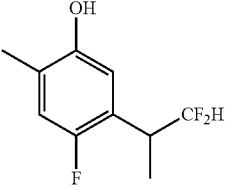<br>5-(2,2-Difluoro-1-methyl-ethyl)-4-fluoro-2-methyl-phenol |

Family 1b Species

| Example Number | Species Structure Species Name |
|---|---|
| 4-trifluormethyl Series (abbreviated) | |
| 257 | 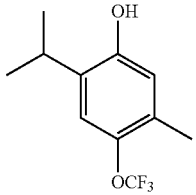 [SMILES: Cc1cc(O)c(C(C)C)cc1OC(F)(F)F]<br>5-Isopropyl-2-methyl-4-trifluoromethoxy-phenol |
| 258 | 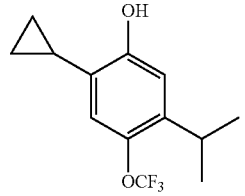 [SMILES: CC(C)c1cc(O)c(C2CC2)cc1OC(F)(F)F]<br>2-Isopropyl-5-methyl-4-trifluoromethoxy-phenol |
| 259 | 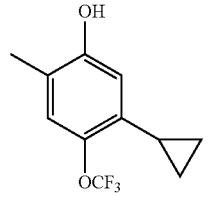 [SMILES: Cc1cc(OC(F)(F)F)c(C2CC2)cc1O]<br>2-Cyclopropyl-5-isopropyl-4-trifluoromethoxy-phenol |
| 260 | 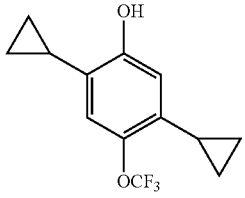<br>5-Cyclopropyl-2-methyl-4-trifluoromethoxy-phenol |
| 261 | 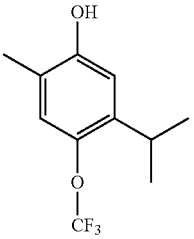<br>2,5-Dicyclopropyl-4-trifluoromethoxy-phenol |
| 4-tert-butyl series | |
| 262 | 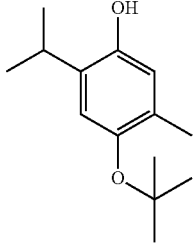 [SMILES: Cc1cc(O)c(C(C)C)cc1OC(C)(C)C]<br>4-tert-Butoxy-2-isopropyl-5-methyl-phenol |

| Example Number | Species Structure Species Name |
|---|---|
| 263 | 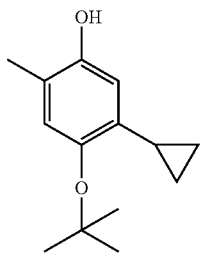 [SMILES: Cc1cc(OC(C)(C)C)c(C2CC2)cc1O]<br>4-tert-Butoxy-5-cyclopropyl-2-methyl-phenol |
| 264 | 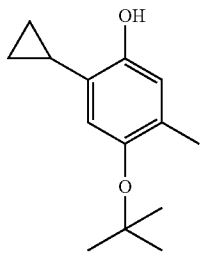 [SMILES: Cc1cc(O)c(C2CC2)cc1OC(C)(C)C]<br>4-tert-Butoxy-2-cyclopropyl-5-methyl-phenol |
| 265 | 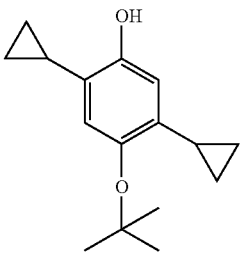 [SMILES: CC(C)(C)Oc1cc(C2CC2)c(O)cc1C1CC1]<br>4-tert-Butoxy-2,5-dicyclopropyl-phenol |
| 4-isopropyl Series (abbreviated) | |
| 266 | 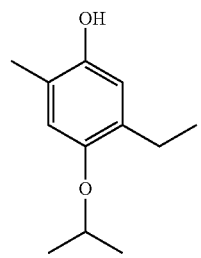<br>5-Ethyl-4-isopropoxy-2-methyl-phenol |

| Example Number | Species Structure Species Name |
|---|---|
| 267 | 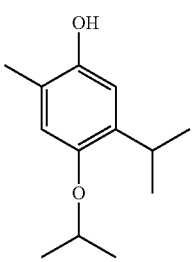<br>4-Isopropoxy-5-isopropyl-2-methyl-phenol |
| 268 | 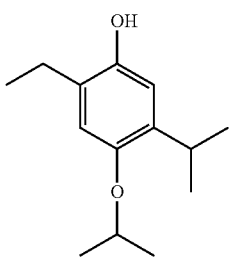<br>2-Ethyl-4-isopropoxy-5-isopropyl-phenol |
| 269 | 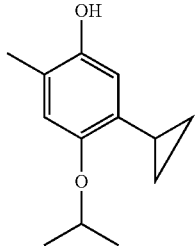<br>5-Cyclopropyl-4-isopropoxy-2-methyl-phenol |
| 270 | 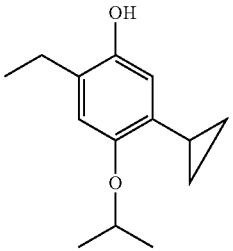 [SMILES: CCc1cc(OC(C)C)c(C2CC2)cc1O]<br>5-Cyclopropyl-2-ethyl-4-isopropoxy-phenol |

| Example Number | Species Structure Species Name |
|---|---|
| 271 | 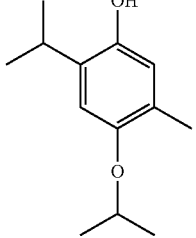<br>4-Isopropoxy-2-isopropyl-5-methyl-phenol |
| 272 | 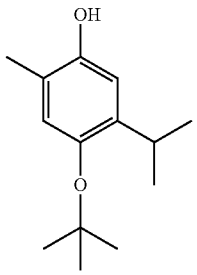 [SMILES: Cc1cc(OC(C)(C)C)c(C(C)C)cc1O]<br>4-tert-Butoxy-5-isopropyl-2-methyl-phenol |

C. Methods of Treatment

The present disclosure further provides methods for treating a condition in a subject having or susceptible to having such a condition, by administering to the subject a therapeutically-effective amount of one or more compounds as described above; such compounds may optionally include one or more deuterium or tritium atoms. In one embodiment, the treatment is preventative treatment. In another embodiment, the treatment is palliative treatment. In another embodiment, the treatment is restorative treatment.

1. Conditions

The conditions that can be treated in accordance with the present invention include, but are not limited to Alzheimer's Disease, anxiety, atherosclerosis, bipolar disorder, celiac sprue, convulsions, dementia, depression, epilepsy, fibromyalgia, glomerulonephritis, Huntington's Chorea, inflammation disorders, inflammatory bowel disease, mania, memory, migraine, multiple sclerosis, neuropathic pain, Parkinson's Disease, pelvic inflammatory disease, rheumatoid arthritis, seizures, tinnitus, Tourette's Syndrome, and tremors. In certain preferred embodiments, the compounds described herein can be administered prophylactically to prevent one or more of the above listed conditions. In particularly preferred embodiments, the compounds described herein can be administered prophylactically to individuals such as soldiers, sailors, biohazard remediation professionals, and the like, who are particularly susceptible to one or more of the above listed conditions as a result of exposure to their work environments.

In certain embodiments, the compounds of the present invention may be administered as adjunctive therapy in the treatment of partial onset seizures in adults and children with epilepsy. In certain embodiments the compounds of the present invention may be administered as adjunctive therapy in the treatment of myoclonic seizures in adults and adolescents with juvenile myoclonic epilepsy. In certain embodiments the compounds of the present invention may be administered as adjunctive therapy in the treatment of primary generalized tonic-clonic seizures in adults and children with idiopathic generalized epilepsy.

The present invention also relates to compounds having microbial-static and microbicidal effects in mammals or on inanimate objects. Compounds of the present invention are useful for sanitizing objects, and therefore are useful for preventing the spread of microorganisms causing infectious disease. Compounds of the present invention are also useful for preserving food, beverage, pharmaceutical and cosmetic preparations at antimicrobial concentrations. They are furthermore useful to prevent and treat infections in mammals, such as the treatment of skin ulcers or periodontal disease, by causing antimicrobial effects on mammalian tissue. In certain embodiments, the compounds of the present invention cause antimicrobial effects while not causing sedation in animals or humans, regardless of whether exposure is deliberate (such as during treatment of a mammalian subject), or inadvertant (such as exposure resulting from application of compounds of the present invention to inanimate objects in the environment of a mammalian subject).

Specifically, the compounds of the present invention can be used to kill or prevent the growth of microorganisms, such as Enterobacteriaceae (such as *Escherichia coli*), Firmicutes (such as *Staphylococcus aureus, Listeria monocytogenes,* and *Bacillus* spp.), Archaebacteria, Protozoans (such as *Giardia lamblia*) and Yeasts (such as *Candida* spp.). Disclosed compounds may be used alone, in combination with other compounds of this invention, or in combination with other substances to cause antimicrobial effects.

2. Subjects

Suitable subjects to be treated according to the present invention include mammalian subjects. Mammals according to the present invention include, but are not limited to, human, canine, feline, bovine, caprine, equine, ovine, porcine, rodents, lagomorphs, primates, including humans, and the like, and encompass mammals in utero. Subjects may be of either gender and at any stage of development, including infancy, childhood, adolescence, young adulthood, adulthood, and senescence.

3. Administration and Dosing

The compounds of the present invention are generally administered in a therapeutically effective amount. The compounds of the present invention may be administered in amounts ranging from about 1 mg to about 100 mg per kilogram of body weight per day, for example about 10 mg/kg, about 20 mg/kg, about 30 mg/kg, about 40 mg/kg, about 50 mg/kg, about 60 mg/kg, about 70 mg/kg, about 80 mg/kg, or about 90 mg/kg per day. The total daily dosage may run from 10 to 1000 mg, such as from 30 to 500 mg, or even from 50 to 250 mg per day. The dosage regimen may be adjusted to provide the optimum therapeutic response and is preferably administered one to three times a day. For example, several divided doses may be administered daily or the dose may be proportionally reduced as indicated by the exigencies of the therapeutic situation. A decided practical advantage is that the active compound may be administered in any convenient manner such as by oral, intraveneous, intramuscular, or subcutaneous routes.

D. Pharmaceutical Compositions

For the treatment of the conditions referred to above, the compounds described herein can be administered as follows:

1. Oral Administration

Oral administration includes pills, tablets, capsules, syrups, powders, tonics, and the like 2. Parenteral Administration Parenteral administration includes enemas, suppositories, and the like.

3. Topical Administration

Topical administration includes lotions, creams, salves, ointments, patches, and the like E. Prodrugs In yet another embodiment, the compounds of the present invention may be synthesized and/or administered as prodrugs. Propofol and certain other phenol containing drugs can have short duration of action in vivo or poor oral absorption by virtue of their susceptibility to extensive first pass metabolism. Prodrugs of propofol have been prepared to increase aqueous solubility for intravenous administration. Methods of making prodrugs are well known in the art (see, e.g., U.S. Pat. No. 6,362,234, US 2011/257587, US 2010/087536, US 2009/005352, US 2006/287525, US 2006/205969, US 2005/234050, US 2005/090431, US 2005/004381, and US 2003/176324, all incorporated by reference in their entireties herein). There are numerous approaches for protecting phenols, including but not limited to the formation of esters, carbonates, phosphates, carbamates, sulfamates, and acylmethylesters. The rate of esterase hydrolysis is known to be highly sensitive to the steric environment about the ester carbonyl. Without being bound by theory, many pro-drugs are designed to take advantage of this fact allowing the release kinetics to be adjusted. Other release mechanisms can be similarly affected by the steric environment.

F. Combinations and Combination Therapy

The compounds of the present invention can be used, alone or in combination with other pharmaceutically active compounds, to treat conditions such as those previously described above. In certain embodiments, a compound according to Formula (I) can be administered simultaneously with a second agent (either in the same dosage form or in separate dosage forms) or sequentially with a second agent. Accordingly, in one embodiment, the present invention comprises methods for treating a condition by administering to the subject a therapeutically-effective amount of one or more compounds according to Formula (I) and one or more additional pharmaceutically active compounds.

In certain non-limiting embodiments, the second agent can comprise one or more anticonvulsants, for example selected from acetylpheneturide, albutoin, aminoglutethimide, 4-amino-3-hydroxybutyric acid, atrolactamide, beclamide, buramate, carbamazepine, cinromide, clomethiazole, clonazepam, decimemide, diethadione, dimethadione, doxenitoin, eterobarb, ethadione, ethosuximide, ethotoin, felbamate, fluoresone, fosphenytoin, gabapentin, ganaxolone, lamotrigine, levetiracetam, lorazepam, mephenyloin, mephobarbital, metharbital, methetoin, methsuximide, midazolam, narcobarbital, nitrazepam, oxcarbazepine, paramethadione, phenacemide, phenetharbital, pheneturide, phenobarbital, phensuximide, phenylmethylbarbituric acid, phenytoin, phenethylate, pregabalin, primidone, progabide, remacemide, rufinamide, suclofenide, sulthiame, talampanel, tetrantoin, tiagabine, topiramate, trimethadione, valproic acid, valpromide, vigabatrin, zonisamide, pharmaceutically acceptable salts thereof, and combinations thereof.

In other non-limiting embodiments, the second agent can comprise an analgesic or anti-inflammatory drug, for example selected from the group consisting of acetaminophen, alfentanil, allylprodine, alphaprodine, anileridine, benzylmorphine, bezitramide, buprenorphine, butorphanol, clonitazene, codeine, cyclazocine, desomorphine, dextromoramide, dextropropoxyphene, dezocine, diampromide, diamorphone, dihydrocodeine, dihydromorphine, dimenoxadol, dimepheptanol, dimethylthiambutene, dioxaphetyl butyrate, dipipanone, dipyrone (metamizol), eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl-morphan, lofentanil, meperidine, meptazinol, metazocine, methadone, metopon, morphine, myrophine, nalbuphine, nalorphine, narceine, nicomorphine, norlevorphanol, normethadone, normorphine, norpipanone, opium, oxycodone, oxymorphone, papavereturn, pentazocine, phenadoxone, phenazocine, phenomorphan, phenoperidine, piminodine, piritramide, proheptazine, promedol, properidine, propiram, propoxyphene, sufentanil, tilidine, tramadol, NO-naproxen, NCX-701, ALGRX-4975, alclometasone, amcinonide, betamethasone, betamethasone 17-valerate, clobetasol, clobetasol propionate, clocortolone, cortisone, dehydrotestosterone, deoxycorticosterone, desonide, desoximetasone, dexamethasone, dexamethasone 21-isonicotinate, diflorasone, fluocinonide, fluocinolone, fluorometholone, flurandrenolide, fluticasone, halcinonide, halobetasol, hydrocortisone, hydrocortisone acetate, hydrocortisone cypionate, hydrocortisone hemisuccinate, hydrocortisone 21-lysinate, hydrocortisone sodium succinate, isoflupredone, isoflupredone acetate, methylprednisolone, methylprednisolone acetate, methylprednisolone sodium succinate, methylprednisolone suleptanate, mometasone, prednicarbate, prednisolone, prednisolone acetate, prednisolone hemisuccinate, prednisolone sodium phosphate, prednisolone sodium succinate, prednisolone valerate-acetate, prednisone, triamcinolone, triamcinolone acetonide, salicylic acid derivatives (such as salicylic acid, acetylsalicylic acid, methyl salicylate, diflunisal, olsalazine, salsalate and sulfasalazine), indole and indene acetic acids (such as indomethacin, etodolac and sulindac), fenamates (such as etofenamic, meclofenamic, mefenamic, flufenamic, niflumic and tolfenamic acids), heteroaryl acetic acids (such as acemetacin, alclofenac, clidanac, diclofenac, fenchlofenac, fentiazac, furofenac, ibufenac, isoxepac, ketorolac, oxipinac, tiopinac, tolmetin, zidometacin and zomepirac), aryl acetic acid and propionic acid derivatives (such as alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), enolic acids (such as the oxicam derivatives ampiroxicam, cinnoxicam, droxicam, lornoxicam, meloxicam, piroxicam, sudoxicam and tenoxicam, and the pyrazolone derivatives aminopyrine, antipyrine, apazone, dipyrone, oxyphenbutazone and phenylbutazone), alkanones (such as nabumetone), nimesulide, proquazone, MX-1094, licofelone, celecoxib, deracoxib, valdecoxib, parecoxib, rofecoxib, etoricoxib, lumiracoxib, PAC-10549, cimicoxib, GW-406381, LAS-34475, CS-502, and pharmaceutically acceptable salts thereof, and combinations thereof.

G. General Synthetic Schemes

The present invention also relates to methods of manufacturing the compounds of the present invention for use in treatment of nervous conditions such as seizure or convulsion disorders. The compounds of the present invention can be prepared using the methods illustrated in the general synthetic schemes and experimental procedures detailed below. These general synthetic schemes and experimental procedures are presented for purposes of illustration and are not intended to be limiting. The starting materials used to prepare the compounds of the present invention are commercially available or can be prepared using routine methods known in the art. Compounds embraced by Formula I may be prepared in accordance with Schemes I-IV, which follow, wherein the R substituent are as defined herein.

Conversion (A): The hydroxy group of 3-bromophenol $I_1$ is protected as a benzyl ether by treating $I_1$ with benzyl bromide (BnBr) and potassium carbonate ($K_2CO_3$) in acetone.

Conversion (B): The benzyl protected bromophenol $I_2$ is then treated with t-BuLi in THF at −78° C. and treated with $R^{5a}CON(OMe)Me$, yielding Scheme I intermediate $I_3$.

Conversion (C): The carbonyl functional group and benzyl ether of intermediate $I_3$ is reduced by subjecting it to hydrogenation conditions to yield Scheme 1 intermediate $I_4$.

Conversion (D): The hydroxy group of 3-bromophenol $I_1$ is protected as a tert-butyl dimethyl silyl ether by treating it

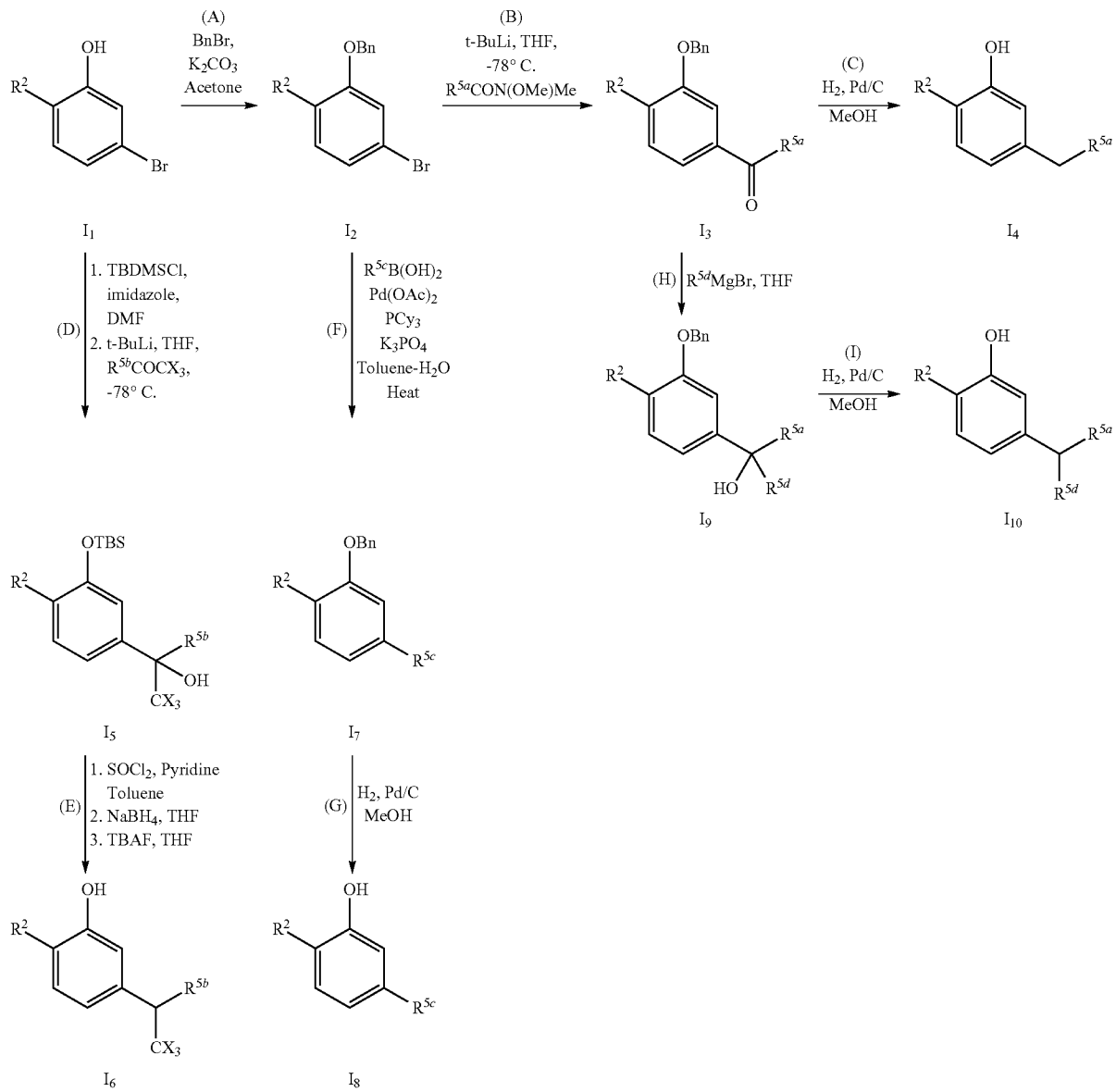

Scheme I $R^2$ = H, Me
$R^{5a}$ = Me, Et, n-Pr, n-Bu, n-Pent, n-hexane
$R^{5b}$ = $CF_3$, $CF_2H$, $CH_2F$
$R^{5c}$ = Cy-propyl, Cy-Bu, Cy-Pent, and Cy-hexane
$R^{5d}$ = Me, Et, n-Pr, n-Bu, n-Pent, n-hexane
X = H or F with TBDMSCl and imidazole in DMF. The silyl ether is then treated with t-BuLi in THF at −78° C. and ketone $R^{5a}COX_3$ to afford the Scheme I intermediate $I_5$.

Conversion (E): Intermediate $I_5$ is treated with thionyl chloride and pyridine to convert the tert-hydroxy group to chloride, which is reduced by treating it with sodium borohydride in THF. In the final step the silyl ether is cleaved by treating it with TBAF in THF to yield Scheme I intermediate $I_6$.

Conversion (F): The Intermediate $I_2$ is subjected to Suzuki coupling with boronic acid $R^{5c}B(OH)_2$, palladium acetate and potassium phosphate to afford the Scheme I intermediate $I_7$.

Conversion (G): The benzyl ether of Intermediate $I_7$ is then cleaved under hydrogenation condition to yield the Scheme I intermediate $I_8$.

Conversion (H): The intermediate $I_3$ is treated with Grignard reagent $R^{5d}MgX$ in THF to afford the Scheme I intermediate $I_9$.

Conversion (I): The tert-hydroxy group and benzyl ether of intermediate $I_9$ is reduced under hydrogenation condition to give the Scheme I intermediate $I_{10}$.

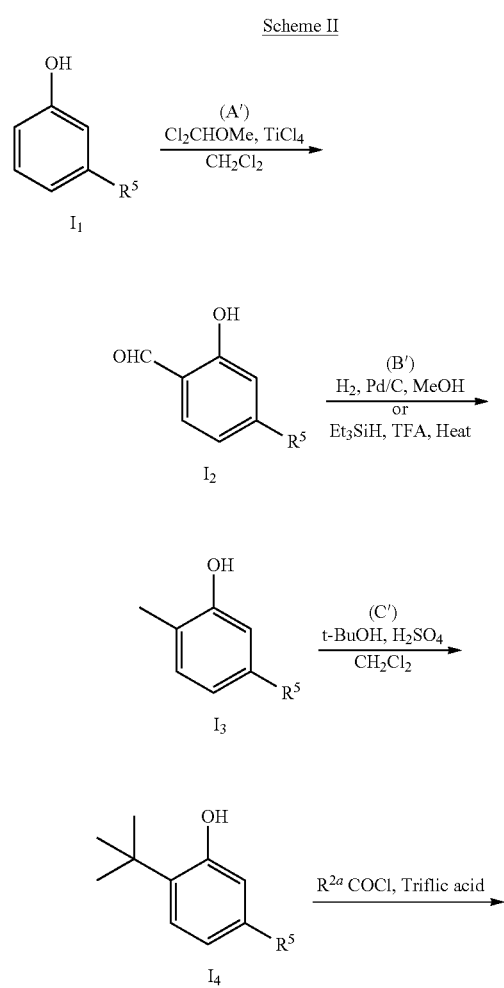

Scheme II

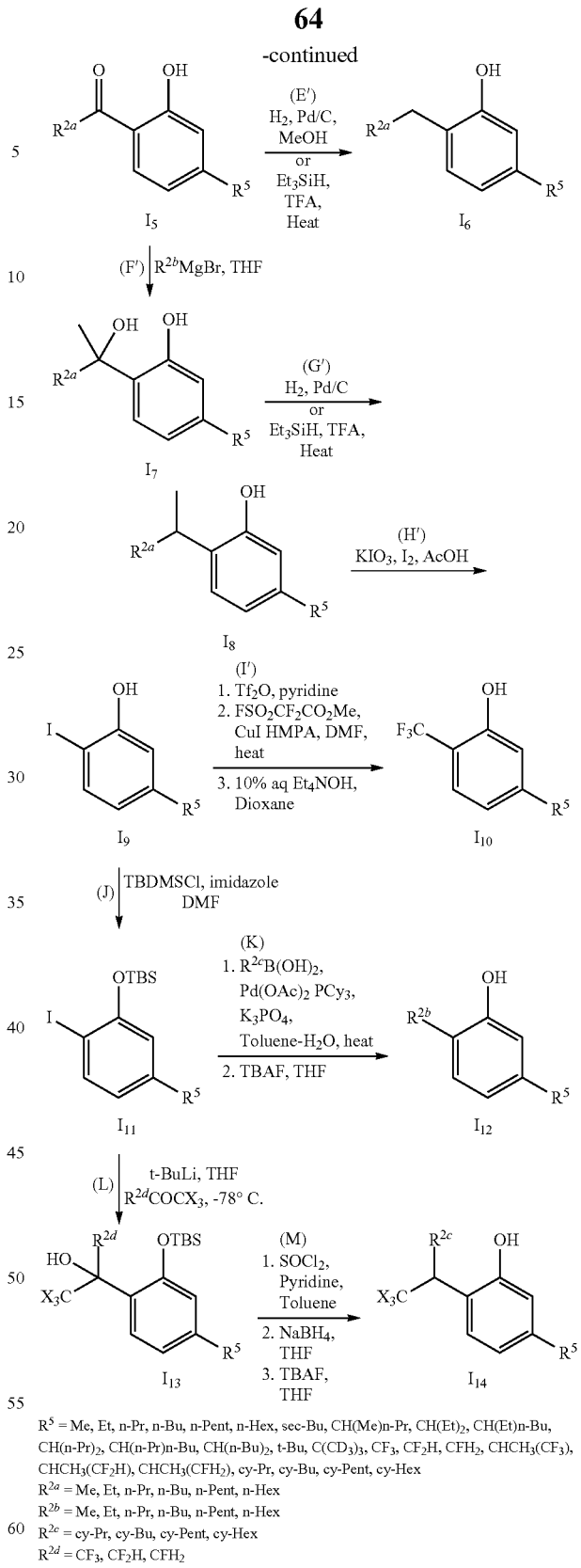

$R^5$ = Me, Et, n-Pr, n-Bu, n-Pent, n-Hex, sec-Bu, CH(Me)n-Pr, CH(Et)$_2$, CH(Et)n-Bu, CH(n-Pr)$_2$, CH(n-Pr)n-Bu, CH(n-Bu)$_2$, t-Bu, C(CD$_3$)$_3$, CF$_3$, CF$_2$H, CFH$_2$, CHCH$_3$(CF$_3$), CHCH$_3$(CF$_2$H), CHCH$_3$(CFH$_2$), cy-Pr, cy-Bu, cy-Pent, cy-Hex
$R^{2a}$ = Me, Et, n-Pr, n-Bu, n-Pent, n-Hex
$R^{2b}$ = Me, Et, n-Pr, n-Bu, n-Pent, n-Hex
$R^{2c}$ = cy-Pr, cy-Bu, cy-Pent, cy-Hex
$R^{2d}$ = CF$_3$, CF$_2$H, CFH$_2$ Conversion (A'): Scheme II intermediate phenol $I_1$ is formylated at 2-position using TiCl$_4$ and dichloromethyl methyl ether in methylene chloride to afford Scheme II intermediate benzaldehyde $I_2$.

Conversion (B'): The formyl group of intermediate benzaldehyde I$_2$ is reduced with either Et$_3$SiH and TFA or under hydrogenation condition to afford the intermediate phenol I$_3$.

Conversion (C'): Scheme II intermediate phenol I$_1$ is treated with tert-butanol in sulfuric acid and acetic acid to give the intermediate phenol I$_4$.

Conversion (D'): Scheme II intermediate phenol I$_1$ is treated with acid chloride R$^{2a}$COCl in trifluoromethane sulfonic acid to afford the intermediate phenol I$_5$.

Conversion (E'): The carbonyl group of Scheme II intermediate I$_5$ is then reduced either with Et$_3$SiH and TFA or hydrogenation condition to yield the intermediate phenol I$_6$.

Conversion (F'): Scheme II intermediate I$_5$ is treated with Grignard reagent R$^{2b}$MgBr in THF to give the intermediate carbinol I$_7$.

Conversion (G'): The tert-hydroxy group of Scheme II intermediate carbinol I$_7$ is then reduced either with Et$_3$SiH and TFA or hydrogenation condition to yield the intermediate phenol I$_8$.

Conversion (H'): Scheme II intermediate phenol I$_1$ is iodinated with iodine and KIO$_3$ in acetic acid to afford the iodinated intermediate phenol I$_9$.

Conversion (I'): Treatment of iodo-phenol, Scheme II intermediate phenol I$_9$ with trifluoromethanesulfonic anhydride and pyridine gives aryl triflate. Reaction of the resultant aryl triflate with FSO$_2$CF$_2$CO$_2$Me and CuI in DMF-HMPA affords trifluoromethylated aryl triflate. The triflate ester is hydrolyzed with 10% aqueous Et$_4$NOH in dioxane to afford Scheme II intermediate, 2-trifluoromethyl phenol I$_{10}$.

Conversion (J): Scheme II intermediate, iodo-phenol I$_9$ on treatment with TBDMSCl and imidazole in DMF protects the phenol hydroxy as tert-butyl dimethyl silyl ether, intermediate I$_{11}$.

Conversion (K): Scheme II intermediate I$_{11}$ under goes Suzuki coupling with R$^{2c}$B(OH)$_2$, palladium acetate, PCy$_3$, potassium phosphate in toluene and water at 100° C. The silyl ether of the Suzuki coupled product is cleaved with TBAF in THF to give Scheme II intermediate phenol I$_{12}$.

Conversion (L): Intermediate I$_{11}$ on treatment with t-BuLi in THF at −78° C. and ketone R$^{2d}$COCX$_3$ gives the tert-carbinol intermediate I$_{13}$.

Conversion (M): The tert-hydroxy group of intermediate I$_{13}$ is transformed to its chloride on treatment with thionyl chloride and pyridine. The chloro derivative is then reduced on treatment with sodium borohydride. Finally, the silyl ether is cleaved with TBAF in THF to afford Scheme II intermediate phenol I$_{14}$.

Scheme III

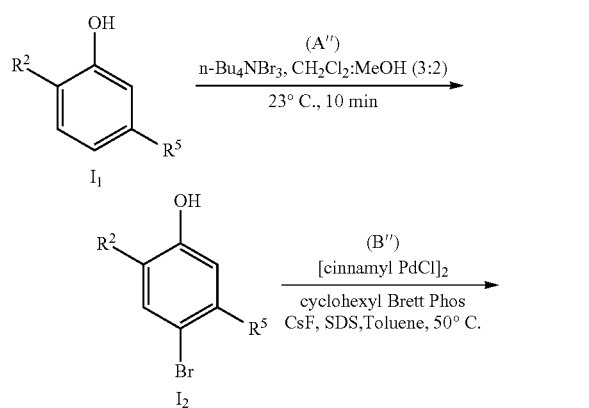

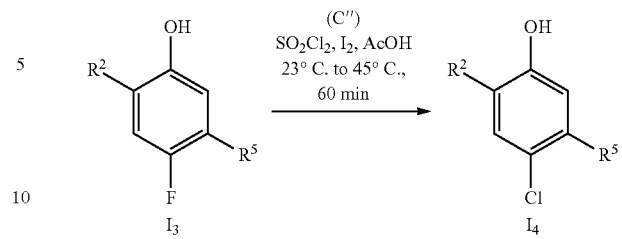

R$^2$ = Me, Et, n-Pr, n-Bu, n-Pent, n-Hex, sec-Bu, CH(Me)n-Pr, CH(Et)$_2$, CH(Et)n-Bu, CH(n-Pr)$_2$, CH(n-Pr)n-Bu, CH(n-Bu)$_2$, t-Bu, C(CD$_3$)$_3$, CF$_3$, CHCH$_3$(CF$_3$), CHCH$_3$(CF$_2$H), CHCH$_3$(CFH$_2$), cy-Pr, cy-Bu, cy-Pent, Cy-Hex R$^5$ = Me, Et, n-Pr, n-Bu, n-Pent, n-Hex, sec-Bu, CH(Me)n-Pr, CH(Et)$_2$, CH(Et)n-Bu, CH(n-Pr)$_2$, CH(n-Pr)n-Bu, CH(n-Bu)$_2$, t-Bu, C(CD$_3$)$_3$, CF$_3$, CF$_2$H, CHCH$_3$(CF$_3$), CHCH$_3$(CF$_2$H), CHCH$_3$(CFH$_2$), cy-Pr, cy-Bu, cy-Pent, Cy-Hex Conversion (A"): Scheme III, intermediate phenol I$_1$ on treatment with n-Bu$_4$NBr$_3$ in a (3:2) mixture of methylene chloride and methanol affords the 4-bromo phenol I$_2$.

Conversion (B"): Scheme III intermediate phenol I$_2$ on palladium catalyzed transformation with [cinnamyl PdCl]$_2$, cyclohexyl Brett Phos, CsF, and sodium dodecyl sulfate (SDS) in toluene at 50° C. affords the 4-fluoro phenol I$_3$.

Conversion (C"): Scheme III intermediate phenol I$_1$ on treatment with sulfuryl chloride and catalytic amount of iodine in acetic acid at 45° C. affords the 4-chloro-phenol I$_4$.

Scheme IV

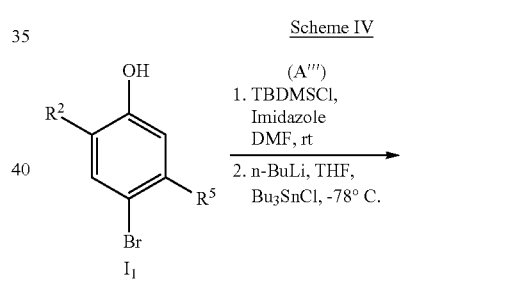

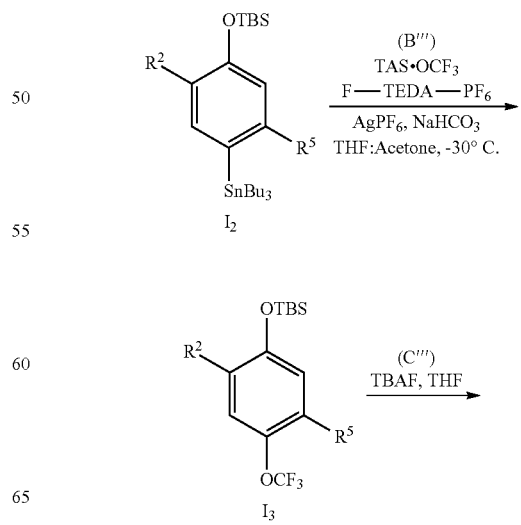

-continued

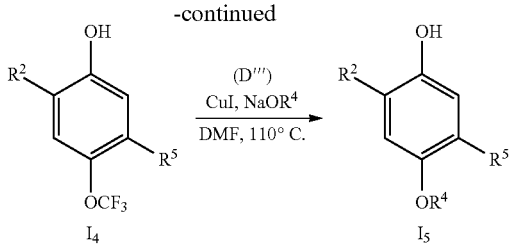

$R^2$ = Me, Et, n-Pr, n-Bu, n-Pent, n-Hex, sec-Bu, CH(Me)n-Pr, CH(Et)$_2$, CH(Et)n-Bu, CH(n-Pr)$_2$, CH(n-Pr)n-Bu, CH(n-Bu)$_2$, t-Bu, C(CD$_3$)$_3$, CF$_3$, CHCH$_3$(CF$_3$), CHCH$_3$(CF$_2$H), CHCH$_3$(CFH$_2$), cy-Pr, cy-Bu, cy-Pent, Cy-Hex $R^4$ = Me, Et, n-Pr, sec-Bu, t-Bu, i-Pr $R^5$ = Me, Et, n-Pr, n-Bu, n-Pent, n-Hex, sec-Bu, CH(Me)n-Pr, CH(Et)$_2$, CH(Et)n-Bu, CH(n-Pr)$_2$, CH(n-Pr)n-Bu, CH(n-Bu)$_2$, t-Bu, C(CD$_3$)$_3$, CF$_3$, CF$_2$H, CFH$_2$, CHCH$_3$(CF$_3$), CHCH$_3$(CF$_2$H), CHCH$_3$(CFH$_2$), cy-Pr, cy-Bu, cy-Pent, Cy-Hex Conversion A''': The hydroxy group of Scheme IV intermediate phenol I$_1$ is protected as tert-butyl dimethyl silyl ether by treating it with TBDMSCl and imidazole in DMF. The intermediate silyl ether is treated with nBuLi in THF at −78° C. followed by Bu$_3$SnCl to afford 4-tributylstannane phenol, intermediate I$_2$.

Conversion B''': Silver mediated coupling of aryl tributylstannane I$_2$ with tris dimethyl ammonium sulfonium trifluoromethoxide (TAS.OCF$_3$) at −30° C. in THF:acetone to afford Scheme IV 4-trifluoromethoxy aryl silyl ether, intermediate I$_3$.

Conversion C''': The silyl ether of intermediate I$_3$ is cleaved by treating it with TBAF in THF to afford 4-trifluoromethoxy phenol, Scheme IV intermediate I$_4$.

Conversion D''': Scheme I intermediate 4-bromo phenol I$_1$ on treatment with CuI and sodium alkoxide in DMF at 110° C., affords the 4-alkoxy phenol I$_5$.

G. Compound Prep Examples

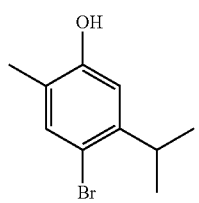

4-Bromo-5-isopropyl-2-methylphenol (9)

4-Bromo-5-isopropyl-2-methylphenol (9): As outlined in Scheme III, conversion A'', 4-bromo-5-isopropyl-2-methylphenol was obtained from commercially available 5-isopropyl-2-methylphenol (Carvacrol, Sigma Aldrich). Accordingly, 5-isopropyl-2-methylphenol (Carvacrol, Sigma Aldrich) (2 gm, 13.31 mmol) was dissolved in 80 mL of CH$_2$Cl$_2$:MeOH (3:2). To this solution was added drop wise a solution of n-Bu$_4$NBr$_3$ in 66 mL of CH$_2$Cl$_2$:MeOH (3:2). The reaction was stirred at room temperature for 10 minutes. The solvent was then removed under vacuo and the residue was dissolved in ether (100 mL), which was then washed with water (3×50 mL). It was dried over anhydrous sodium sulfate, filtered, concentrated and purified by column chromatography using hexanes and ethyl acetate to afford the title compound 2.8 g (93%) as an light yellow oil, which crystallized on prolonged standing at room temperature. $^1$H NMR (400 MHz, CDCl$_3$, ppm): δ 7.25 (s, 1H), 6.68 (s, 1H), 4.62 (s, 1H), 3.24 (sep, J=6.8 Hz, 1H), 2.17 (s, 3H), 1.18 (d, J=7.2 Hz, 6H).

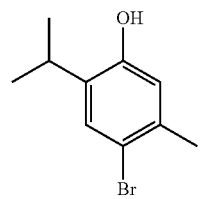

4-Bromo-2-isopropyl-5-methylphenol (132)

4-Bromo-2-isopropyl-5-methylphenol (132): Compound 132 was synthesized from 2-isopropyl-5-methylphenol (Thymol, Sigma Aldrich), following the procedure used for the synthesis of compound 9. $^1$H NMR (400 MHz, CDCl$_3$, ppm): δ 7.28 (s, 1H), 6.66 (s, 1H), 4.60 (s, 1H), 3.22 (sep, J=6.8 Hz, 1H), 2.14 (s, 3H), 1.19 (d, J=7.2 Hz, 6H).

4-Bromo-2-tert-butyl-5-isopropyl phenol (204)

4-Bromo-2-tert-butyl5-isopropylphenol (204): Compound 204 was synthesized from 5-isopropyl phenol in accordance to (a) Scheme II conversion C', and (b) Scheme III conversion A''. Scheme II Conversion C' . . . Synthesis of 2-tert-Butyl-5-isopropyl phenol: As outlined in Scheme II, conversion C', to a solution of 5-isopropyl phenol (2.5 g, 18.37 mmol, TCI US) in CH$_2$Cl$_2$ (25 mL) at 0° C. was added tert-butanol (1.76 mL, 18.35 mmol) and concentrated sulfuric acid (0.98 mL, 18.35 mmol). The reaction was allowed to warm to room temperature and stirred for 24 hour. The mixture was poured on to ice-water (50 mL) and quenched with NaHCO$_3$. The organic layer was removed and the aqueous layer was extracted with CH$_2$Cl$_2$ (3×50 mL). The combine organic extract was dried over anhydrous sodium sulfate, filtered, and concentrated in vacuo. The residue was purified by column chromatography using hexanes and ethyl acetate, giving 3 g (86%) of the desired phenol as an oil. $^1$H NMR (400 MHz, CDCl$_3$, ppm): δ 7.20 (d, J=8.1 Hz, 1H), 6.76 (dd, J=8.1, 1.8 Hz, 1H), 6.54 (d, J=1.8 Hz, 1H), 4.71 (s, 1H), 2.83 (sept, J=6.9 Hz, 1H), 1.41 (s, 9H), 1.24 (d, J=6.9 Hz, 6H). Scheme III Conversion A'' . . . Synthesis of 4-Bromo-2-tert-butyl5-isopropylphenol: Compound 204 was synthesized from 2-tert-butyl-5-isopropyl phenol obtained above, following the procedure adopted for the synthesis of compound 9. $^1$H NMR (400 MHz, CDCl$_3$, ppm): δ 7.39 (s, 1H), 6.60 (s, 1H), 4.41 (s, 1H), 3.26 (sep, J=6.8 Hz, 1H), 1.35 (s, 9H), and 1.18 (d, J=7.2 Hz, 6H).

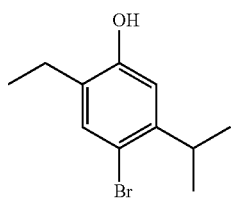

4-Bromo-2-ethyl-5-isopropyl phenol (64)

4-Bromo-2-ethyl-5-isopropyl phenol (64): Compound 64 was synthesized from 3-isopropyl phenol in accordance to (a) Scheme II Conversion D' and E', and (b) Scheme III Conversion A". Scheme II Conversion D' . . . Synthesis of 1-(2-Hydroxy-4-isopropyl-phenyl) ethanone: A solution of 3-isopropyl phenol (2 g, 14.68 mmol) and acetyl chloride (1.05 mL, 14.68 mmol) in 10 mL of triflic acid was stirred at room temperature for 16 h. The reaction mixture was poured on to ice-cold water and extracted with EtOAc. The organic layer was washed with 1 N HCl, saturated NaHCO$_3$, and brine solution. The organic layer was dried over anhydrous Na$_2$SO$_4$, filtered, and concentrated under vacuo. The residue was purified by column chromatography using hexanes and ethyl acetate to afford 2 gm (77%) of the title compound as an yellow oil. $^1$H NMR (400 MHz, CDCl$_3$, ppm): δ 12.26 (s, 1H), 7.63 (d, J=8.4 Hz, 1H), 6.82 (d, J=1.6 Hz, 1H), 6.75 (dd, J=8.4 Hz, 1.6 Hz, 1H), 2.87 (sep, J=7.2 Hz, 1H), 2.58 (s, 3H), and 1.23 (d, J=6.8 Hz, 6H). Scheme II Conversion E' . . . Synthesis of 2-Ethyl-5-isopropyl phenol: To a solution of 1-(2-Hydroxy-4-isopropyl-phenyl) ethanone (1.5 g, 8.41 mmol) in TFA (4 mL) at 0° C. was added Et$_3$SiH (6.72 mL, 42.05 mmol) drop wise. The reaction mixture was heated at 55° C. for 36 h. The reaction mixture was allowed to cool to room temperature and water (50 mL) and CH$_2$Cl$_2$ (50 mL) were added. The aqueous layer was separated and extracted with CH$_2$Cl$_2$ (3×50 mL). The combined organic extracts were washed with brine and dried over anhydrous Na$_2$SO$_4$, filtered, and concentrated under vacuo. The residue was purified by column chromatography using hexanes and ethyl acetate to afford 1.2 g (87%) the title phenol as a yellow oil. $^1$H NMR (400 MHz, CDCl$_3$, ppm): δ 7.03 (d, J=7.6 Hz, 1H), 6.74 (dd, J=7.6 Hz, 1.6 Hz), 6.64 (d, J=1.6 Hz), 2.80 (sep, J=7.2 Hz), 2.58 (q, J=8.0 Hz, 2H), 1.21 (t, J=8.0 Hz, 3H), and 1.20 (d, J=6.8 Hz, 6H). Scheme III Conversion A' . . . Synthesis of 4-Bromo-2-ethyl-5-isopropyl phenol (64): Compound 64 was synthesized from 2-ethyl-5-isopropyl phenol obtained above, following a procedure adopted for the synthesis of compound 9. $^1$H NMR (400 MHz, CDCl$_3$, ppm): δ 7.27 (s, 1H), 6.69 (s, 1H), 4.65 (s, 1H), 3.25 (sep, J=6.8 Hz, 1H), 3.37 (q, J=7.2 Hz, 2H), 1.21 (t, J=7.6 Hz, 3H), and 1.20 (d, J=7.2 Hz, 6H).

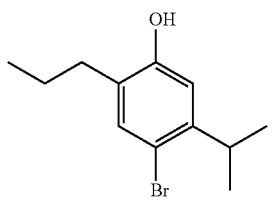

4-Bromo-5-isopropyl-2-n-propyl phenol (92)

4-Bromo-5-isopropyl-2-n-propyl phenol: Compound 92 was synthesized from 3-isopropyl phenol following the procedure adopted for the synthesis of compound 64. In the first step, propionyl chloride was used instead of acetyl chloride. 1-(2-Hydroxy-4-isopropyl-phenyl) propan-1-one: $^1$H NMR (400 MHz, CDCl$_3$, ppm): δ 12.37 (s, 1H), 7.68 (d, J=8.0 Hz, 1H), 6.84 (d, J=2.0 Hz, 1H), 6.76 (dd, J=8.0 Hz, 1.6 Hz, 1H), 3.00 (q, J=7.6 Hz, 2H), 2.88 (sep, J=6.8 Hz, 1H), and 1.23 (m, 9H). 2-n-Propyl-5-isopropyl phenol: $^1$H NMR (400 MHz, CDCl$_3$, ppm): δ 7.03 (d, J=7.6 Hz, 1H), 6.74 (dd, J=7.6 Hz, 1.6 Hz, 1H), 6.64 (d, J=1.6 Hz, 1H), 2.83 (sep, J=7.2 Hz, 1H), 2.54 (t, J=7.6 Hz, 2H), 1.63 (m, 2H), 1.22 (d, J=6.8 Hz, 6H), and 0.98 (t, J=7.2 Hz, 3H). 4-Bromo-5-isopropyl-2-n-propyl phenol: $^1$H NMR (400 MHz, CDCl$_3$, ppm): δ 7.25 (s, 1H), 6.68 (s, 1H), 4.60 (s, 1H), 3.25 (sep, J=6.8 Hz, 1H), 2.50 (t, J=7.6 Hz, 2H), 1.62 (m, 2H), 1.20 (d, J=6.8 Hz, 6H), and 0.97 (t, J=7.2 Hz, 3H).

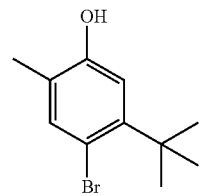

4-Bromo-5-tert-butyl-2-methyl phenol (25)

4-Bromo-5-tert-butyl-2-methyl phenol (25): Compound 25 was synthesized from commercially available 3-tert-butyl phenol in accordance to (a) Scheme II Conversion A' and B', and (b) Scheme III Conversion A". Scheme II Conversion A' . . . Synthesis of 4-tert-Butyl-2-hydroxy benzaldehyde: To a solution of 3-tert-butyl phenol (4 g, 26.62 mmol) in anhydrous CH$_2$Cl$_2$ (50 mL) at 0° C. was added TiCl$_4$ (5.85 mL, 53.24 mmol), followed by Cl$_2$CHOMe (4.82 mL, 53.23 mmol). The reaction mixture was allowed to warm to room temperature over 1 h, quenched cautiously with ice and water. It was then extracted with CH$_2$Cl$_2$ (3×50 mL). The organic extract was washed with water and brine, dried over anhydrous Na$_2$SO$_4$, filtered, and concentrated in vacuo. The residue was purified by column chromatography using hexanes and ethyl acetate to afford 3.5 g (74%) of the title compound as an yellow oil. $^1$H NMR (400 MHz, CDCl$_3$, ppm): δ 11.98 (s, 1H), 9.83 (s, 1H), 7.46 (d, J=8.4 Hz), 7.04 (dd, J=8.4 Hz, 2.0 Hz, 1H), 6.99 (d, J=1.6 Hz, 1H), and 1.30 (s, 9H). Scheme II Conversion B' . . . Synthesis of 5-tert-Butyl-2-methyl phenol: To a solution of 4-tert-butyl-2-hydroxy benzaldehyde (1.9 g, 10.66 mmol) in TFA (5 mL) at 0° C. was added Et$_3$SiH (20.4 mL, 128.0 mmol) drop wise. The reaction mixture was stirred at room temperature for 8 h. Water (50 mL) and CH$_2$Cl$_2$ (50 mL) are added. The aqueous layer is separated and extracted with CH$_2$Cl$_2$ (3×50 mL). The combined organic extracts is washed with brine and dried over anhydrous Na$_2$SO$_4$, filtered, and concentrated under vacuo. The residue was purified by column chromatography using hexanes and ethyl acetate to afford 1.5 g (85%) the title phenol as an yellow oil. $^1$H NMR (400 MHz, CDCl$_3$, ppm): δ 7.03 (d, J=8.0 Hz, 1H), 6.86 (dd, J=7.6 Hz, 1.6 Hz, 1H), 6.80 (d, J=1.6 Hz, 1H), 4.56 (s, 1H), 2.20 (s, 1H), and 1.27 (s, 9H). Scheme III Conversion A" . . . Synthesis of 4-Bromo-5-tert-butyl-2-methyl phenol (25): Compound 25 was synthesized from 5-tert-butyl-2-methyl phenol, obtained above, following the procedure adopted for the synthesis of compound 9. ¹H NMR (400 MHz, CDCl₃, ppm): δ 7.32 (s, 1H), 6.86 (s, 1H), 4.63 (s, 1H), 2.17 (s, 3H), and 1.47 (s, 9H).

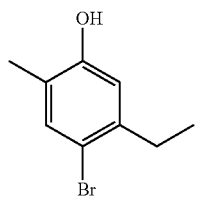

4-Bromo-5-ethyl-2-methyl phenol (5)

4-Bromo-5-ethyl-2-methyl phenol (5): Compound 5 is synthesized from commercially available 5-bromo-2-methyl phenol in accordance to (a) Scheme I Conversion A, B, and C, and Scheme III Conversion A". Scheme I Conversion A: As outlined in Scheme I, conversion A, benzyl bromide (1 equivalent) is added to a suspension of 5-bromo-2-methyl phenol (1 equivalent) and potassium carbonate (2 equivalents) in acetone. The reaction mixture is stirred at room temperature. After completion of the reaction, the mixture is filtered, concentrated, and the residue is purified by column chromatography to yield the phenol protected as its benzyl ether, Scheme I intermediate I₂. Scheme I Conversion B: Intermediate I₂ (1 equivalent) is dissolved in anhydrous THF and cooled to −78° C. To this cold solution tert-BuLi (1 equivalent) is added drop wise and the reaction is stirred for 30 minutes. N-methoxy-N-methyl-acetamide (1.2 equivalents) is then added drop wise and the reaction is allowed to warm to room temperature. After completion of reaction, the reaction mixture is quenched with dil HCl and extracted with ethylacetate. The organic extracts are dried over anhydrous sodium sulfate, and concentrated in vacuo. The residue is purified by column chromatography to give intermediate I₃. Scheme I Conversion C: A suspension Intermediate I₃ and catalytic amount of 5% Pd/C in methanol under hydrogen atmosphere is stirred for 12 hours. The reaction mixture is carefully filtered over a plug of Celite and the solvent is removed in vacuo. The residue is purified by column chromatography to yield the 5-ethyl-2-methyl phenol, Scheme I intermediate I₄. Scheme III conversion A": The intermediate I₄, obtained above is brominated at 4-position using n-BuNBr₃ in a mixture of CH₂Cl₂:MeOH (3:2), following the procedure described for the synthesis of compound 9 to obtain compound 5.

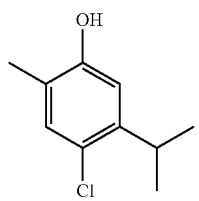

4-Chloro-5-isopropyl-2-methyl phenol (10)

4-Chloro-5-isopropyl-2-methyl phenol (10): Compound 10 is synthesized from Carvacrol in accordance to the method outlined in Scheme III, conversion C". Accordingly to a solution of Carvacrol (1 equivalent) in acetic acid is added few crystals of iodine. Sulfuryl chloride (1.5 equivalent) is then added drop wise to the reaction mixture and the mixture is then heated at 45° C. for 60 minutes. The reaction mixture is cooled to room temperature and partitioned between CH₂Cl₂ and water. The organic layer is washed with water until the aqueous pH is neutral. The organic layer is dried over anhydrous sodium sulfate, filtered, and concentrated in vacuo. The residue is purified by column chromatography to afford the compound 10.

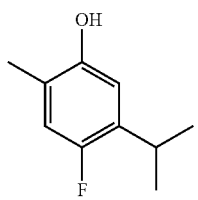

4-Fluoro-5-isopropyl-2-methyl phenol (11)

4-Fluoro-5-isopropyl-2-methyl phenol (11): As outlined in Scheme III, conversion B", compound 11 is derived from compound 9. Accordingly, compound 9 (1 equivalent), ligand cyclohexyl Brett Phos (0.1 equivalent), [cinnamylP-dCl]₂ (0.02 equivalent), CsF (1.5 equivalent) is added to a suspension of sodium dodecyl sulfate (60 equivalent) in toluene. The reaction mixture is then agitated at 110° C. for 6 hour under argon atmosphere. The reaction mixture is cooled to room temperature. Cetyltrimethylammonium bromide (60 equivalent) and toluene are added to the reaction mixture. The reaction mixture is then agitated for another 10 minutes. The reaction mixture is filtered through a plug of Celite. Filtrate is concentrated under reduced pressure and purified by flash chromatography to give the fluorinated compound 11.

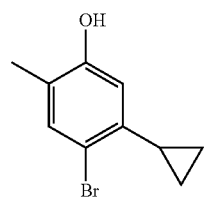

4-Bromo-2-cyclopropyl-5-methyl phenol (41)

4-Bromo-2-cyclopropyl-5-methyl phenol (41): Compound 41 is synthesized from 5-bromo-2-methyl phenol in accordance to (a) Scheme I, conversions A, F and G, and (b) Scheme III, conversion A". Scheme I Conversion F: Accordingly, the Scheme I intermediate I₂ obtained during the synthesis of compound 5 is subjected to Suzuki coupling. A suspension of intermediate I₂ (1 equivalent), cyclopropylboronic acid (1.5 equivalent), K₃PO₄ (3.5 equivalent), PCy₃ (0.1 equivalent), and Pd(OAc)₂ (0.05 equivalent) in toluene-water is stirred for 3 hours at 100° C. The reaction mixture is cooled to room temperature and diluted with ether. The organic layer is washed with water, and brine, dried over anhydrous sodium sulfate, filtered, and concentrated under reduced pressure. The residue is purified by column chromatography to yield cyclopropyl substituted Scheme I intermediate I₇. Scheme I Conversion G: A suspension of intermediate I₇ and catalytic amount of 5% Pd/C in methanol is agitated under hydrogen atmosphere using a hydrogen balloon for 12 hours. The reaction mixture is filtered through a plug of Celite. The filtrate is concentrated under vacuo and the residue is purified by column chromatography to afford the intermediate phenol I₈. Scheme III Conversion A": The intermediate phenol I₈ is brominated at 4-position with nBu₄NBr₃ in CH₂Cl₂:MeOH using a procedure described for the synthesis of compound 9, to afford the compound 41.

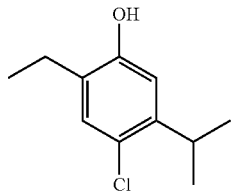

4-Chloro-2-ethyl-5-isopropyl phenol (65)

4-Chloro-2-ethyl-5-isopropyl phenol (65): Compound 65 is derived from intermediate phenol, 2-ethyl-5-isopropyl phenol obtained during the synthesis of compound 64, according to the procedure described for the synthesis of compound 10.

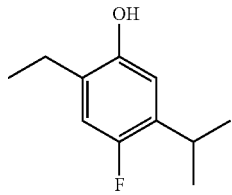

2-Ethyl-4-fluoro-5-isopropyl phenol (66)

2-Ethyl-4-fluoro-5-isopropyl phenol (66): Compound 66 is derived from compound 64, according to the procedure described for the synthesis of compound 11.

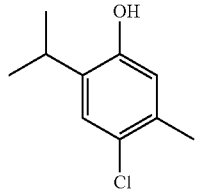

4-Chloro-5-isopropyl-2-methyl phenol (133)

4-Chloro-5-isopropyl-2-methyl phenol (133): Compound 133 is derived from thymol, according to the procedure described for the synthesis of compound 10.

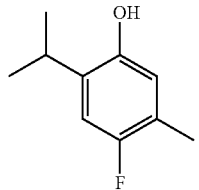

4-Fluoro-2-isopropyl-5-methyl phenol (134)

4-Fluoro-2-isopropyl-5-methyl phenol (134): Compound 134 is derived from compound 132, according to the procedure described for the synthesis of compound 11.

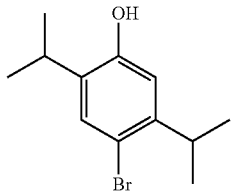

4-Bromo-2,5-diisopropyl phenol (148)

4-Bromo-2,5-diisopropyl phenol (148): Compound 148 is synthesized from 3-isopropyl phenol in accordance to (a) Scheme II, conversion D', F' and G', and (b) Scheme III, conversion A". Scheme II Conversion D': Accordingly, a solution of 3-isopropyl phenol (1 equivalent) and acetyl chloride (1 equivalent) in trifluoromethane sulfonic acid is stirred at room temperature for 6 hours. The reaction mixture is then poured on to ice-water and extracted with ether. The organic layer is dried over sodium sulfate, filtered, and concentrated under vacuo. The residue is purified by column chromatography to afford Scheme II intermediate phenol I₅. Scheme II Conversion F": To a solution of phenol I₅ (1 equivalent) in anhydrous THF at 0° C. is added a solution of methylmagnesium bromide in ether (5 equivalent). The reaction mixture is allowed to warm to room temperature and stirred till the completion of reaction. The reaction mixture is quenched slowly with aqueous NH₄Cl solution then extracted with ether. The organic layer is dried over sodium sulfate, filtered, and concentrated under vacuo. The residue is then purified by column chromatography to afford Scheme II intermediate phenol I₇. Scheme II Conversion G': A suspension of phenol I₇ and catalytic amount of 5% Pd/C in methanol under hydrogen atmosphere is stirred at room temperature for 12 hours, Scheme II, conversion G'. The reaction mixture is filtered through a plug of Celite and the filtrate concentrated under reduced pressure. The residue is purified by column chromatography to afford Scheme II intermediate phenol I₈. Scheme III Conversion A": The intermediate phenol I₈ is brominated at 4-position, according to the procedure described for the synthesis of compound 9, to afford compound 148.

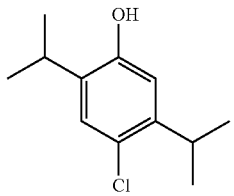

4-Chloro-2,5-diisopropyl phenol (149)

4-Chloro-2,5-diisopropyl phenol (149): Compound 149 is derived from Scheme II intermediate phenol I₈, obtained during the synthesis of compound 148, according to the procedure described for the synthesis of compound 10.

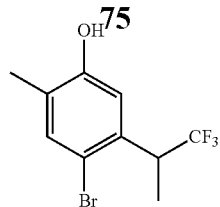
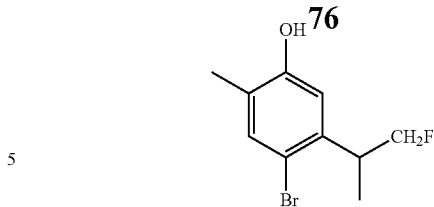

4-Bromo-2-methyl-5-(2,2,2-trifluoro-1-methyl-ethyl)-phenol (216)

4-Bromo-5-(2-fluoro-1-methyl-ethyl)-2-methyl phenol (220)

4-Bromo-2-methyl-5-(2,2,2-trifluoro-1-methyl-ethyl)-phenol (216): Compound 216 is synthesized from commercially available 5-bromo-2-methyl phenol in accordance to (a) Scheme I, conversions D and E, and (b) Scheme III, conversion A". Scheme I conversion D: A solution of 5-bromo-2-methyl-phenol (1 equivalent), imidazole (2 equivalent), and TBDMSCl (1 equivalent) in anhydrous DMF is stirred at room temperature. After the completion of the reaction, the reaction mixture is partitioned between ether and water. The ether layer is washed ice-cold brine, dried over sodium sulfate, filtered, and concentrated under vacuo. The residue is purified by column chromatography to afford the silyl ether. To a solution of silyl ether (1 equivalent) in anhydrous THF at −78° C. is added a solution of t-BuLi in hexane (1.5 equivalent) is added drop wise and the reaction mixture is stirred for 30 minutes at −78° C. $CF_3COCH_3$ (1.5 equivalent) is then added drop wise at −78° C. and the reaction mixture is allowed to warm to room temperature. After the completion of reaction, the reaction is slowly quenched with aqueous ammonium chloride solution. The mixture is then extracted with ether. The ether layer is washed brine, dried over anhydrous sodium sulfate, filtered, and concentrated under vacuo. The residue is purified by column chromatography to afford the Scheme I intermediate phenol $I_5$. Scheme I Conversion E: Thionyl chloride (2 equivalent) is added drop wise to a solution of intermediate phenol $I_5$ (1 equivalent) in toluene and pyridine (few drops) at 0° C. The reaction mixture is allowed to warm to room temperature and stirred for 12 hours. The reaction mixture is poured on to water and extracted with ethyl acetate. The combined ethyl acetate extracts is washed with aqueous $NaHCO_3$ solution, dried over sodium sulfated, filtered, and concentrated under vacuo. The residue is purified by column chromatography to afford the tert-chloro derivative. A suspension of tert-chloro derivative (1 equivalent) and sodium borohydride (15 equivalent) in anhydrous THF is stirred at room temperature. After completion of reaction, the reaction is quenched with water and extracted with ethyl acetate. The combined ethyl acetate layers are dried over sodium sulfate, filtered, and concentrated under vacuo. The residue is purified by column chromatography to afford the de-chlorinated derivative. A solution of the de-chlorinated derivative (1 equivalent) and TBAF (5 equivalent) in THF is stirred at room temperature. After completion of reaction, the solvent is removed under vacuo. The residue is dissolved in water and extracted with ethyl acetate. The combine organic extract is dried over sodium sulfate, filtered, and concentrated. The residue is purified by column chromatography to yield the Scheme I intermediate phenol $I_6$. Scheme III, Conversion A": The intermediate phenol $I_6$ is brominated at 4-position according to the procedure described for the synthesis of compound 9, to afford compound 216.

4-Bromo-5-(2-fluoro-1-methyl-ethyl)-2-methyl phenol (220): Compound 220 is derived from 5-bromo-2-methyl phenol according to the procedure described for the synthesis of compound 216, using $CH_2FCOCH_3$ instead of $CH_3COCF_3$ in the second step of the synthesis.

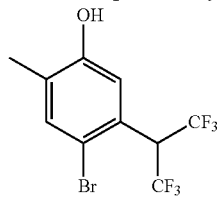

4-Bromo-2-methyl-5-(2,2,2-trifluoro-1-trifluoromethyl-ethyl)-phenol (224)

4-Bromo-2-methyl-5-(2,2,2-trifluoro-1-trifluoromethyl-ethyl)-phenol (224):

Compound 224 is derived from 5-bromo-2-methyl phenol according to the procedure described for the synthesis of compound 216, using $CF_3COCF_3$ instead of $CH_3COCF_3$ in the second step of the synthesis.

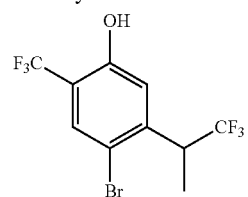

4-Bromo-2-trifluoromethyl-5-(2,2,2-trifluoro-1-methyl-ethyl)-phenol (228)

4-Bromo-2-trifluoromethyl-5-(2,2,2-trifluoro-1-trifluoromethyl-ethyl)-phenol (228): Compound 228 is synthesized from commercially available 3-bromo-phenol in accordance to (a) Scheme I, conversion D and E, (b) Scheme II, conversion H' and I', (c) Scheme III, conversion A". Scheme I Conversions D and E: Scheme I intermediate phenol $I_6$ is synthesized from 3-bromo phenol, according to the procedure described for the synthesis of an analogous intermediate, used for the synthesis of compound 216. Scheme II conversion H': A mixture of intermediate phenol $I_6$ (1 equivalent), $KIO_3$ (0.2 equivalent), iodine (0.5 equivalent) in acetic acid is stirred at room temperature for 3 days. The solvent is removed under vacuo. The residue is dissolved in ether and washed with aqueous $NaHCO_3$, $Na_2S_2O_3$, and brine. The organic layer is dried over anhydrous sodium sulfate, filtered, and concentrated under vacuo. The residue is purified by column chromatography to yield the Scheme II intermediate iodinated phenol $I_9$.

Scheme II conversion I': Triflic anhydride (1 equivalent) is added drop wise to an ice cooled solution of 3-iodo phenol derivative (1 equivalent) and Et₃N (2 equivalent) in CH₂Cl₂. The reaction mixture is allowed to warm to room temperature. After completion of reaction, the reaction mixture is diluted with CH₂Cl₂ and washed with water. The organic layer is dried over anhydrous sodium sulfate, filtered, and concentrated under vacuo. The residue is purified by flash column chromatography to yield the triflate. A solution of aryl triflate (1 equivalent), FSO₂CF₂CO₂Me (5 equivalent), HMPA (5 equivalent), and CuI (1.2 equivalent) in DMF is stirred at 70° C. After completion of reaction, the reaction mixture is cooled to room temperature. A saturated aqueous solution of NH₄Cl is added and the reaction mixture is extracted with ether. The organic layer is washed with aqueous NaHCO₃ and brine, and dried over sodium sulfate. The solvent is removed under vacuo. The residue was purified by column chromatography to afford the 3-trifluoromethyl substituted intermediate aryl triflate. To a solution of aryl trifate (1 equivalent) in dioxane is added 10% aqueous Et4NOH solution (2 equivalent) at room temperature and the reaction is stirred till completion of reaction. The reaction mixture is diluted with CHCl₃, washed with 1M HCl, water, and brine. The organic layer is dried over anhydrous sodium sulfate and concentrated under vacuo. The residue is purified by column chromatography to afford Scheme II intermediate phenol I₁₀. Scheme III conversion A": Phenol I₁₀ is brominated at 4-position according to the procedure described for the synthesis of compound 9, to afford compound 228.

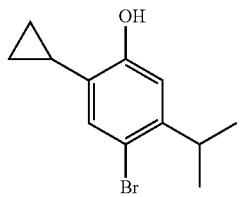

4-Bromo-2-cyclopropyl-5-isopropyl phenol (240)

4-Bromo-2-cyclopropyl-5-isopropyl phenol (240): Compound 240 is synthesized from commercially available 3-isopropyl phenol in accordance to (a) Scheme II, conversion H', J, and K, and (b) Scheme III, conversion A". Scheme II Conversion H': 3-Isopropyl phenol is iodinated according to the procedure described for the synthesis of an analogous intermediate phenol I₉, used in the synthesis of compound 228. Scheme II Conversion J: A solution of 3-iodo-5-isopropyl phenol (1 equivalent), imidazole (2 equivalent), and TBDMSCl (1 equivalent) in anhydrous DMF is stirred at room temperature. After the completion of the reaction, the reaction mixture is partitioned between ether and water. The ether layer is washed ice-cold brine, dried over sodium sulfate, filtered, and concentrated under vacuo. The residue is purified by column chromatography to afford the silyl ether, Scheme II intermediate I₁ⱼ. Scheme II Conversion K: A suspension of intermediate I₁₁ (1 equivalent), cyclopropylboronic acid (1.5 equivalent), K₃PO₄ (3.5 equivalent), PCy₃ (0.1 equivalent), and Pd(OAc)₂ (0.05 equivalent) in toluene-water is stirred for 3 hours at 100° C. The reaction mixture is cooled to room temperature and diluted with ether. The organic layer is washed with water, and brine, dried over sodium sulfate, filtered, and concentrated under reduced pressure. The residue is purified by column chromatography to yield 3-cyclopropyl substituted intermediate.

A solution of above intermediate (1 equivalent) and TBAF (5 equivalent) in THF is stirred at room temperature. After completion of reaction, the solvent is removed under vacuo. The residue is dissolved in water and extracted with ethyl acetate. The combine organic extract is dried over anhydrous sodium sulfate, filtered, and concentrated in vacuo. The residue is purified by column chromatography to yield the Scheme II intermediate phenol I₁₂. Scheme III Conversion A": Phenol I₁₂ is brominated at 4-position according to the procedure described for the synthesis of compound 9, to afford compound 240.

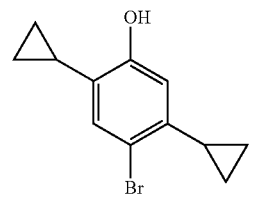 [SMILES: Oc1cc(C2CC2)c(Br)cc1C1CC1]

4-Bromo-2,5-dicyclopropyl phenol (247)

4-Bromo-2,5-dicyclopropyl phenol (247): Compound 247 is synthesized from commercially available 3-bromo phenol in accordance to (a) Scheme I Conversion A, F and G, (b) Scheme II, conversion H', J, and K, and (c) Scheme III, conversion A". Scheme I Conversion A, F, and G: The intermediate 3-cyclopropy phenol is synthesized according to the procedure described for the synthesis of Scheme I intermediate, 5-cyclopropyl-2-methyl phenol I₈, obtained during the synthesis of compound 41. Scheme II, conversion H', J, and K: The intermediate 2,5-dicyclopropyl phenol is synthesized from 3-cyclopropyl phenol according to the procedure described for the synthesis of Scheme II intermediate phenol I₁₂, obtained during the synthesis of compound 240. Scheme III conversion A": 2,5-dicyclopropyl phenol is brominated at 4-position according to the procedure described for the synthesis of compound 9, to afford compound 247.

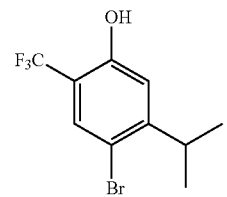

4-Bromo-5-isopropyl-2-trifluoromethyl phenol (266)

4-Bromo-5-isopropyl-2-trifluoromethyl phenol (266): Compound 266 is synthesized from commercially available 3-isopropyl phenol according to the procedure described for the synthesis of compound 228, starting from Scheme II conversion H'.

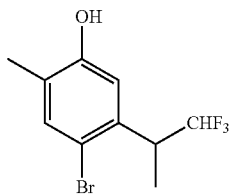

4-Bromo-5-(2,2-difluoro-1-methyl-ethyl)-2-methyl phenol (269)

4-Bromo-5-(2,2-difluoro-1-methyl-ethyl)-2-methyl phenol (269): Compound 269 is derived from 5-bromo-2-methyl phenol according to the procedure described for the synthesis of compound 216, using $CHF_2COCH_3$ instead of $CH_3COCF_3$ in the second step of the synthesis.

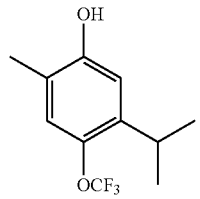 [SMILES: Cc1cc(OC(F)(F)F)c(C(C)C)cc1O]

5-Isopropyl-2-methyl-4-trifluoromethoxy phenol (251)

5-Isopropyl-2-methyl-4-trifluoromethoxy phenol (251): Compound 251 is synthesized from compound 9 in accordance to Scheme IV, conversion A''', B''', and C'''. Scheme IV Conversion A''': A solution compound 9 (1 equivalent), imidazole (2 equivalent), and TBDMSCl (1 equivalent) in anhydrous DMF is stirred at room temperature. After the completion of the reaction, the reaction mixture is partitioned between ether and water. The ether layer is washed ice-cold brine, dried over anhydrous sodium sulfate, filtered, and concentrated under vacuo. The residue is purified by column chromatography to afford the silyl ether. To a solution of silyl ether of compound 9 (1 equivalent) in THF at −78° C. is added nBuLi (1 equivalent). The reaction mixture is stirred at −78° C. for 30 minutes before the addition of $Bu_3SnCl$ (1 equivalent). After stifling for 1 hour at −78° C., the reaction mixture is warmed to room temperature and the solvent is removed in vacuo. The residue is dissolved in ether and filtered through a plug of neutral alumina. The filtrate is concentrated in vacuo and the residue is purified via column chromatography to afford Scheme IV, intermediate $I_1$. Scheme IV Conversion B''': To a suspension of tris(dimethylamino)sulfonium difluorotrimethylsilicate (2.00 equivalent), sodium bicarbonate (2.00 equiv), and Scheme IV intermediate $I_1$ (1.00 equivalent) in anhydrous THF at −30° C. is added trifluoromethyl trifluoromethanesulfonate (4.1 equivalent), and the suspension is stirred vigorously. The reaction mixture is stirred at −30° C. for 30 minutes, then a solution cooled to −30° C. of 1-chloromethyl-4-fluoro-1,4-diazoniabicyclo[2.2.2]octane bis (hexafluorophosphate) (1.20 equivalent) and silver hexafluorophosphate (2.00 equivalent) in dry acetone is added by cannula. The reaction mixture is stirred for 2.5 hours in the dark, then warmed to 23° C. The reaction mixture is filtered through a pad of celite eluting with $CH_2Cl_2$ and the filtrate concentrated in vacuo at 5° C. The residue is purified via column chromatography on silica gel to afford Scheme IV intermediate $I_2$. Scheme IV Conversion C''': A solution of intermediate $I_2$ (1 equivalent) and TBAF (5 equivalent) in THF is stirred at room temperature. After completion of reaction, the solvent is removed under vacuo. The residue is dissolved in water and extracted with ethyl acetate. The combine organic extract is dried over anhydrous sodium sulfate, filtered, and concentrated in vacuo. The residue is purified by column chromatography to afford the compound 251.

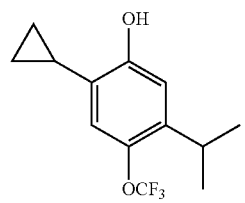 [SMILES: CC(C)c1cc(O)c(C2CC2)cc1OC(F)(F)F]

2-Cyclopropyl-5-isopropyl-4-trifluoromethoxy phenol (253)

2-Cyclopropyl-5-isopropyl-4-trifluoromethoxy phenol (253): Compound 253 is synthesized from compound 240, according to the procedure described for the synthesis of compound 251.

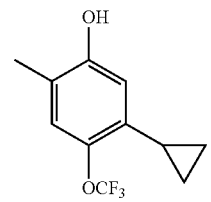 [SMILES: Cc1cc(OC(F)(F)F)c(C2CC2)cc1O]

5-Cyclopropyl-2-methyl-4-trofluoromethoxy phenol (254)

5-Cyclopropyl-2-methyl-4-trofluoromethoxy phenol (254): Compound 254 is synthesized from compound 41, according to the procedure described for the synthesis of compound 251.

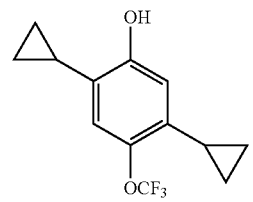 [SMILES: Oc1cc(C2CC2)c(OC(F)(F)F)cc1C1CC1]

2,5-Dicyclopropyl-4-trifluoromethoxy phenol (255)

2,5-Dicyclopropyl-4-trifluoromethoxy phenol (255): Compound 255 is synthesized from compound 247, according to the procedure described for the synthesis of compound 251.

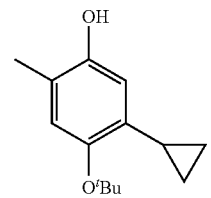 [SMILES: Cc1cc(OC(C)(C)C)c(C2CC2)cc1O]

4-tert-Butoxy-5-cyclopropyl-5-methyl phenol (257)

4-tert-Butoxy-5-cyclopropyl-2-methyl phenol (257): Compound 257 is synthesized from compound 41 in accordance to Scheme IV conversion D'''. A suspension of compound 41 (1.0 equivalent), sodium tert-butoxide (11.0 equivalent), CuI (3.0 equivalent) in DMF is stirred at 110° C. for 48 hours. The reaction mixture is cooled to room temperature followed by addition of ether and aqueous NH₄Cl solution. The aqueous phase is extracted with ether, and the combine organic phase is washed with saturated aqueous NaHCO₃ solution and brine. The organic phase is dried over anhydrous sodium sulfate, filtered, and concentrated under vacuo. The residue is purified by column chromatography to afford the compound 257.

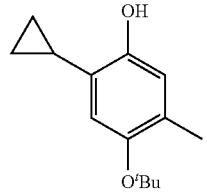 [SMILES: Cc1cc(O)c(C2CC2)cc1OC(C)(C)C]

4-tert-Butoxy-2-cyclopropyl-5-methyl phenol (258)

4-tert-Butoxy-2-cyclopropyl-5-methyl phenol (258): Compound 258 is synthesized from commercially available 3-methyl phenol in accordance to (a) Scheme II conversion H', J, and K, (b) Scheme III conversion A", and (c) Scheme IV conversion D'". Scheme II Conversion H', J, and K: The intermediate 2-cyclopropyl-5-methyl phenol is synthesized from 3-methyl phenol according to the procedure described for the synthesis of Scheme II intermediate phenol I₁₂, obtained during the synthesis of compound 240. Scheme III conversion A": 2-cyclopropyl-5-methyl phenol is brominated at 4-position according to the procedure described for the synthesis of compound 9, to afford Scheme III intermediate phenol I₂. Scheme IV Conversion D'": Compound 258 is synthesized from Scheme intermediate phenol I₂, by the procedure described for the synthesis of compound 257.

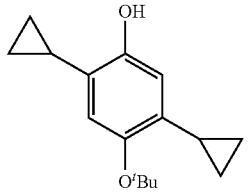 [SMILES: CC(C)(C)Oc1cc(C2CC2)c(O)cc1C1CC1]

4-tert-Butoxy-2,5-dicyclopropyl phenol (259)

4-tert-Butoxy-2,5-dicyclopropyl phenol (259): Compound 259 is synthesized from compound 247, according to the procedure described for the synthesis of compound 257.

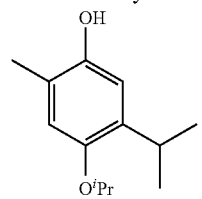

4-Isopropoxy-5-isopropyl-5-methyl phenol (261)

4-Isopropoxy-5-isopropyl-5-methyl phenol (261): Compound 261 is synthesized from compound 9, according to the procedure described for the synthesis of compound 257, using sodium isopropoxide instead of sodium tert-butoxide.

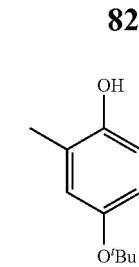

4-tert-Butoxy-5-isopropyl-2-methyl phenol (272)

4-tert-Butoxy-5-isopropyl-2-methyl phenol (272): Compound 272 is synthesized from compound 9, according to the procedure described for the synthesis of compound 251.

Pro-Drugs

Alkyl/Aryl Ester Pro-Drugs

Phenols are excellent nucleophiles known to condense with a wide variety of acid chlorides. For example, compound 9 can be treated with acid chloride in the presence of base to provide the 4-bromo-5-isopropyl-2-methyl phenol alkyl/aryl esters (Scheme V). Given that there are a number of commercially available acid chlorides, a wide variety of this class of pro-drug with a wide variety of oral bioavailability and pharmacokinetic parameters can be synthesized. Those of skill in the art will understand that the exemplary scheme set forth in Scheme V shows one reaction among many, and should not be construed to limit the invention.

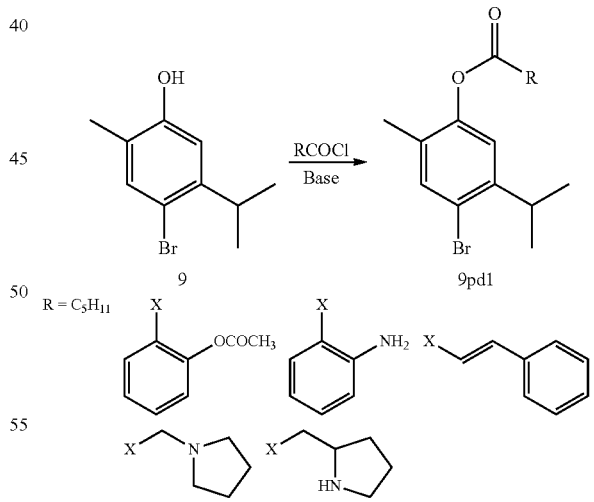

Scheme V. Synthesis of Alkyl and aryl esters of Compound 9

Carbonate and Carbamate Prodrugs

Numerous chloroformate derivatives are commercially available. Reaction of a phenol with a chloroformate (Scheme VI) can yield excellent prodrugs with improved oral absorption and desirable PK properties.

Scheme VI. Synthesis of Carbonate Pro-drugs of 9

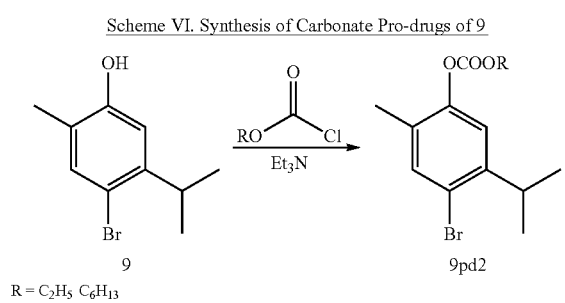

R = C₂H₅ C₆H₁₃

Carbamates prodrugs can protect the parent phenol drug against first-pass metabolism following oral administration or can serve as substrates for specific enzymes. The use of carbamate prodrugs also helps in increasing the lipophilicity of the prodrug at neutral pH and to increase the aqueous solubility at an acidic pH. Several amines are commercially available and they can be coupled with 4-bromo-5-isopropyl-2-methyl phenyl chloroformate to give the carbamates of Scheme VII.

Scheme VII. Synthesis of Carbamate Pro-Drugs of Compound 9

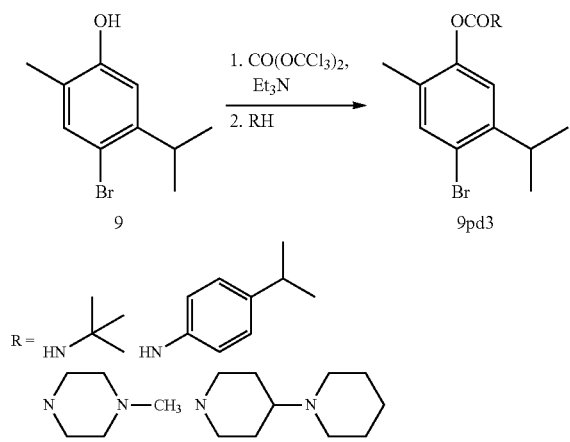

Phosphate Prodrugs

Prodrugs containing a phosphate moiety have been successfully employed for increasing oral absorption and modulation of duration of action in vivo. Shown below are potential phosphate containing analogs of compound 9 and 11 (Scheme VIII).

Scheme VIII. Synthesis of Phosphate esters Pro-Drug of Compound 9 and 11

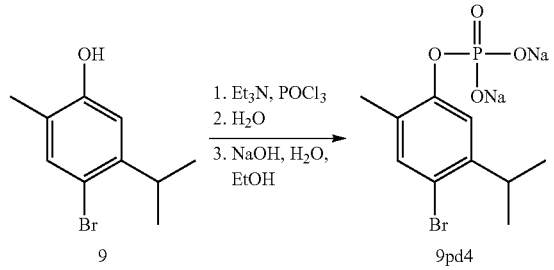

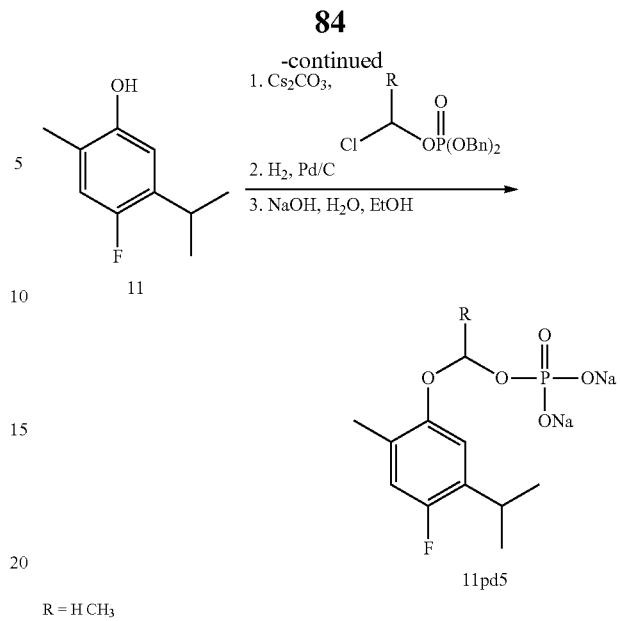

R = H CH₃

Ether Prodrugs

Ether prodrug approach has been used to enhance lipophilicity, favoring the permeation into cellular membranes and the blood brain barrier, and/or to improve the pharmacokinetic properties of the parent drug. Many phenolic group-containing drugs cannot be administrated orally due to their rapid metabolism by the enzymes in the intestinal tract and liver. Ether prodrugs undergo chemical hydrolysis and are not always enzyme dependent for their cleavage. O-(saccharinylmethyl) prodrug can protect the drug from first pass metabolism and increase the drugs oral potency. It can be synthesized by treating the phenol with saccharinyl methyl chloride (Scheme IX).

Scheme IX. Synthesis of Ether Prodrugs: O-(Saccharinylmethyl) derivative of Compound 9

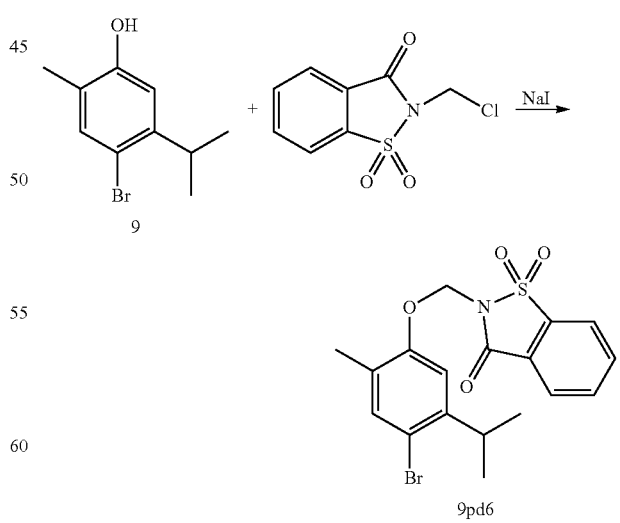

Glycosides derivatives of dopamine have shown high stability in plasma and a sustained release of dopamine in brain extract through an activation mechanism catalyzed by glycosidase. A glycosyl derivative can be prepared by coupling the phenol with glucose penta acetate (Scheme X).

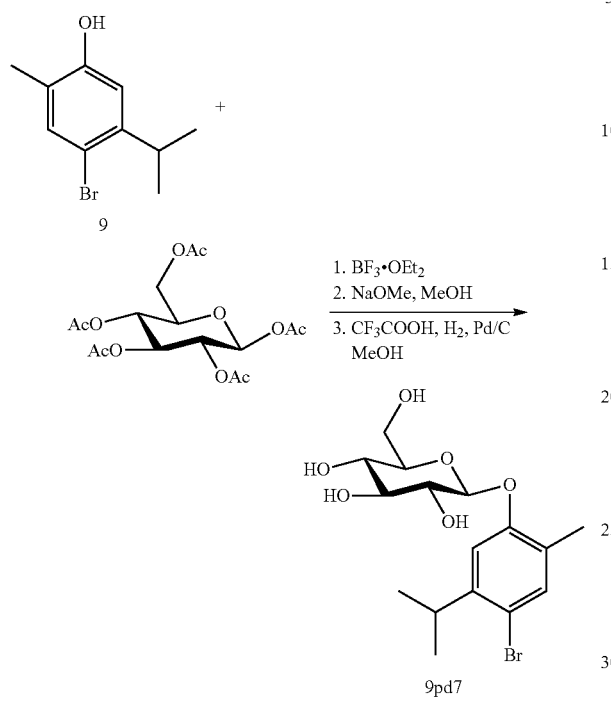

Scheme X: Ether Prodrugs: Synthesis of Glycosyl derivative of Compound 9

The N-alkyloxycarbonylaminomethyl and alkylcarbonyloxymethyl prodrugs have been used for the topical delivery of the phenol drug and increase its biphasic stability. The synthesis can be achieved as described in Scheme XI.

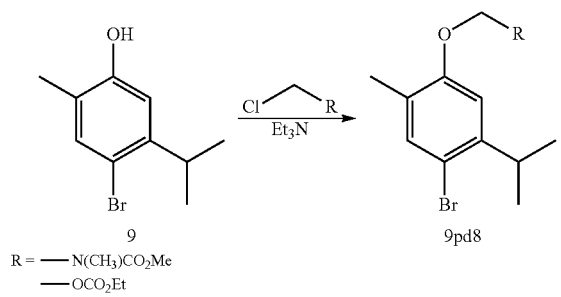

Scheme XI. Ether Prodrugs: Synthesis N-alkoxycarbonylaminomethyl and Alkylcarbonyoxymethyl derivatives of compound 9

Sulfamate Prodrugs

Sulfamate ester pro-drugs have been employed to mitigate hepatic first-pass metabolism of selected phenol drugs. Once these molecules reach systemic circulation they are converted by hydrolysis to the corresponding phenols by esterases and amidases. Shown in Scheme XII is a sulfamate ester of compound 9. A variety of substituents can be incorporated into the sulfamate moiety to modulate kinetics of parent molecule release.

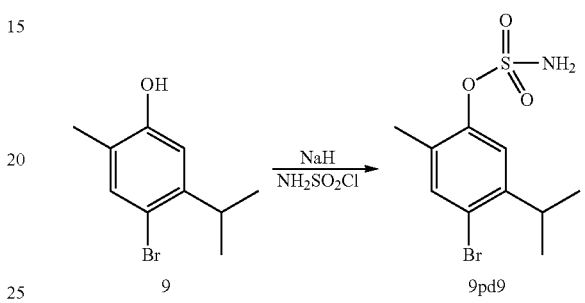

Scheme XII. Synthesis of Sulfamate Prodrug of compound 9

H. Biological Assays

1. Minimal Clonic Seizure (6 Hz, 32 mA or 44 mA) Test

The minimal clonic seizure (6 Hz) test is used to assess a compound's efficacy against electrically induced seizures but uses a lower frequency (6 Hz) and longer duration of stimulation (3 s) than the MES test (Barton M E K B, Wolf H H, White H S: Pharmacological characterization of a 6 HZ psychomotor seizure model of partial epilepsy. Epilepsy Res 2001; 47:217-27). Test compounds are pre-administered to mice via i.p. injection. At varying times, individual mice (four per time point) are challenged with sufficient current delivered through corneal electrodes to elicit a psychomotor seizure in 97% of animals (32 mA or 44 mA for 3 s) (Toman J E P, Everett G M, Richards R K: The Search for New Drugs against Epilepsy. Texas Reports on Biology and Medicine 1952; 10:96-104). Untreated mice will display seizures characterized by a minimal clonic phase followed by stereotyped, automatistic behaviors described originally as being similar to the aura of human patients with partial seizures. Animals not displaying this behavior are considered protected. The test compounds are evaluated quantitatively by measuring the responses at varying doses at a determined time of peak effect (TPE).

| | | | Efficacy | | | Toxicity | | |
|---|---|---|---|---|---|---|---|---|
| | Species | Route | Dose (mg/kg) | Time (TPE) (hrs) | animals protected/animals tested | Dose (mg/kg) | Time (TPT) (hrs) | Toxicity Ratio |
| Ex. 9 | Mouse | IP | 100 | 0.5 | 3/4 | 100 | N/A | 0/4 |
| | Mouse | Oral | 100 | N/A | 0/4 | 100 | N/A | 0/4 |
| Ex. 132 | Mouse | IP | 100 | 0.5 | 3/4 | 100 | N/A | 0/4 |
| Ex. 204 | Mouse | IP | 100 | 0.5 | 2/4 | 100 | N/A | 0/4 |
| Ex. 64 | Mouse | IP | 30 | 0.5 | 1/4 | 30 | NA | 0/8 |

6 Hz 32 mA Epilepsy Model (Qualitative Screen) - Test 7-1

6 Hz 32 mA Epilepsy Model (Qualitative Screen) - Test 7-1

|  | Species | Route | Dose (mg/kg) | Efficacy Time (TPE) (hrs) | animals protected/animals tested | Dose (mg/kg) | Toxicity Time (TPT) (hrs) | Toxicity Ratio |
|---|---|---|---|---|---|---|---|---|
|  | Mouse | IP | 100 | 0.5 | 3/4 | 100 | NA | 0/8 |
|  | Mouse | IP | 300 | 0.5 | 4/4 | 300 | 0.5 | 6/8 |
| Ex. 25 | Mouse | IP | 30 | 0.5 | 2/4 | 30 | NA | 0/8 |
|  | Mouse | IP | 100 | 0.5 | 2/4 | 100 | NA | 0/8 |
|  | Mouse | IP | 300 | 2 | 4/4 | 300 | 0.5 | 4/8 |
| Ex. 95 | Mouse | IP | 30 | 0.5 | 0/4 | 30 | 0.5 | 0/8 |
|  | Mouse | IP | 10 | 0.5 | 3/4 | 10 | 0.5 | 1/8 |
|  | Mouse | IP | 300 | 0.5 | 3/4 | 300 | 0.5 | 3/8 |

6 Hz 32 mA Model (Dose Response) - Test 7-2

|  | Efficacy Time (TPE) (hrs) | $ED_{50}$ (mg/kg) | Toxicity Time (TPT) (hrs) | $TD_{50}$ (mg/kg) | Protective Index (PI) |
|---|---|---|---|---|---|
| Ex. 9 | 0.5 | 19 | 6 | 398 | 21.5 |
| Ex. 132 | 0.5 | 28 | 4 | >200 | >7.3 |

Corneal Kindled Mouse - Test 26

|  | Species | Route | Dose (mg/kg) | Time (TPE) (hrs) | Seizure Ratio | Average Seizure Score |
|---|---|---|---|---|---|---|
| Ex. 9 | Mouse | IP | 19 | 0.5 | 1/4 | 3.75 |
| Ex. 132 | Mouse | IP | 28 | 0.5 | 1/4 | 4.5 |

6 Hz 44 mA Epilepsy Model (Qualitative Screen) - Test 7-3

|  | Species | Route | Dose (mg/kg) | Efficacy Time (TPE) (hrs) | animals protected/animals tested | Dose (mg/kg) | Toxicity Time (TPT) (hrs) | Toxicity Ratio |
|---|---|---|---|---|---|---|---|---|
| Ex. 132 | Mouse | IP | 100 | 2 | 2/4 | 100 | NA | 0/4 |
| Ex, 64 | Mouse | IP | 100 | 0.25 | 1/4 | 100 | N/A | 0/4 |

2. Corneal Kindling (Focal Seizures)

Mice are kindled electrically with 3 sec stimulation, 8 mA, 60 Hz, and corneal electrodes to a criterion of 10 consecutive Stage 5 seizures (facial clonus and head nodding progressing to forelimb clonus, and finally rearing and falling accompanied by a generalized clonic seizure as described by Racine (Racine R J: Modification of Seizure Activity by Electrical Stimulation. II. Motor Seizure. Electroen Clin Neuro 1972; 32:281-94). Stage 5 is generally reached after twice daily stimulation for 8 days. With continued stimulation once a day, animals usually progress to a reproducible Stage 5 after 10-14 additional days. At least 72 hours after the mice have been kindled, the test substance is administered either intraperitoneal (i.p.) or per os (p.o.) and, at the previously determined TPE, each animal is given the electrical stimulus indicated above. Following stimulation, the animals are observed for the presence or absence of the rearing and falling criteria of a Stage 5 seizure. Treated animals not displaying a Stage 3, 4, or 5 seizure are considered protected. The dose of the test substance is varied between the limits of 0 and 100% efficacy, and the $ED_{50}$ and 95% confidence intervals calculated by probit analysis. Mean values and the S.E.M. are calculated for the length of clonus and seizure duration and p values are determined by the Student's t-test.

3. Maximal Electroshock Seizure (MES) Test

MES test is performed as in the Minimal Clonic Seizure (6 Hz) test, but the MES test utilizes a current of 50 mA (mice) or 150 mA (rats), frequency of 50-60 Hz, and a stimulation time of 0.2 seconds. Upon stimulation, untreated test subjects display immediate severe tonic seizure (including maximal extension of legs) and the body becomes stiffened for roughly 10-15 seconds. Next, clonic seizures start (including shaking of body and paddling movements of the hind limbs) and may last 20-30 seconds (Castel-Branco M M, Alves G L, Figueiredo I V, Falcao A C, Caramona M M: The Maximal Electroshock Seizure (MES) Model in the Preclinical Assessment of Potential New Antiepileptic Drugs. Methods and Findings in Experimental and Clinical Pharmacology 2009; 31:101-06). Test subjects that display reduced or eliminated symptoms of MES-type seizures during and/or after stimulation are considered protected.

MES Model (Screen) - Test 1, 2, 8

|  | Species | Route | Dose (mg/kg) | Time (TPE) (hrs) | animals protected/animals tested | Time (TPT) (hrs) | Toxicity Ratio |
|---|---|---|---|---|---|---|---|
| Ex. 9 | Mouse | IP | 100 | 0.25 | 1/4 | N/A | 0/8 |
| Ex. 132 | Mouse | IP | 100 | 1 | 2/4 | 0.5 | 1/8 |
| Ex. 204 | Mouse | IP | 100 | 0.25 | 1/4 | N/A | 0/8 |

-continued

| | Species | Route | Dose (mg/kg) | Time (TPE) (hrs) | animals protect-ed/animals tested | Time (TPT) (hrs) | Toxicity Ratio |
|---|---|---|---|---|---|---|---|
| Ex. 64 | Mouse | IP | 30 | NA | 0/4 | NA | 0/8 |
| | Mouse | IP | 100 | 0.5 | 1/4 | NA | 0/8 |
| | Mouse | IP | 300 | 0.5 | 2/4 | 0.5 | 6/8 |
| Ex. 25 | Mouse | IP | 30 | NA | — | — | — |
| | Mouse | IP | 100 | NA | — | — | — |
| | Mouse | IP | 300 | NA | — | — | — |
| Ex. 95 | Mouse | IP | 30 | 0.5 | 0/4 | — | — |
| | Mouse | IP | 100 | 0.5 | 0/4 | — | — |
| | Mouse | IP | 300 | 0.5 | 1/4 | — | — |

4. Acute Toxicity-Minimal Motor Impairment

To assess a compound's undesirable side effects (toxicity), animals are monitored for overt signs of impaired neurological or muscular function. In mice, the rotorod (Dunham N W, Miya T S: A Note on a Simple Apparatus for Detecting Neurological Deficit in Rats and Mice. Journal of the American Pharmaceutical Association 1957; 46:208-09), procedure is used to disclose minimal muscular or neurological impairment. When a mouse is placed on a rod that rotates at a speed of 6 rpm, the animal can maintain its equilibrium for long periods of time. The animal is considered toxic if it falls off this rotating rod three times during a 1-min period. In rats, minimal motor deficit is indicated by ataxia, which is manifested by an abnormal, uncoordinated gait. Rats used for evaluating toxicity are examined before the test drug is administered, since individual animals may have peculiarities in gait, equilibrium, placing response, etc., which might be attributed erroneously to the test substance. In addition to minimum motor impairment, animals may exhibit a circular or zigzag gait, abnormal body posture and spread of the legs, tremors, hyperactivity, lack of exploratory behavior, somnolence, stupor, catalepsy, loss of placing response, and changes in muscle tone.

The above examples are strictly exemplary, and should not be construed to limit the scope or understanding of the present invention. It should be understood by those skilled in the art that various changes may be made and equivalents may be substituted without departing from the true spirit and scope of the Invention. In particular, syntheses of exemplary prodrugs are disclosed herein, but the teachings provided could be applied to any chemically analogous drug. In addition, many modifications may be made to adapt a particular situation, material, composition of matter, process, process step or steps, to the objective, spirit and scope of the described invention. All such modifications are intended to be within the scope of the claims appended hereto. It must also be noted that as used herein and in the appended claims, the singular forms "a," "an," and "the" include plural referents unless the context clearly dictates otherwise. Each technical and scientific term used herein has the same meaning each time it is used. The use of "or" in a listing of two or more items indicates that any combination of the items is contemplated, for example, "A or B" indicates that A alone, B alone, or both A and B are intended. The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be confirmed independently.

What is claimed is:

1. A method of treating a neurological condition in a patient in need thereof, wherein the neurological condition is selected from the group consisting of Alzheimer's Disease, convulsions, epilepsy, Huntington's Chorea, migraine headache, neuropathic pain, Parkinson's Disease, seizures, and tremors, the method comprising administering a therapeutically effective amount of a compound or pharmaceutically acceptable salt of the compound, wherein the compound has the structure of Formula (I):

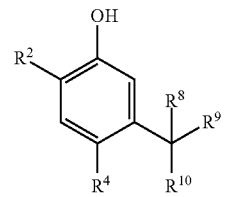

wherein:
  R2 is selected from the group consisting of alkyl, haloalkyl, and cycloalkyl;
  R4 is selected from the group consisting of H, Br, Cl, and F; and
  R8, R9 and R10 are each independently selected from the group consisting of H, alkyl, and haloalkyl.

2. The method of claim 1, wherein the compound is selected from the group consisting of 4-bromo-5-isopropyl-2-methyl-phenol, 4-bromo-2,5-isopropyl-phenol, and 5-isopropyl-2-n-propyl-phenol.

3. The method of claim 1, wherein the neurological condition is epilepsy, seizures, or convulsions.

4. The method of claim 1, wherein the neuropathic pain is fibromyalgia.

5. The method of claim 1, wherein the neurological condition is selected from the group consisting of Alzheimer's Disease, Huntington's Disease, and Parkinson's Disease.

6. The method of claim 1, wherein R2 has 1-5 carbons.

7. The method of claim 6, wherein the compound is selected from a group consisting of: 4-chloro-5-tert-butyl-2-methyl-phenol; 4-chloro-2-isopropyl-5-methyl-phenol; 4-fluoro-2-isopropyl-5-methyl-phenol; 4-chloro-2,5-diisopropyl-phenol; 4-bromo-5-isopropyl-2-methyl-phenol; 4-bromo-2-isopropyl-5-methyl-phenol; 4-bromo-2-tert-butyl-5-isopropyl-phenol; 4-bromo-5-tert-butyl-2-methyl-phenol; and 4-fluoro-5-tert-butyl-2-methyl-phenol.

8. The method of claim 1 wherein:
  alkyl is selected from the group consisting of methyl, ethyl, propyl, isopropyl, butyl, isobutyl, tert-butyl, sec-butyl, pentanyl, isopentanyl, and neopentanyl;
  haloalkyl is selected from the group consisting of fluoromethyl, 1-fluoroethyl, 2-fluoroethyl, 1-fluoropropyl, 2-fluoropropyl, 3-fluoropropyl, chloromethyl, 1-chloroethyl, 2-chloroethyl, 1-chloropropyl, 2-chloropropyl, 3-chloropropyl, bromomethyl, 1-bromoethyl, 2-bromoethyl, 1-bromopropyl, 2-bromopropyl, and 3-bromopropyl; and
  cycloalkyl is selected from the group consisting of cyclopropyl, cyclobutyl, cyclopentyl, and cyclohexyl.

* * * * *